United States Patent [19]

Nakamura et al.

[11] Patent Number: 4,953,539
[45] Date of Patent: Sep. 4, 1990

[54] ENDOSCOPE APPARATUS

[75] Inventors: Kazunari Nakamura, Hachioji; Toshihiko Hagiwara, Hino; Akira Takano, Hachioji, all of Japan

[73] Assignee: Olympus Optical Co., Ltd., Tokyo, Japan

[21] Appl. No.: 375,435

[22] Filed: Jul. 5, 1989

Related U.S. Application Data

[63] Continuation-in-part of Ser. No. 137,779, Dec. 24, 1987, abandoned, and a continuation-in-part of Ser. No. 230,820, Aug. 11, 1988, abandoned.

[30] Foreign Application Priority Data

| Dec. 26, 1986 | [JP] | Japan | 61-313274 |
| Dec. 26, 1986 | [JP] | Japan | 61-313271 |
| Sep. 1, 1987 | [JP] | Japan | 62-219337 |
| Dec. 8, 1987 | [JP] | Japan | 62-311297 |

[51] Int. Cl.⁵ .............................................. A61B 1/06
[52] U.S. Cl. .................................... 128/6; 128/633
[58] Field of Search ................. 128/4, 6, 633, 634

[56] References Cited

U.S. PATENT DOCUMENTS

| 4,429,686 | 2/1984 | Hosoda | 128/6 |
| 4,618,884 | 11/1986 | Nagasaki | 358/98 |
| 4,646,743 | 3/1987 | Parris | 128/396 |
| 4,685,451 | 8/1987 | Ando | 128/6 |
| 4,759,347 | 7/1988 | Ando | 128/6 |
| 4,768,089 | 7/1988 | Kato | 358/98 |

FOREIGN PATENT DOCUMENTS 54-21678 8/1979 Japan .
56-50576 11/1981 Japan .
61-87532 5/1986 Japan .

Primary Examiner—William H. Grieb
Attorney, Agent, or Firm—Armstrong, Nikaido, Marmelstein, Kubovcik & Murray

[57] ABSTRACT

An endoscope apparatus has an illuminating device for applying at least infrared illuminating light to the interior of an organic body across the organic tissue of the body, an elongated insert portion to be inserted into the body, and an image pickup device having a light-receiving portion provided on an end of the insert portion and capable of picking up the infrared image of an object illuminated by the light transmitted through the tissue of the body. The endoscope apparatus further has an exposure amount control device capable of controlling the amount of exposure of the object by the illuminating device and applied to the object through the tissue of the body, and the amount of exposure of the object by illuminating light from another illuminating device which applies illuminating light to the object from inside of the body. The endoscope light source apparatus also comprises a body outside illuminating apparatus transmittively illuminating from outside the body the part observed with the endoscope. The exposure controlling apparatus controlling at least one of the exposure to the body inside illuminating light body from the body inside illuminating light source and the exposure to the outside illuminating light. The body outside illuminating light source can be made integral with the body inside illuminating light source and have a light transmitting member transmitting the light emitted from this body outside illuminating light source to a predetermined position outside the body and emitting it.

71 Claims, 38 Drawing Sheets

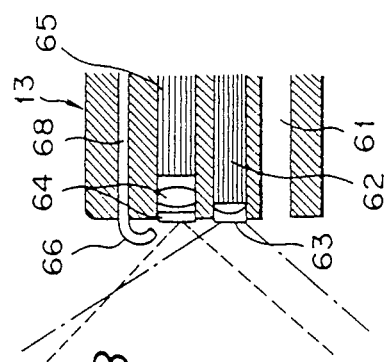
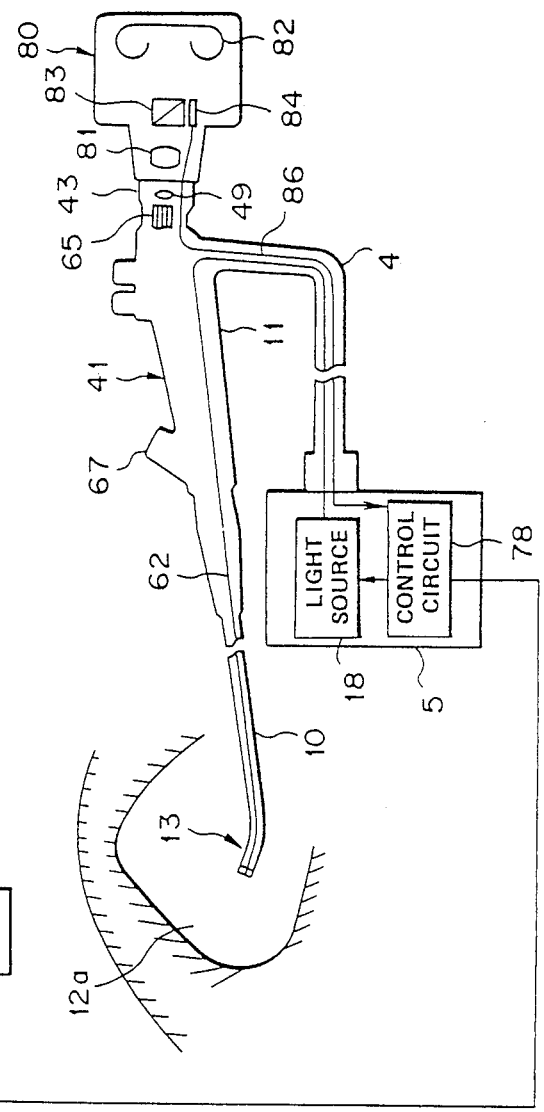
FIG.8
FIG.9

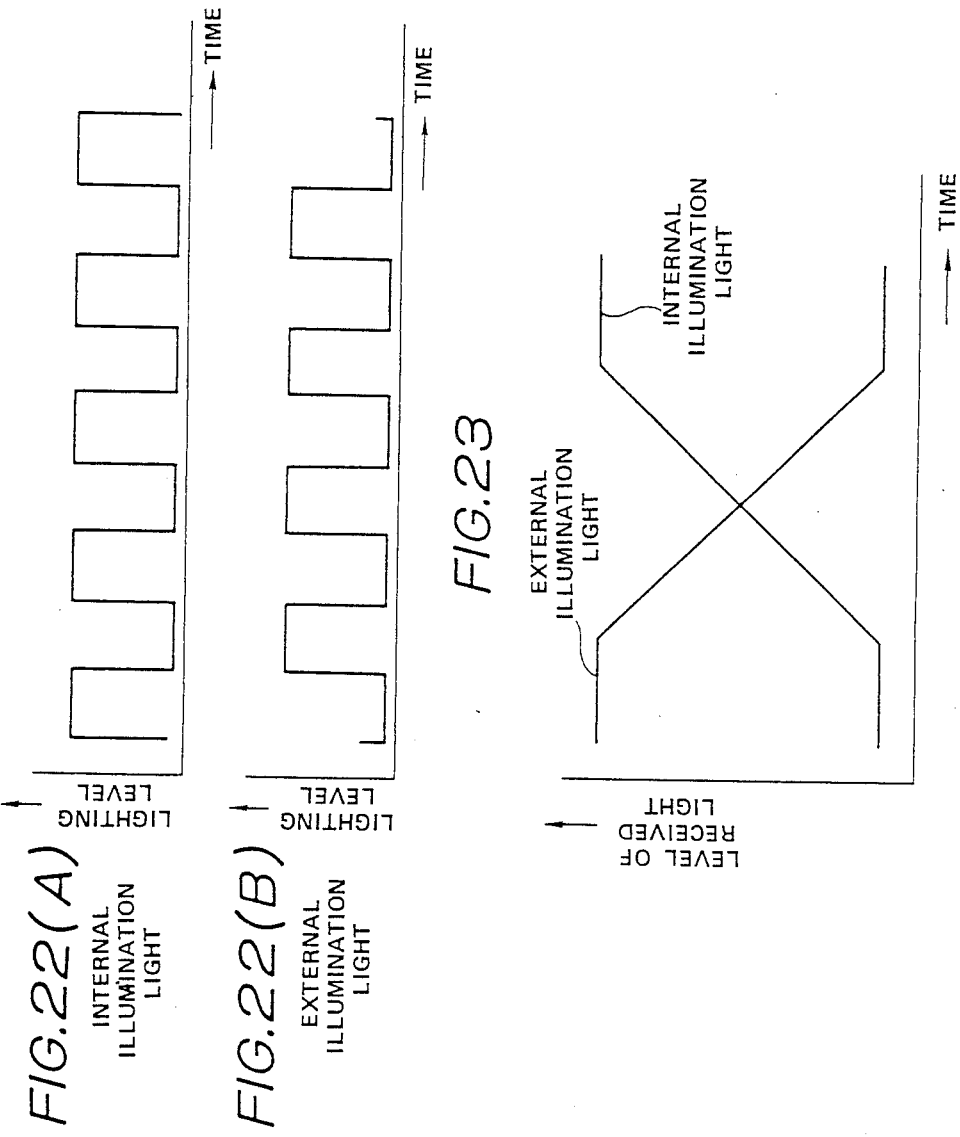

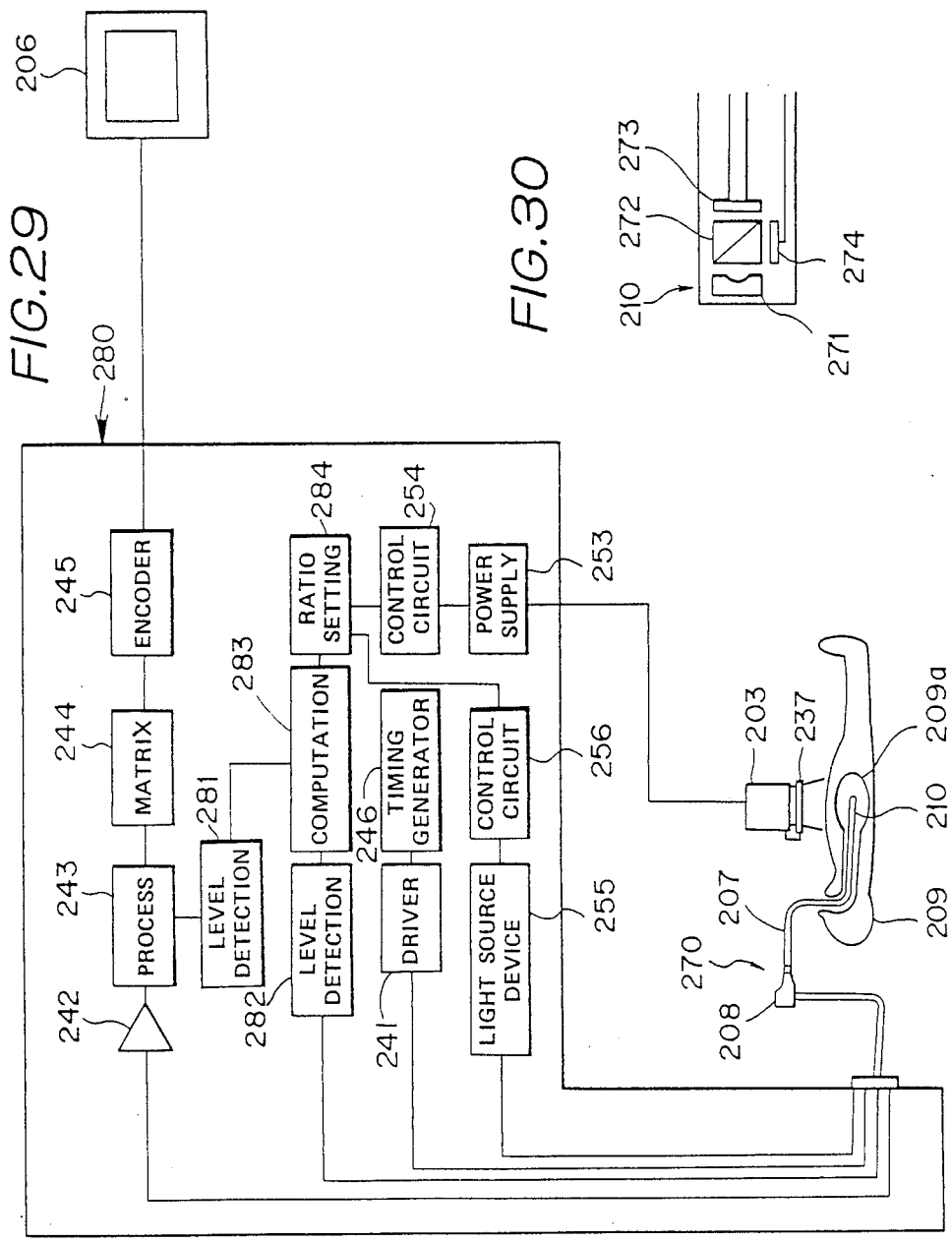

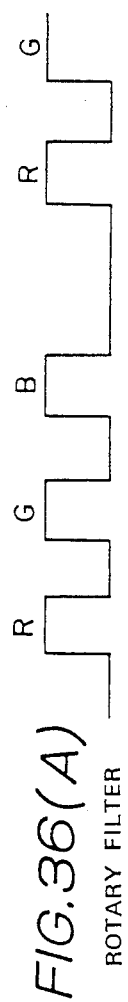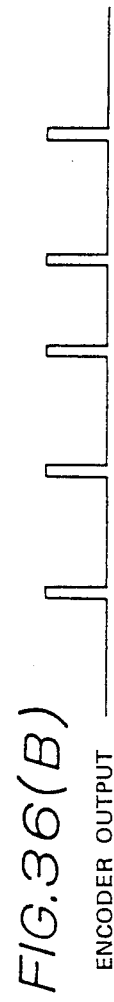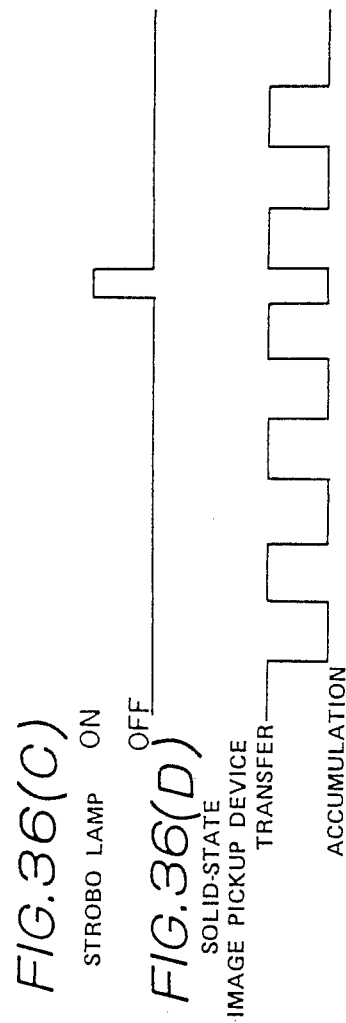

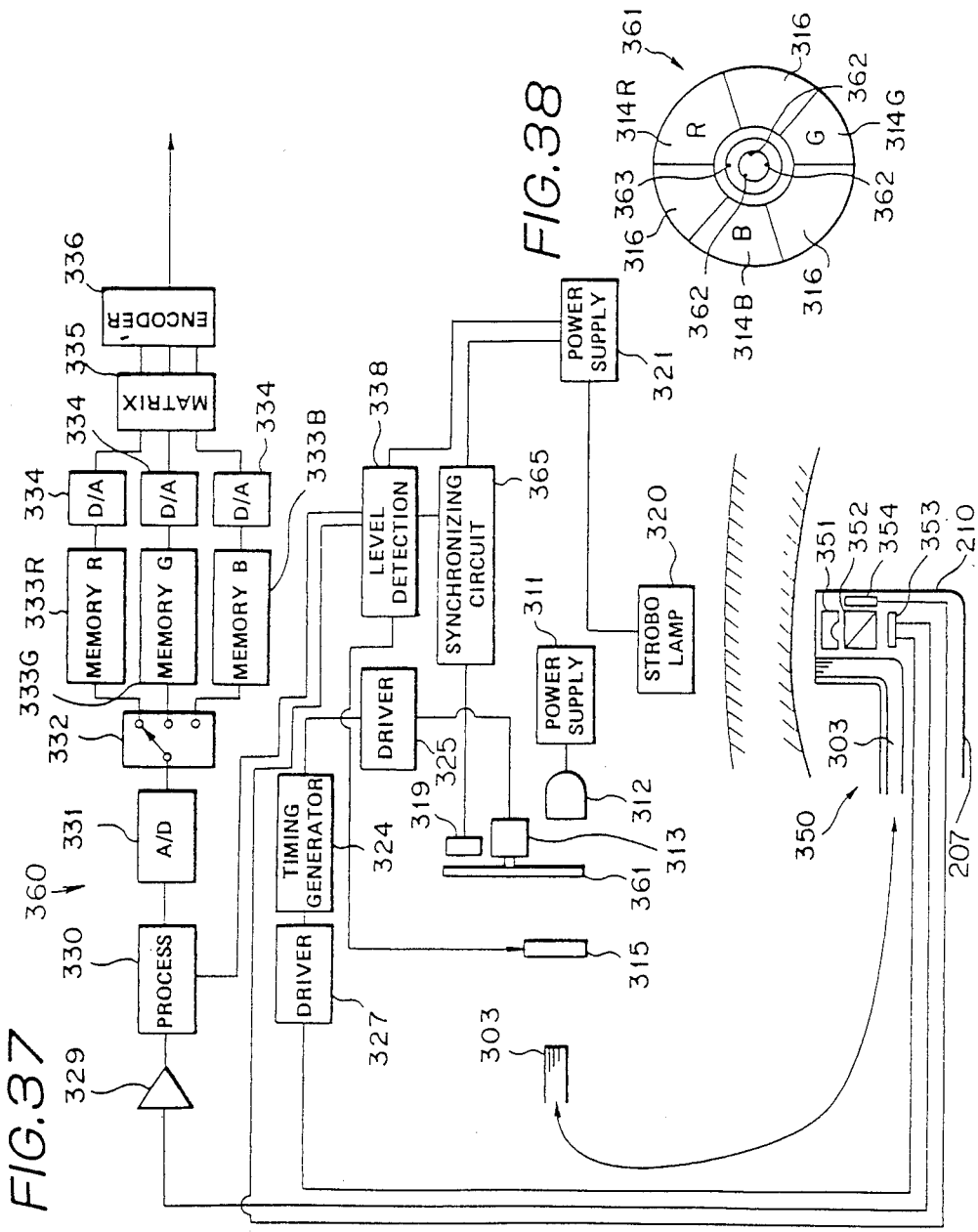

FIG. 39
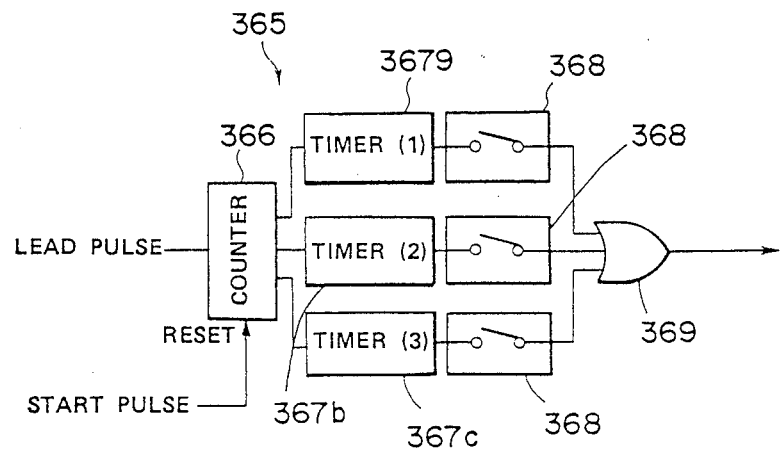
FIG. 40(A) ROTARY FILTER
FIG. 40(B) ENCODER START PULSE
FIG. 40(C) ENCODER LEAD PULSE
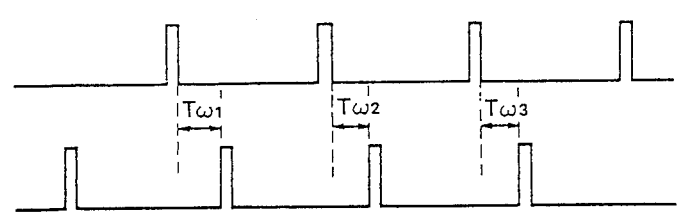
FIG. 40(D) SYNCHRONIZING CIRCUIT OUTPUT
FIG. 40(E) SOLID-STATE IMAGE PICKUP DEVICE TRANSFER ACCUMULATION
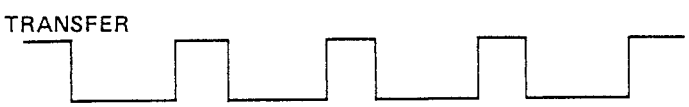

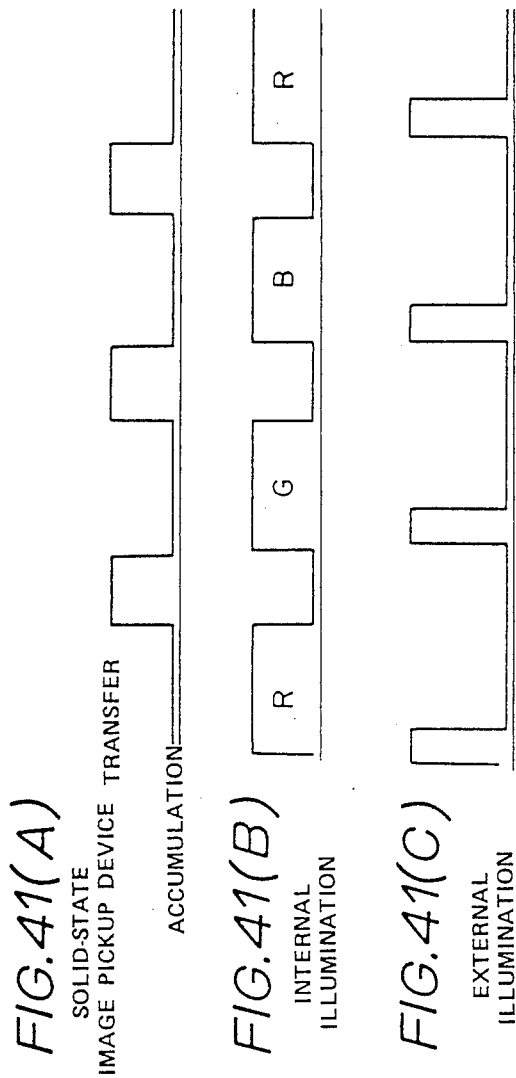

SOLID STATE IMAGE PICKUP DEVICE
ACCUMULATION-
TRANSFER-

FLASH SIGNAL

EXTERNAL ILLUMINATION

INTERNAL ILLUMINATION

SWITCH CIRCUIT

SWITCH CIRCUIT

SOLID-STATE IMAGE PICKUP DEVICE

EXTERNAL ILLUMINATION

FIG.48(A) SOLID-STATE IMAGE PICKUP DEVICE ACCUMULATION—TRANSFER
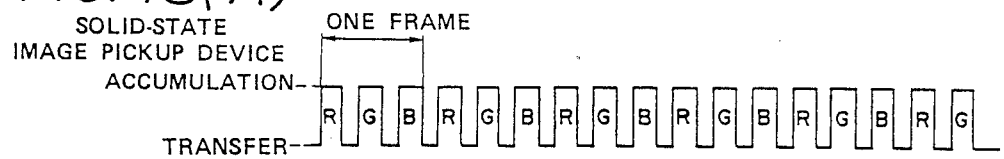
FIG.48(B) FLASH SIGNAL
FIG.48(C) INTERNAL DISPLAY IMAGE / EXTERNAL
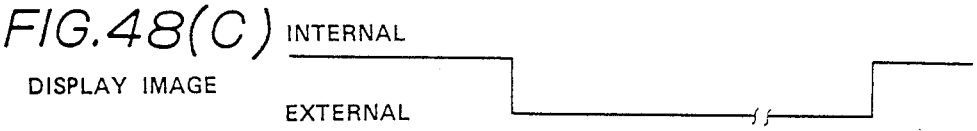
FIG.48(D) EXTERNAL ILLUMINATION
FIG.48(E) INTERNAL ILLUMINATION
FIG.48(F) WRITING — FIRST MEMORY CIRCUIT / SECOND MEMORY CIRCUIT
FIG.48(G) READING — FIRST MEMORY CIRCUIT / SECOND MEMORY CIRCUIT
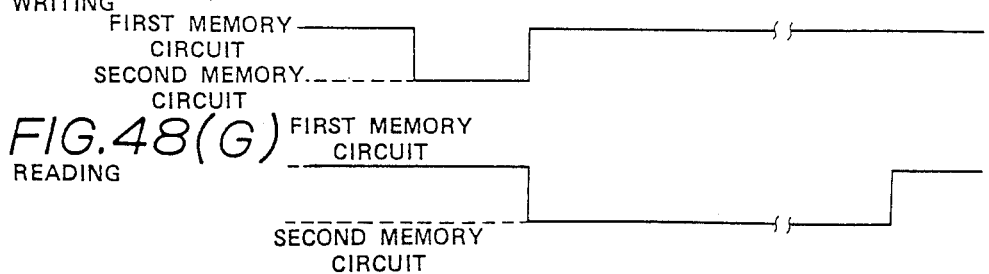

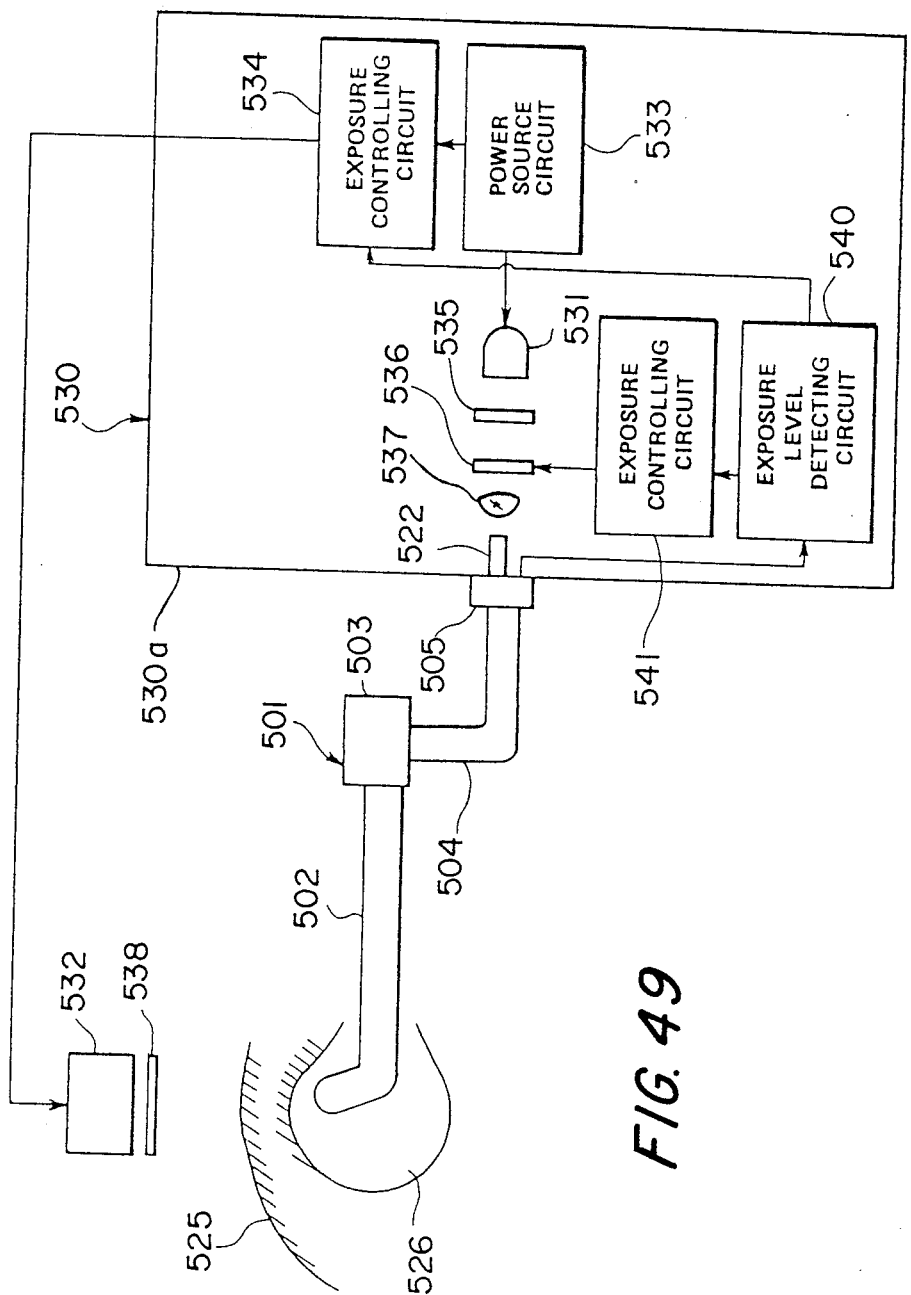

ENDOSCOPE APPARATUS

This is a combined continuation-in-part application of application Ser. No. 07/137,779 filed Dec. 24, 1987 and 07/230,820 filed Aug. 11, 1988, both now abandoned.

BACKGROUND OF THE INVENTION

1. Field of the Invention

The present invention relates to an endoscope apparatus which enables the interior of an organic tissue to be observed by making use of light which has transmitted through the organic tissue.

This invention also relates to an endoscope light apparatus whereby an illumination from inside and outside a body cavity is possible.

2. Related Art Statement

In recent years, an endoscopic apparatus is widely used having an elongated probe portion inserted into body cavities to enable organs in the cavity to be observed. An endoscopic apparatus is also known which has an instrument channel through which an instrument is inserted as desired to effect a required treatment on an internal organ.

The conventional endoscope apparatus is designed to illuminate an objective organ in a body cavity and to collect the light reflected by the organ so as to form an image thereby allowing the organ to be observed. On the other hand, there is an increasing demand in the medical field for an apparatus which enables the user to observe not only the external surface of the organ in the body cavity but also other portions such as the reverse side of gastric wall, blood vessels in membrana, state of tumour and so forth.

In compliance with such a demand, Japanese Pat. Publication No. 21678/1979 discloses an endoscope apparatus which enables the user to observe an object by making use of light which has transmitted through an organic tissue.

However, an external illumination of a body with ordinary visible rays cannot provide sufficiently high level of light input to the endoscope because organic tissue usually has a small permeability or transmission factor to such ordinary visible rays. In consequence, the observation or the diagnosis is difficult to make due to insufficient input light. To eliminate this problem, it is necessary to employ a large-power light source which is large in size and weight and which consumes much electric power.

Medical diagnosis or observation is often conducted by making reference both to an image formed by light applied by an external light source and transmitted through the organic tissue and an image which is obtained by internal illumination provided by a light source inserted into a body cavity. Obviously, the quantity of the light from the external light source transmitted through the organic tissue varies depending on the position of observation. The conventional endoscope apparatus, however, is not designed to enable the ratio of intensity between the image formed by internal illumination and the image formed by external illumination. Thus, the user cannot optimize the ratio of intensity of images for the varying positions of observation.

The endoscope apparatus disclosed in Japanese Pat. Publication No. 21678/1979 also suffers from a disadvantage in that it cannot provide continuous image of object by the transmitted light because it is designed for photographing images in synchronization with flash light.

Japanese Pat. Publication No. 50576/1981, having a priority on Swedish Pat. Application No. 7613587-0, discloses an apparatus in which a light of a high level of lightness is applied to human body tissue and the image formed by this light transmitted through the human body tissue is photographed through an infrared filter. This apparatus, however, has a problem in that only limited portions of the human body can be observed because both the light source and the infrared film are disposed outside the human body.

Recently, there has also come to be extensively used an endoscope whereby organs within a body cavity can be observed by inserting an elongated insertable part into the body cavity or, as required, various therapeutic treatments can be made by using treating tools inserted through a treating tool channel.

Conventionally, a body cavity inside has been observed and therapeutically treated with such an endoscope by reflectively illuminating the body cavity inside tissue surface, such as the mucous membrane surface, with an illumination from the tip of the endoscope insertable part inserted into the body cavity and receiving and imaging the reflected light. However, with the conventional illumination, only the tissue surface can be observed.

Now, it is recently required to observe not only the surface of a body cavity inside tissue but also such tissue inside as the running state of veins below the mucous membrane or the penetrating range of a disease below the mucous membrane. Therefore, as shown in the publication of a Japanese Pat. publication No. 21678/1979, it is suggested to provide an outside illuminating mechanism provided outside a living body cavity to illuminate the living body from outside.

Also, a larynx stroboscope whereby the light of a flash lamp can be fed to an endoscope or the like is disclosed in the publication of a Japanese Pat. application laid open No. 87532/1986. However, this apparatus is not to feed the endoscope with a body inside illuminating light and body outside illuminating light.

SUMMARY OF THE INVENTION

Accordingly, an object of the present invention is to provide an endoscope apparatus which enables an interior of an organic tissue to be easily observed by means of light which has been transmitted through the organic tissue.

Another object of the present invention is to provide an endoscope apparatus which makes it possible to efficiently observe both an image formed by external light transmitted through an organic tissue from the exterior and an image formed by internal illumination light.

Still another object of the present invention is to provide an endoscope apparatus which makes it possible to control the ratio of the intensity between the image formed by the light transmitted through an organic tissue from an external light source and the image formed by light from a light source for internal illumination, thereby optimizing the respective images for observation.

A further object of the present invention is to provide an endoscope apparatus which enables the image formed by the transmitted light to be photographed continuously thereby enabling the transmitted light image to be compared with a reflective image formed by the light from an internal light source.

To this end, according to the present invention, there is provided an endoscope apparatus which comprises an illuminating device for applying illuminating light to the interior of an organic body across the organic tissue of the body, an elongated insert portion adapted to be inserted into the body, and an image pickup device having a light-receiving portion provided on an end of the insert portion and capable of picking up the image of an object illuminated by the light transmitted through the tissue of the body. The illuminating device is adapted to emit illuminating light which has at least infrared rays, while the image pickup device is sensitive to infrared rays. The endoscope apparatus further has an exposure amount control device capable of controlling the amount of exposure of the object by the light emitted from the illuminating device and applied to the object through the tissue of the body, and the amount of exposure of the object by illuminating light from another illuminating device which is adapted for applying illuminating light to the object from the inside of the body.

Another object of the present invention is to provide an endoscope light source apparatus whereby a reflective illuminating light from inside a body and a transmissive illuminating light from outside the body can be fed to an endoscope, the entire apparatus can be made small and the operatability can be improved.

Another object of the present invention is to provide an endoscope light source apparatus whereby a reflective illuminating light from inside a body and a transmissive illuminating light from outside the body can be fed to an endoscope, the diagnosing activity can be improved and a proper reflected picture image and transmitted picture image can be observed.

A further another object of the present invention is to provide an endoscope light source apparatus whereby a reflective illuminating light from inside a body and a transmissive illuminating light from outside the body can be fed to an endoscope, the diagnosing activity can be improved, the transmissive illuminating light source and the living body can be electrically insulated from each other and safety can be improved.

The endoscope light source apparatus of the present invention is provided with a body inside illuminating light source feeding, from inside a body, an illuminating light on the position to be observed with an endoscope and a body inside illuminating device transmissively illuminating from outside the body the position to be observed with the endoscope. Also, preferably, the light source apparatus is further provide with an exposure controlling device controlling at least one of (a) the exposure to the body inside illuminating light emitted from the above mentioned body inside illuminating light source and (b) the exposure to the body outside illuminating light of the above mentioned body outside illuminating device. The above mentioned body outside illuminating device has a body outside illuminating light source arranged in the position opposed, for example, to the part observed with the endoscope through a living body from outside the body. The above mentioned body outside illuminating device has, for example, a body outside illuminating light source made integral with the above mentioned body inside illuminating light source and a light transmitting device transmitting the light emitted from this body outside illuminating light source to a predetermined position outside the body and emitting it.

These and other objects, features and advantages of the present invention will become clear from the following description of the preferred embodiments when the same is read in conjunction with the accompanying drawings.

BRIEF DESCRIPTION OF THE DRAWINGS

FIG. 8 is a sectional view of a probe portion of an endoscope used in the fifth embodiment of the endoscope apparatus;

FIG. 9 is an illustration of the sixth embodiment of the endoscope apparatus of the present invention;

FIG. 22A is a timing chart showing the timing of emission of light from an internal light source in the sixteenth embodiment of the invention;

FIG. 22B is a timing chart showing the timing of emission of light from an external light source in the sixteenth embodiment of the present invention:

FIG. 23 is an illustration of the manner in which the levels of light received from the external light source and the internal light source are changed;

FIG. 29 is a block diagram of a twenty-first embodiment of the endoscope apparatus of the present invention;

FIG. 30 is an illustration of a probe portion of an endoscope used in the twenty-first embodiment;

FIG. 36A is a timing chart illustrating the timing of rotation of the rotary filter;

FIG. 36B is a timing chart illustrating the output of a rotary filter encoder;

FIG. 36C is a timing chart illustrating the timing of emission of light from a strobe lamp;

FIG. 36D is a timing chart illustrating the operation of a solid-state image pickup device in the twenty-third embodiment;

FIG. 37 is a block diagram of a twenty-fourth embodiment of the endoscope apparatus of the present invention;

FIG. 38 is an illustration of a rotary filter in the twenty-fourth embodiment;

FIG. 39 is a block diagram of a synchronizing circuit;

FIG. 40A is a timing chart illustrating the timing of operation of a synchronizing circuit;

FIG. 40A is a timing chart illustrating the timing of rotation of the rotary filter;

FIG. 40B is a timing chart illustrating the timing of start pulse of a rotary filter encoder;

FIG. 40C is a timing chart showing the lead pulse of the rotary filter encoder;

FIG. 40D is a timing chart illustrating the output of a synchronizing circuit;

FIG. 40E is a timing chart illustrating the operation mode of a solid-state image pickup device;

FIG. 41A is a timing chart illustrating the operation mode of a solid-state image pickup device;

FIG. 41B is a timing chart illustrating the timing of emission of light from an internal light source in the twenty-fourth embodiment;

FIG. 41C is a timing chart illustrating the timing of emission of light from an external light source in the twenty-fourth embodiment;

FIG. 48A is a timing chart illustrating the operation of a solid-state image pickup device incorporated in the twenty-ninth embodiment;

FIG. 48B is a timing chart illustrating the timing of a flash signal in the twenty-ninth embodiment;

FIG. 48C is a timing chart illustrating the timing of an image displayed on a monitor device in the twenty-ninth embodiment;

FIG. 48D is a timing chart illustrating the timing of emission of light from an external light source in the twenty-ninth embodiment;

FIG. 48E is a timing chart illustrating a change in the change in the light from an internal light source in the twenty-ninth embodiment;

FIG. 48F is a timing chart illustrating the timing of switching of operation for writing information in a memory used in the twenty-ninth embodiment; and FIG. 48G is a timing chart illustrating the timing of switching of operation for reading information from the memory.

FIGS. 49 to 53 relate to the thirtieth embodiment of the present invention.

FIG. 49 is a block diagram showing the formation of a light source apparatus.

FIG. 50 is an explanatory view showing the formation of an electronic scope.

FIG. 51 (A) is an explanatory view showing the formation of a fiber scope.

FIG. 51 (B) is an explanatory view showing the formation of an externally fitted television camera.

FIG. 52 is an explanatory view showing the formation of a fiber scope fitted with a tip camera.

FIG. 53 is a block diagram showing the formation of a light source apparatus of a modification of the thirtieth embodiment.

FIG. 56 is an explanatory view showing essential parts of a light source apparatus.

FIG. 57 is an explanatory view showing a rotary filter.

DETAILED DESCRIPTION OF THE PREFERRED EMBODIMENTS

Figure 1:
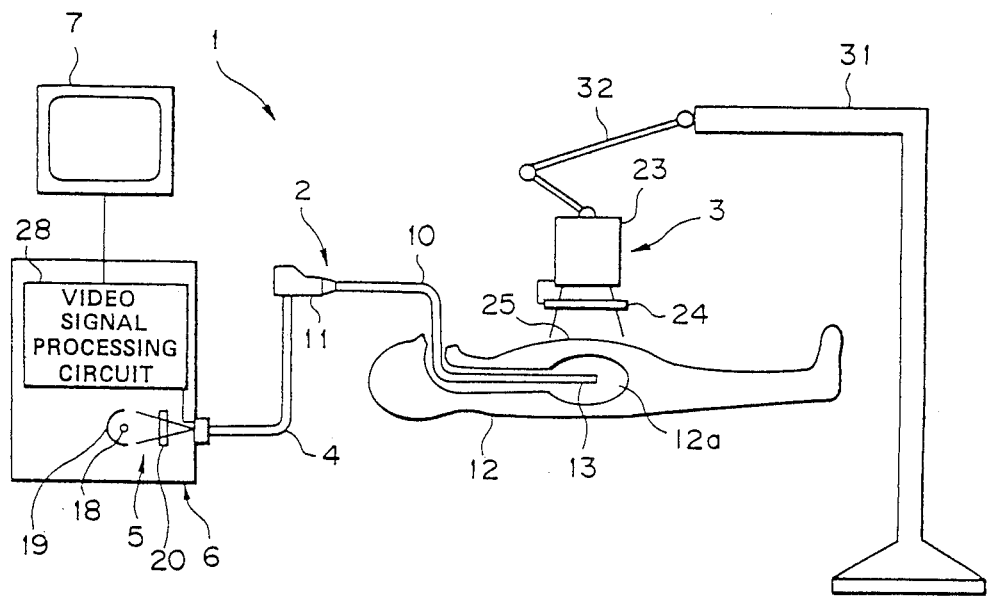
FIG. 1 is a schematic illustration of the first embodiment of the endoscope apparatus in accordance with the present invention.
Figure 2:
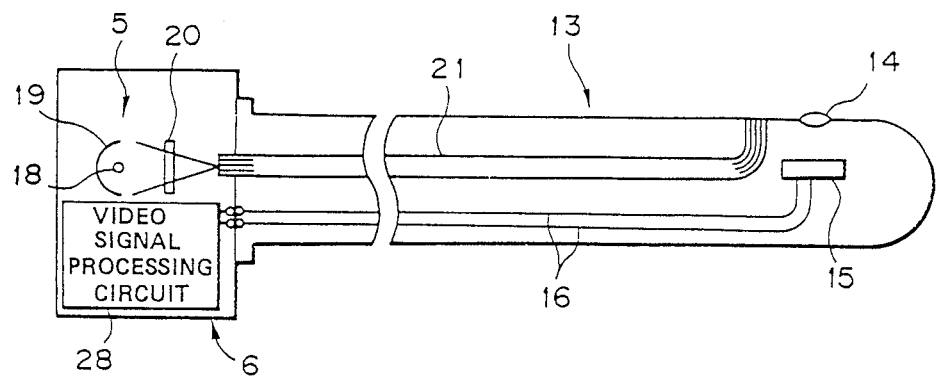
FIG. 2 is an illustration of a probe portion of an electronic endoscope in the endoscope apparatus shown in FIG. 1.

FIGS. 1 and 2 illustrate the first embodiment of the endoscope apparatus in accordance with the present invention. As will be understood from FIG. 1, the first embodiment of the endoscope apparatus, generally denoted by 1, has an electronic endoscope 2, an external light source 3 for externally applying an illumination light from the exterior of an organism such that the electronic endoscope 2 receives light from the external light source 3 through the organism, a controller 6 connected to the electronic endoscope 2 through a cable 4 and having a video signal processing circuit 28 and a light source device 5 for internally illuminating the organism, and a monitor 7 as display means connected to the controller 6.

The electronic endoscope 2 has an elongated insert portion 10 and a large-diameter manipulating portion 11 of a large diameter connected to the rear end of the insert portion 10. The insert portion 10 may be flexible or rigid, and is adapted to be inserted into a body cavity 12a of a human body 12 through, for example, the mouth. As will be seen from FIG. 2, a probe portion 13 on the free end of the insert portion 10 has an image-forming optical system 14 such as of an objective lens system. A solid-state image pickup device 15 such as a CCD is provided on the imaging position of the image-forming optical system 14. The solid-state image pickup device 15 is sensitive at least to infrared rays. The output from the solid-state image pickup device 15 is input to the video signal processing device 28 in the controller 6, through a signal line 16 which extends through the insert portion 10 and the cable 4, so as to be converted into a video signal. The thus obtained video signal is input to the monitor device 7 so that the image of the object to be observed is displayed on the monitor device 7.

The internal light source device 5 of the controller 6 has a light source 18 which emits a light. The light from the light source 18 is collected by a reflective mirror 19 and is introduced through a filter 20 into a light guide 21 which is made of a flexible fiber bundle. The light guide 1 is inserted into the cable 4 and the insert portion 10, so that the illuminating light impinging upon the light guide 21 is emitted from the probe portion 13 on the end of the light guide 21, thereby illuminating the object.

The light source 18 may be a xenon lamp, a halogen lamp or a strobe lamp. The light emitted from the light source 18 may have wavelength range which may spread over one, two or all of ultraviolet range, visible range and infrared range. The infrared filter 20 is selected in accordance with the wavelength range of the light used in the observation. For instance, the infrared cut-off filter is used.

The external light source device 3 has a light source 23 the light from which is applied through a filter 24 onto the surface 25 of a human body 12. The light is transmitted through the human body 12 so that an image of an organic tissue is formed by the light transmitted through the human body 12. This image will be referred to as "transmitted light image, hereinunder". The thus formed transmitted light image is picked up by the image pickup device 15 of the electron endoscope 2.

The light source 23 may be a xenon lamp, a halogen lamp or a strobe lamp, and the light emitted therefrom should have at least an infrared component. The filter 24 should be capable of transmitting at least lights of infrared wavelength region. For instance, the filter 24 may be an infrared transmitting filter, a filter capable of transmitting lights of infrared wavelength region and a portion of visible region, a filter capable of transmitting only specific portion of infrared wavelength region, or a filter which is capable of transmitting the infrared rays of 700 to 1000 nm while cutting off heat-generating infrared component of wavelengths longer than 1000 nm. The type of the filter is selected in accordance with the wavelength of the light used in the observation.

The external light source device 3 is, for example, suspended from a stand 31 through a universal arm 32 so that its position is adjustable with respect to the human body 12.

According to this arrangement, the illuminating light of, for example, visible wavelength range emitted from the internal illuminating light source device 5 and transmitted through the filter 20 is applied from the end of the light guide 21 onto the objective portion in a body cavity 12a. The light reflected from the object is received by the solid-state image pickup device 15 through the image-forming optical system, whereby the image of the surface of the object is formed by, for example, the visible ray. This image will be referred to as "reflected light image", hereinafter.

On the other hand, the illuminating light emitted form the external light source 3 having at least infrared component is applied to the surface 25 of the human body and reaches the interior of the body cavity 12a, through the organic cavity. The transmitted light image of the organic tissue formed by the external light transmitted through the organic tissue is photographed by the solid-state image pickup device 15 which is sensitive at least to the infrared rays.

The reflected light image obtained through the internal illumination and the projected light image formed by the external illumination may be observed simultaneously or, alternatively, only one of the external and internal illumination is turned on so as to enable the user to observe either one of these two types of image.

As will be understood from the foregoing description, in the described embodiment, the light from the exterior of the human body contains at least an infrared component which can easily be transmitted through organic tissue. The transmission of the infrared component of the external light is so large that the interior of the tissue can easily be observed by picking up the image formed by the transmitted infrared component of the external illuminating light.

When infrared rays are used as the external illuminating light, the size, weight and the power consumption of the light source 23 of the external light source device 3 can be reduced advantageously.

The use of infrared rays offers another advantage in that the state of blood vessels or tumour in membrana can easily be observed as compared with the a case where ordinary visible rays are used, through observation of amount of blood or existence of blood, by making use of a fact that hemoglobin in the blood absorbs the infrared rays contained by the transmitted light from the external light source.

Figure 3:
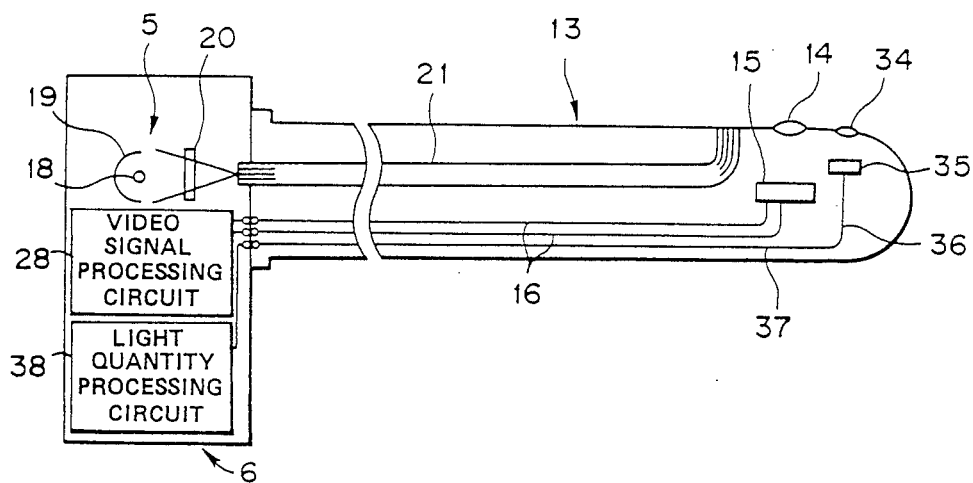
FIG. 3 is an illustration of an electronic endoscope incorporated in the second embodiment of the endoscope apparatus of the present invention.

FIG. 3 shows a second embodiment of the endoscope apparatus in accordance with the present invention.

This embodiment has a condenser lens 34 provided on the end 13 of the insert portion 10, and an infrared sensor element 35 provided on the focusing end of the condenser lens 34. The output signal of the infrared sensor element 35 is connected to the controller 6 through a signal line 36 which extends in the insert portion 10 and the cable 4. The controller 6 has a light-quantity detecting circuit 38 which is capable of detecting the quantity of the infrared rays impinging upon the infrared sensor element 35.

In the described embodiment of the present invention, it is possible to detect the positional relationship between the external light source device 3 and the object, by sensing the quantity of the infrared rays received by the infrared sensor element 35. Thus, an efficient illumination can be achieved by adjusting the positions of the probe portion 13 and the external light source device 3 so as to maximize the quantity of the infrared rays received by the infrared sensor element.

Figure 4:
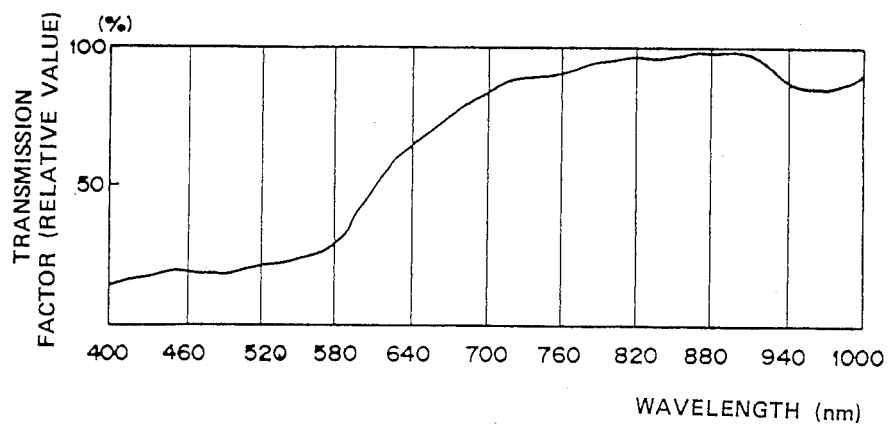
FIG. 4 is an illustration of a spectral light transmitting characteristic of an organic tissue, for explaining the third embodiment of the endoscope apparatus of the present invention.

A fourth embodiment of the invention will be described with reference to FIG. 4.

The third embodiment is substantially the same as the first and the second embodiments except that the filter 24 is capable of transmitting red and near-infrared rays of wavelengths not lower than 600 nm. Thus, the light externally applied to the body to be examined is red and near-infrared rays of wavelengths not lower than 600 nm.

As will be seen from this figure, organic tissue in general exhibits a specifically high transmission in the wavelength region above about 600 nm. In addition, color elements in the human body such as hemoglobin in general exhibits a high transmission in the wavelength region above about 600 nm. Therefore, the observation of the object by the external illuminating light is much facilitated as compared with the case where ordinary visible rays are used. Thus, the fourth embodiment requires only that the external illuminating light has a wavelength region which is not lower than about 600 nm. Thus, the external illuminating light may be visible red rays of wavelengths ranging between, for example, 600 and 780 nm or between 600 and 700. Other structural features, operation and effects of the third embodiment are materially the same as those of the first and the second embodiments.

Figure 5:
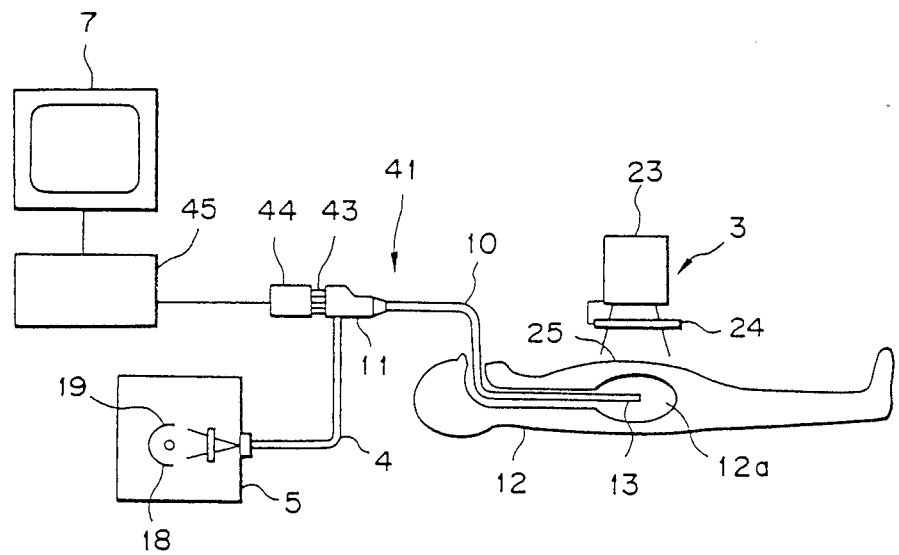
FIG. 5 is an illustration of the fourth embodiment of the endoscope apparatus of the present invention.
Figure 6:
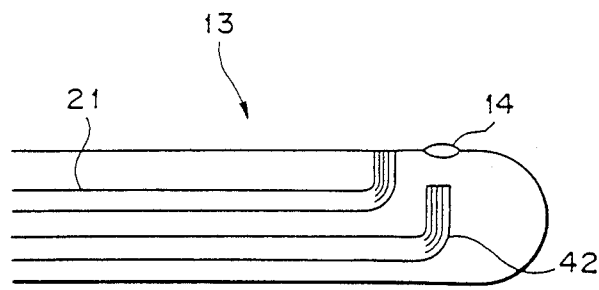
FIG. 6 is an illustration of the probe portion of an endoscope incorporated in the fourth embodiment.

FIG. 5 and 6 in combination show a fourth embodiment of the present invention. In this embodiment, an image guide 42 formed of a flexible fiber bundle is extended through the insert portion 10 of the endoscope 41. The image guide 42 has an end which is located at the imaging position of the image-forming optical system 14 which is provided on the probe portion 13. The image formed on the end surface of the image guide 42 is introduced through the image guide 42 to the manipulating portion 11 so as to be observed through an ocular portion 43 having, for example, an ocular lens provided on the rear end of the manipulating portion 11.

A television camera 44, sensitive at least to infrared rays, is connected as an image pickup device to the ocular portion 43. The television camera produces an output which is delivered to a video signal processing device 45 so as to be changed into a video signal. The video signal is then input to the monitor device 7 whereby the image is observed through the monitor 7. When the insert portion 10 is rigid, the a relay lens system or a similar rigid image transmitting means may be used in place of the fiber bundle used in this embodiment. Other portions are materially the same as the first embodiment.

In operation of the fourth embodiment, the reflected light image formed by the internal illumination light emitted from the light source device 5, as well as the projected light image of an organic tissue formed by the light externally applied and transmitted through the tissue, is formed on the end surface of the image guide 42. The thus formed image is transmitted through the image guide 42 to the manipulating portion 11 and is picked up by the television camera 44 so as to be displayed on the monitor 7.

Obviously, the user can observe the image by naked eye through the ocular portion 43, provided that the light is of visible wavelength range.

Other effects and advantages are the same as those derived from the first embodiment.

Figure 7:
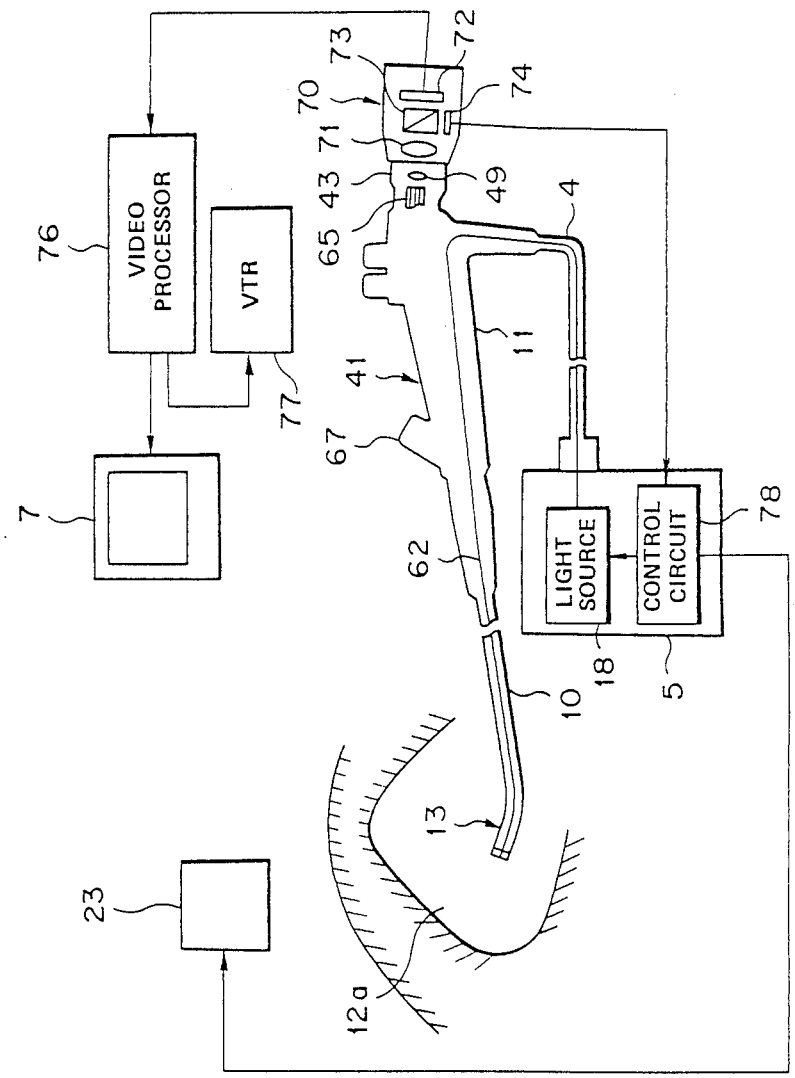
FIG. 7 is a schematic illustration of the fifth embodiment of the endoscope apparatus of the present invention.

FIGS. 7 and 8 show a fifth embodiment of the present invention. As in the case of the fourth embodiment, the fifth embodiment features a television camera 70 connected to the ocular portion 43 of a fiber scope 41. The fiber scope 41 is provided with a probe portion 13 the construction of which is shown in FIG. 8. As will be seen from this figure, the probe portion 13 is provided with an instrument channel 61 through which an instrument necessary for an operation to be conducted on the organic tissue is to be inserted, a light guide 62 for illuminating the organic tissue from the interior of the body, a light distribution lens 63 provided on the end of the light guide 62, an objective lens system 64 for forming an optical image of the object, an image guide 65 for transmitting the optical image to the ocular portion 43, and a nozzle 66 for washing any contaminant attaching to the objective lens system 64.

The instrument channel 61 communicates with an instrument inlet 67 provided in the manipulating portion 11. The light guide 62 is extended through the insert portion 12, manipulating portion 11 and the cable 4 to the ocular portion 43 so as to be observed through the latter. The nozzle 66 is provided with an air-water supply channel 68 extended through the insert portion 12.

The television camera 70 mentioned before includes an image-forming lens 71 through which the light from the ocular portion 43 is collected to form an optical image, a solid-state image pickup device 72 positioned at the imaging position of the image-forming lens 71 so as to effect a photoelectric conversion so as to form a video signal, a prism disposed between the image-forming lens 71 and the solid-state image pickup device 72 and adapted for splitting the path of light into two paths, and a light-receiving element 74 disposed on the path of light formed by the prism 73 and adapted for detecting the level of exposure on the solid-state image pickup device 72.

The output from the solid-state image pickup device 72 is input to a video processor 76 which conducts necessary signal processing operations such as wave shaping, γ correction, white balancing and so forth. The video signal output from the video processor 76 is input to the monitor device 7 to enable the image to be observed. It is also possible to arrange such that the video signal from the video processor 76 is input to a video tape recorder (VTR) 77 so as to be recorded as required.

On the other hand, the output signal from the light-receiving element 74 is input to a control circuit 78 provided in the light source device 6. The control circuit 78 is adapted for controlling the quantity of light emitted from the light source 23 for external illumination, as well as the quantity of light from the light source 18 for internal illumination, in accordance with the output from the light-receiving element 74.

In this embodiment, the level of exposure on the solid-state image pickup element 72 is detected by the light-receiving element 74 in the television camera 70, and the quantities of the lights from the light source 18 for external illumination and the light source 23 for internal illumination are controlled in accordance with the output from the light-receiving element. For instance, it is possible to control such that the quantity of light received by the solid-state image pickup device 72 is maintained substantially constant. Other structural features and operation and advantages are the same as those of the fourth embodiment.

FIG. 9 shows a sixth embodiment of the present invention. This embodiment features a still camera connected to the ocular portion 43 of a fiber scope 41 which is similar to that used in the fifth embodiment. The still camera 80 has an image-forming lens 81 for collecting light from the ocular portion 43 so as to form am optical image, a film 82 disposed on the imaging plane of the image-forming lens 80 and adapted for recording the optical image, a prism 83 disposed between the image-forming lens 81 and the film 82 and adapted for splitting the path of light into two light paths, and a light-receiving element 84 disposed on the optical path provided on one of the light paths and capable of detecting the level of exposure on the film 827. The film 82 may be sensitive both to visible and infrared rays or only to visible rays. It is also possible to selectively use one of a film sensitive to infrared rays and a film sensitive to visible rays.

The output signal from the light-receiving element 84 is input to a control circuit 78 provided in the light source device 6. The control circuit 78 is capable of controlling the quantities of lights from the light source 18 and the light source 23 for the external and internal illumination. In the illustrated embodiment, the light-receiving element 84 is connected at the ocular portion 43 of the fiber scope 41 to a signal line 86 which extends from the ocular portion 43 of the fiber scope 41 to the connector of the cable 4. The signal line 78 extends to the aforementioned control circuit 78. Thus, the light-receiving element 84 is connected through the signal line 86 to the control circuit 78.

According to this embodiment, it is possible to easily photograph the transmitted light image of the tissue through which the externally applied light has been transmitted.

Other structural features, effects and advantages are the same as those of the fifth embodiment.

Figure 10:
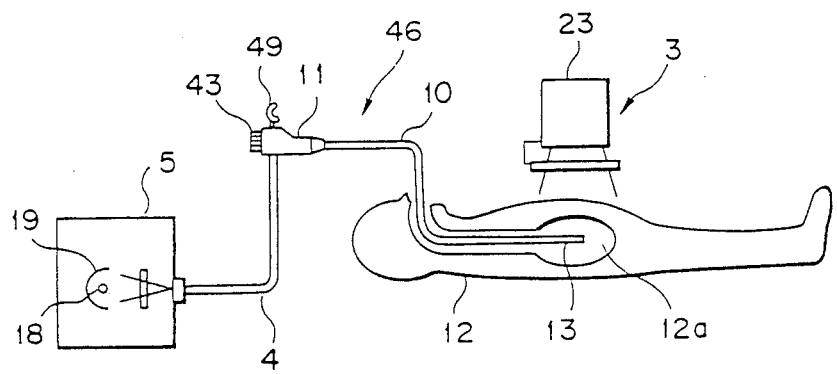
FIG. 10 is an illustration of an endoscope used in a seventh embodiment of the present invention.
Figure 11:
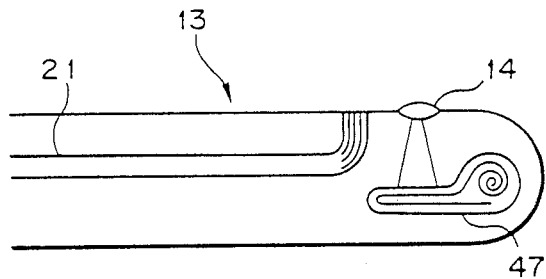
FIG. 11 is an illustration of a probe portion of the endoscope.

FIGS. 10 and 11 show a seventh embodiment of the present invention. As will be seen from FIG. 11, the seventh embodiment has a film 47 sensitive at least to infrared rays, e.g., an infrared film, disposed at the imaging position of the image-forming optical system 14 on the probe portion 13 of the endoscope. The film 47 serves as image pickup means on which the observed image is recorded. The manipulating portion 11 of the endoscope 46 has a release lever 49 capable of operating a shutter mechanism.

As will be seen from FIG. 10, the endoscope 46 may be designed such as to enable the image transmitted by the image-forming optical system and the image guide to be observed through the ocular portion 43, or such as to enable the image only to be recorded on the film 47.

Other structural features, operation and effects are the same as those of the first embodiment.

Figure 12:
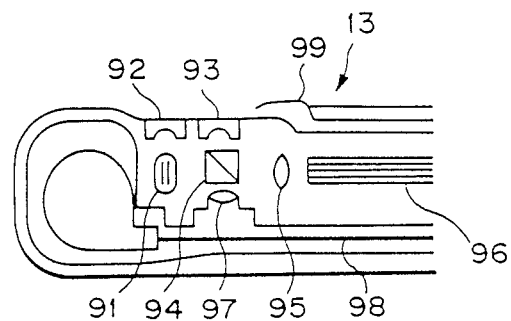
FIG. 12 is an illustration of a probe portion of an endoscope used in an eighth embodiment of the present invention.

FIG. 12 shows an eighth embodiment of the present invention.

This embodiment is designed to enable the image of the object to be recorded on a film disposed in the probe portion 13 of the endoscope, as in the case of the seventh embodiment.

More specifically, the probe portion 13 of the endoscope incorporated in the eighth embodiment has a lamp 91 for illuminating an organic tissue from the interior of a body cavity, a lens 92 for diffusing this light so as to illuminate the organic tissue, a lens 93 for condensing the internal illuminating light reflected by the organic tissue and the light transmitted from the external light source 23 through the organic tissue as the observation object, and a prism 94 for splitting the path of light from the lens 93. An image-forming lens 95 is provided on one of the light paths formed by the prism 94, and the end surface of the image guide 96 received in the insert portion 10 is disposed at the imaging position of the image-forming lens 95. The image guide 96 is extended to an ocular portion (not shown) so as to transmit the object image to the latter.

An image-forming lens 97 is disposed on the other light path formed by the prism 94. A film 98 for recording the object image is positioned at the position where the image-forming lens 97 forms the image.

A nozzle 99 provided in the probe portion 13 is directed towards the above-mentioned lenses 92 and 93. The nozzle 99 is connected to the air-water supply channel formed in the insert portion 10. In operation, washing water is jetted from the nozzle 99 so as to wash away any contaminant attaching to the surfaces of the lenses 92 and 93.

Other structural features, operation and advantages are the same as those of the first embodiment.

Figure 13:
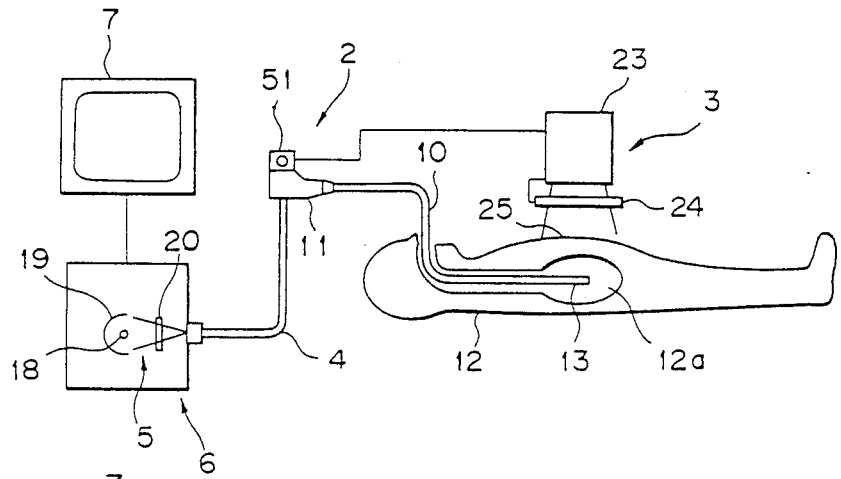
FIG. 13 is an illustration of a ninth embodiment of the endoscope apparatus of the present invention.

FIG. 13 shows a ninth embodiment of the present invention.

The ninth embodiment features a light-quantity control means 51 provided on or in the vicinity of the manipulating portion 11 of the electron endoscope 2 and adapted for controlling the quantity of light emitted from the external light source device 3. Other portions are materially the same as those of the first embodiment.

As explained before, the factor of transmission of the light from the external light source varies according to the position of the object to be observed. Therefore, the quantity of the light received by the endoscope through the tissue of the object varies even if the quantity of light emitted from the light source 23 is maintained constant, making it difficult to observe the transmitted light image formed by the light which has been transmitted through the object tissue. This problem, however, is eliminated because the quantity of light emitted from the light source 23 can be controlled in accordance with the change in the position of the object, such as to maintain a substantially constant quantity of light received by the solid-state image pickup device 15 regardless of the position of the object.

Obviously, the electron endoscope 2 used in this embodiment may be substituted by a television camera or a still camera connected to an ocular portion 43 of the fiber scope 41 of the fourth to sixth embodiment, or by an endoscope provided with a film in the probe portion 13 as in the seventh and eighth embodiments.

Figure 14:
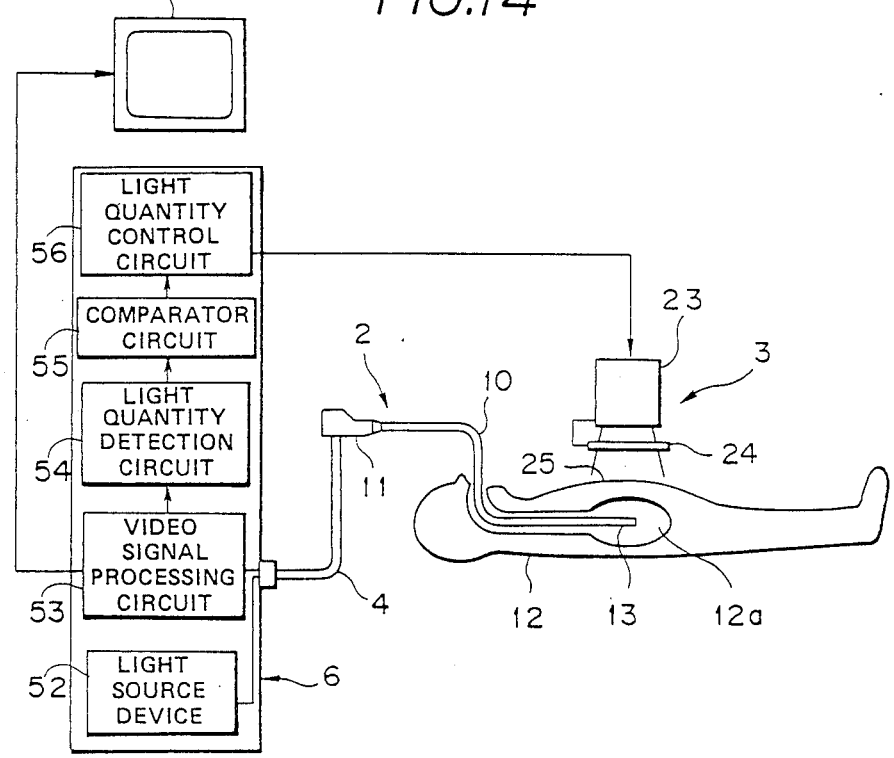
FIG. 14 is an illustration of a tenth embodiment of the endoscope apparatus of the present invention.

FIG. 14 illustrates a tenth embodiment of the present invention. In this embodiment, a light quantity detecting circuit 54 is provided in the controller 6 in addition to the light source 52 for internal illumination and the video signal processing circuit 53. This light quantity detection circuit 54 is adapted to detect the quantity of the light in the field of vision of the electronic endoscope 2, from the output of the video signal processing circuit 53. The light quantity detected by the light quantity detecting circuit 54 is compared by a comparator circuit 55 with a predetermined value, and the quantity of light emitted from the light source 23 of the external light source device 3 is controlled in accordance with the output from the comparator 55 such that the light quantity in the field of vision of the electronic endoscope 2 is maintained substantially constant.

Other portions are materially the same as those of the first embodiment.

In the embodiment, it is possible to automatically maintain the quantity of light incident to the solid-state image pickup device 15 substantially constant. For instance, when only the external illumination is used, the quantity of the infrared rays applied by the external light source device can be maintained substantially constant.

Obviously, the electron endoscope 2 used in this embodiment may be substituted by a television camera or a still camera connected to an ocular portion 43 of the fiber scope 41 of the fourth to sixth embodiment, or by an endoscope provided with a film in the probe portion 13 as in the seventh and eighth embodiments.

Figure 15:
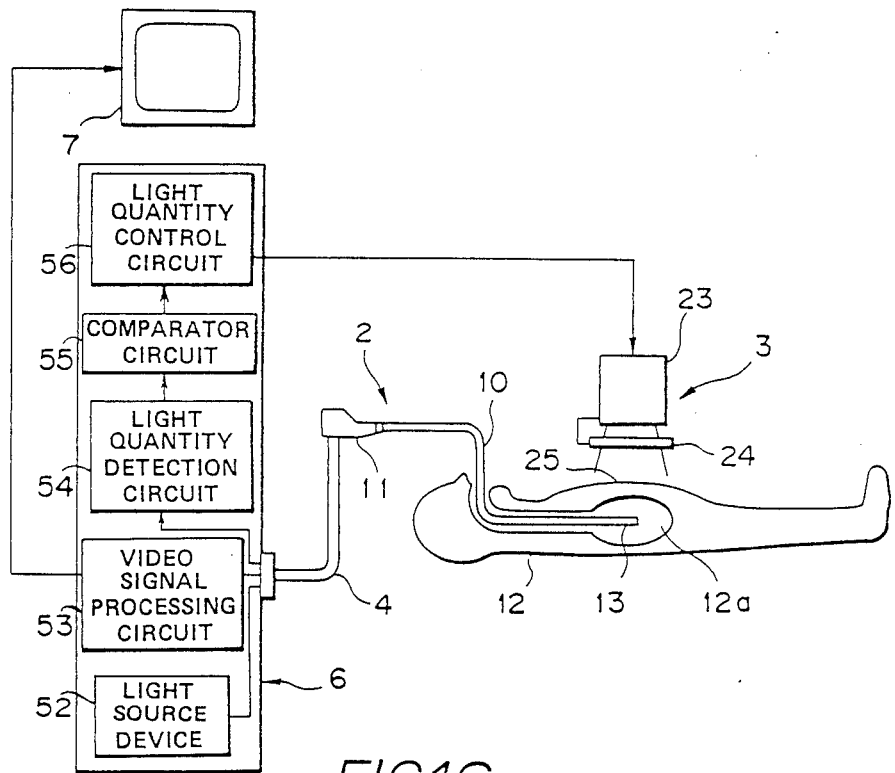
FIG. 15 is an illustration of an eleventh embodiment of the endoscope apparatus of the present invention.

FIG. 15 shows an eleventh embodiment of the present invention. This embodiment incorporates, as in the case of the second embodiment shown in FIG. 3, an infrared sensing element 35 provided in the probe portion 13. The output from the infrared sensing element 35 is input to the light quantity detection circuit 54 so that the quantity of light emitted from the light source 23 is controlled in accordance with the quantity of the infrared rays received by the infrared sensing element 35. Other portions are materially the same as those in the tenth embodiment.

According to this embodiment, assuming here that filters 20 and 24 are so selected that the visible rays and infrared rays are used as the external and internal illuminating lights, it is possible to maintain the quantity of the external illuminating light independently of the internal illuminating light. Conversely, the arrangement may be such that the infrared rays are used for the internal illumination while visible rays are used for external illumination. In such a case, the quantity of the external illumination light can be controlled through detection of the quantity of the visible rays.

Figure 16:
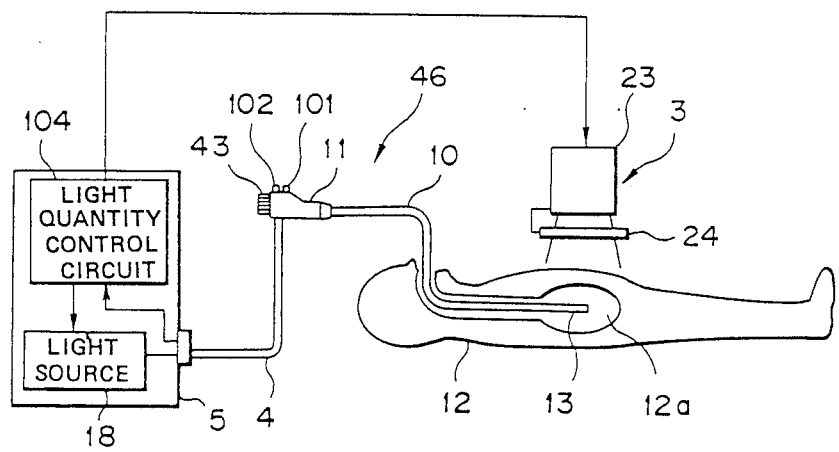
FIG. 16 is an illustration of a twelfth embodiment of the endoscope apparatus of the present invention.

FIG. 16 is an illustration of a twelfth embodiment of the present invention. As in the case of the seventh embodiment, the twelfth embodiment employs a film provided on the probe portion 13 of the endoscope 46 so as to be able to record the image of the object.

In this embodiment, a pair of release buttons 101, 102 are provided on the manipulating portion 11 of the endoscope 46. The light source device 5 has a light-quantity control circuit 104 which is capable of controlling the quantity of light from the light source 18 for the internal illumination and also controlling the quantity of flash light from the external illumination light source 23. The light quantity control circuit 104 is adapted for receiving a release signal input from the release button 102.

As one 101 of the two release buttons is pressed, the object image in the instant state of illumination is photographed. However, when the other release button 102 is pressed, the release signal from this release button is input to the light quantity control circuit 104 so that the latter controls the light source 23 for the external illumination so as to cause the latter to flash, thereby allowing the object to be photographed under optimum condition of illumination.

According to this embodiment, the light source 23 for the external illumination is made to flash as required, whereby an image is easily obtained in which the ratio of the transmitted light image is increased.

Other structural features, operation and effects are the same as those of the seventh embodiment.

Figure 17:
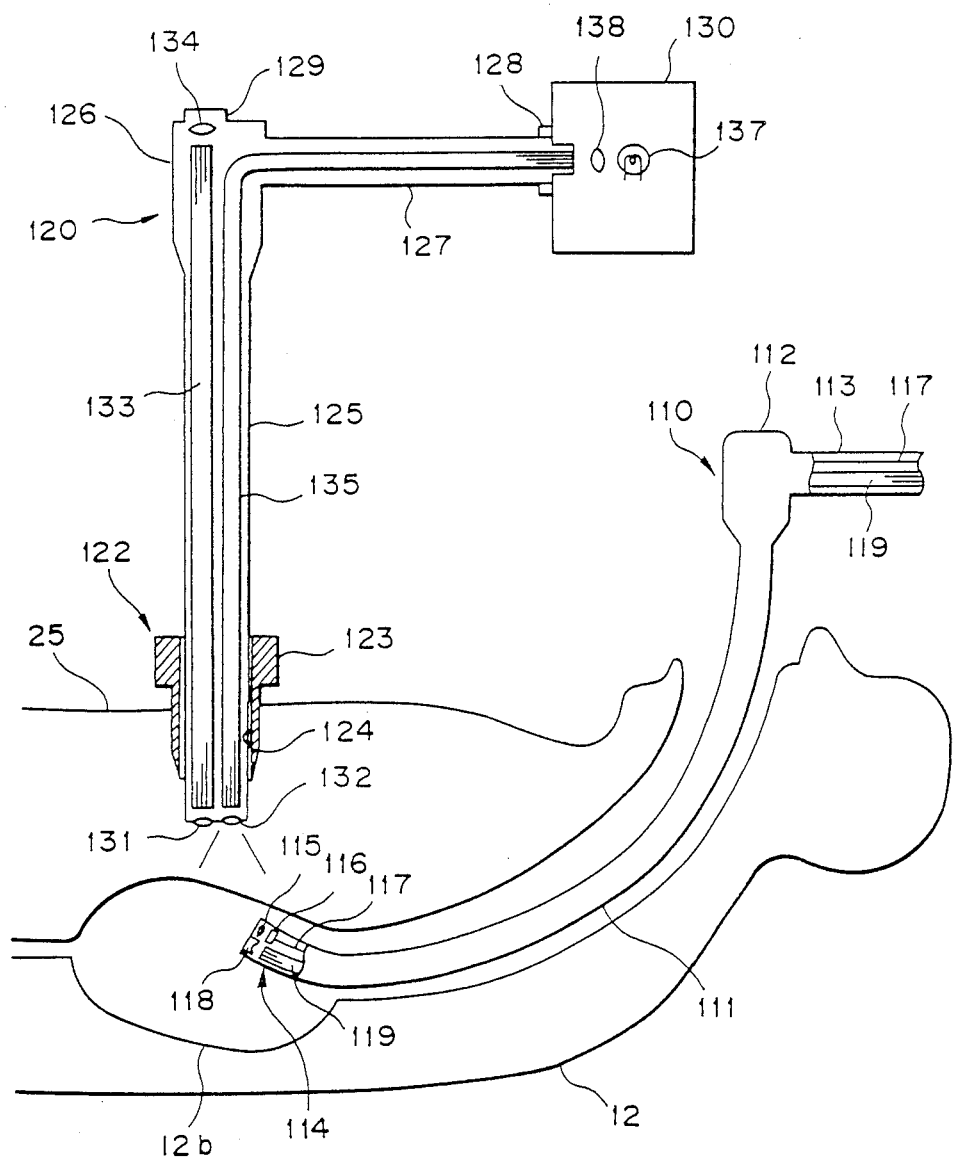
FIG. 17 is an illustration of the thirteenth embodiment of the endoscope apparatus of the present invention.

FIG. 17 shows a thirteenth embodiment of the present invention. The thirteenth embodiment is characterized in that the an organic tissue is illuminated from the interior of a body cavity for the purpose of production of a transmitted light image.

As will be seen from FIG. 17, this embodiment employs a first endoscope 110 which is inserted into the human body 12 for the purpose of observation of an organ 12b in the body cavity, and a second endoscope 120 which applies illumination light to the organ and observes the same from the exterior.

The first endoscope 110 has, as in the case of the endoscope 2 used in the first embodiment, an elongated flexible insert portion 111, a manipulating portion 112 connected to the rear side of the insert portion 111, and a universal cord 113 extended from the manipulating portion 112 and connected to a controller 6 which may be the same as that shown in FIG. 1. The insert portion 11 has an end probe portion 114 which is provided with an image-forming optical system 115, and a solid-state image pickup device 116 which is disposed at the imaging position of the image-forming optical system 115 and sensitive both to visible rays and infrared rays. A signal line 117, which is connected at its outer end to the solid-state image pickup device 116, extends through the insert portion 111, manipulating portion 112 and the universal cord 113, and is connected at its other end to the video signal processing circuit 28 in the controller 6. The probe portion 114 has a light distribution lens 118 to the rear side of which is connected a light guide 119 which extends through the insert portion 111, manipulating portion 112 and the universal cord 113 so as to be connected to the light source 5 in the controller 6.

On the other hand, the surface 25 of the body is pierced and penetrated by a medical tube 122 such as TROCAR adapted to be inserted into a body cavity. The medical tube 122 has a TROCAR sheath tube 123 having a through bore 124 through which the aforementioned second endoscope 120 is inserted. This second endoscope has, for example, a flexible insert portion 125, a manipulating portion 126 connected to the rear end of the insert portion 125, and a light guide table 127 extending from the manipulating portion 127. The light guide cable 127 is provided at the front end thereof with a connector 128 which is adapted to be detachably connected to a receptacle on a light source unit 130. The manipulating portion 126 is provided on the rear end thereof with an ocular portion 129. The insert portion 125 is provided on the front end thereof with an objective lens 131 and a light distributing lens 132. The front end surface of the image guide 133 is positioned on the imaging position of the objective lens 131. The image guide 133 is extended through the insert portion 125 and is extended to the ocular portion 129. The ocular portion 129 has an ocular lens 134 which opposes the rear end surface of the image guide 13, so that the user can observe the image transmitted through the image guide, by way of the ocular lens 134 on the ocular portion 129. A light guide 135, which is connected to the rear end of the light-distribution lens 132, is extended through the insert portion 125, manipulating portion 126 and the light guide cable 127, so as to be connected to the connector 128. The aforementioned light source unit 130 has a lamp 137 the light from which is condensed by the condenser lens 138 so as to impinge upon the incident end of the light guide 135. The lamp 137 is capable of emitting light containing infrared region. The end of the insert portion 125 of the second endoscope 120 is provided with a flexing portion which can flex in accordance with the operation of a flexure manipulator (not shown) provided on the manipulating portion 126. This flexing portion enables the position of the end of the insert portion 125 to be varied freely, thereby allowing any desired portion of the object to be illuminated. In the described embodiment, the second endoscope 120 is inserted into the body cavity through the through bore 124 in the TROCAR sheath tube 123 of a medical tube 122. The illuminating light emitted from the lamp 137 of the light source unit 130 is emitted from the end of the insert portion 125, past the connector 128, light guide 135 and the light-distributing lens 132 of the second endoscope, so as to externally illuminate the objective organ in the body cavity. This illuminating light contains at least infrared component as explained before. The transmitted light image of the organic tissue, formed by this illuminating light transmitted through the tissue, is picked up by the solid-state image pickup device 116 of the first endoscope, so as to be displayed on a monitor device which is not shown. It has been reported that infrared rays have a high transmissivity through membrana tissues and are highly absorbable by blood flowing in blood vessels. Therefore, the state of blood vessels can be minutely observed through the first endoscope 110, while illuminating the object by the second endoscope 120.

In addition, this embodiment provides a higher quality of the transmitted image because the illuminating light can be applied to the objective part from a position which is sufficiently close to the objective part.

Needless to say, the described embodiment can be used such that the reflected light image of the object, illuminated by the light from the first endoscope 110, is observed through the first endoscope 110.

The second endoscope 120 which illuminates the organ in the body cavity from the exterior of the organ maybe a flexible endoscope having a flexible insert portion, or may be a rigid optical endoscope having a rigid insert portion.

In the described embodiment of the invention, the second endoscope has an observation means for enabling the user to observe the object, constituted by the image guide 133 for transmitting the image to the ocular portion 129. This, however, is only illustrative and the arrangement may be such that a solid-state image pickup device is provided in the probe portion or the manipulating portion of the endoscope. The first endoscope 110, which is used for observation of the transmitted light image formed by the light applied from the exterior of the organ, may be a fiber scope although an electronic endoscope is used as the first endoscope 110 in this embodiment.

Furthermore, the second endoscope may be substituted by a simple light-conducting member such as an optical rod or a light guide fiber adapted to be inserted into the body cavity so as to illuminate the object.

The image pickup device used in the first to thirteenth embodiments may be designed to produce a color image, by surface sequence system which sequentially changes the illuminating light between R(red), G (green) and B (blue) or R, W (white) and B, or by a simultaneous color image forming system which employs a color filter disposed on the front side of the solid-state image pickup device. The image pickup device also may be a combination of a television camera and an infrared film. It is also to be understood that the light source device 5 for the internal illumination and the light guide may be omitted from this embodiment.

Figure 18:
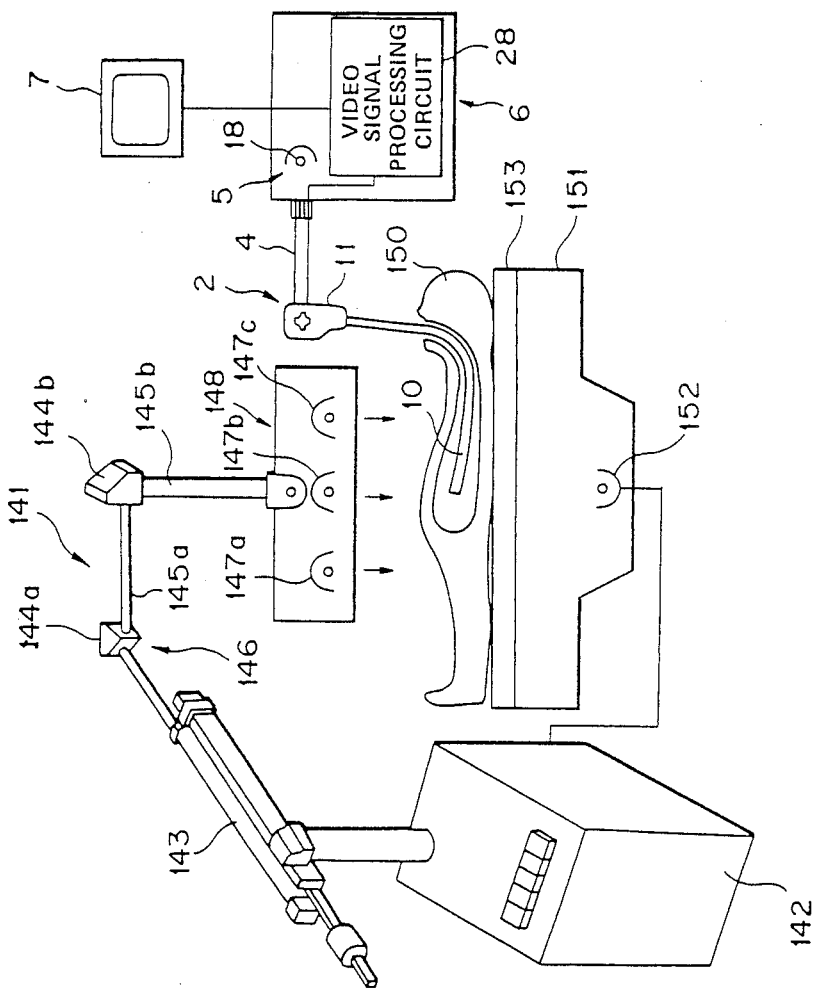
FIG. 18 is an illustration of the fourteenth embodiment of the endoscope apparatus of the present invention.

FIG. 18 shows a fourteenth embodiment of the present invention.

This embodiment of the endoscope apparatus has an external illuminating device 141 for illuminating the interior of a body from the exterior of the same. This external illuminating device 141 has a control portion 142, an expandable mechanism 143 connected to the control portion 142, a light source shifting device 146 connected to the expandable mechanism 143 and provided with a plurality of articulates 144a, 144b and arms 145a, 145b connected to the articulates, and a light source 148 provided on the end of the light source shifting device 146 and provided with a plurality of illuminating lamps 147a, 147b and 147c. The light source 148 is electrically connected to the control portion 142.

During the examination, the patient 150 lies on a bed 151 which is provided on the bottom thereof with an illuminating lamp 152 directed upward. The portion of the top surface of the bed 151 opposing to the lamp 152 is made of a light-transmitting member 153 capable of transmitting light from the lamp 152. The illuminating lamp 152 is electrically connected to the control portion 142. The control portion 142 is designed for controlling the quantities of light emitted from the lamps 147a, 147b and 147c of the light source 148, as well as the on-off states of these lamps, and also the light quantity and state of the lamp 152.

When the examination is conducted, the patient 150 lies on the bed 151 prone or supine according to the condition of the examination, and the insert portion 10 of the of the electronic endoscope 2 used in the first embodiment is inserted into the body cavity. The electronic endoscope 2 is connected to the controller 6 which is provided with the video signal processing circuit 28 and the light source device 5.

Other portions are materially the same as the first embodiment. In this embodiment, the light source 148 and the lamp 152 of the external illuminating device 141 are controlled by the control portion 142. The lights emitted from the lamps 147a, 147b and 147c of the light source 148 permeate through the patient's body so that a transmitted light image of, for example, blood vessels under the membrana of an organ is formed on the solid-state image pickup device 15 by the image-forming optical system 14 on the end of the endoscope 2, and is photographed.

The output from the solid-state image pickup device 15 is processed by a video signal processing circuit 28 in the controller 6 so that the transmitted light image is formed on the monitor device 7.

As to the observation of the transmitted light image, it is preferred that the illuminating light is applied in the direction which efficiently provides an image optimum for the diagnosis. To this end, the user can suitably operate the expandable mechanism 143 and the light source shifting means 146 which are provided between the control portion 142 and the light source 148, thereby illuminating the object in the interior of the body and to observe the same in an optimum angle. When the patient 150 is lying supine and, hence, illumination from the back is necessary, the illumination lamp 152 provided on the bottom of the bed 151 is turned on so that the light from the lamp 152 permeates through the light transmitting member 153 on the top of the bed 151 so as to illuminate the interior of the body.

When it is desired to illuminate the interior of the body from the exterior of the same by means of the external illuminating device 141, the distance and/or angle of the illumination can be varied as desired. The control of the quantity of the illuminating light can be effected by controlling the number of lamps operating in the light source device 148 through the operation of the control portion 142. The light emitted from the lamps 147a, 147b and 147c of the light source device 148 need not always be visible rays. Each lamp may emit at least one of visible rays, infrared rays and ultraviolet rays.

It is also to be noted that this embodiment may lack one of the expandable mechanism 143 and the light source shifting means 146 annexed to the external illuminating device 141.

Figure 19:
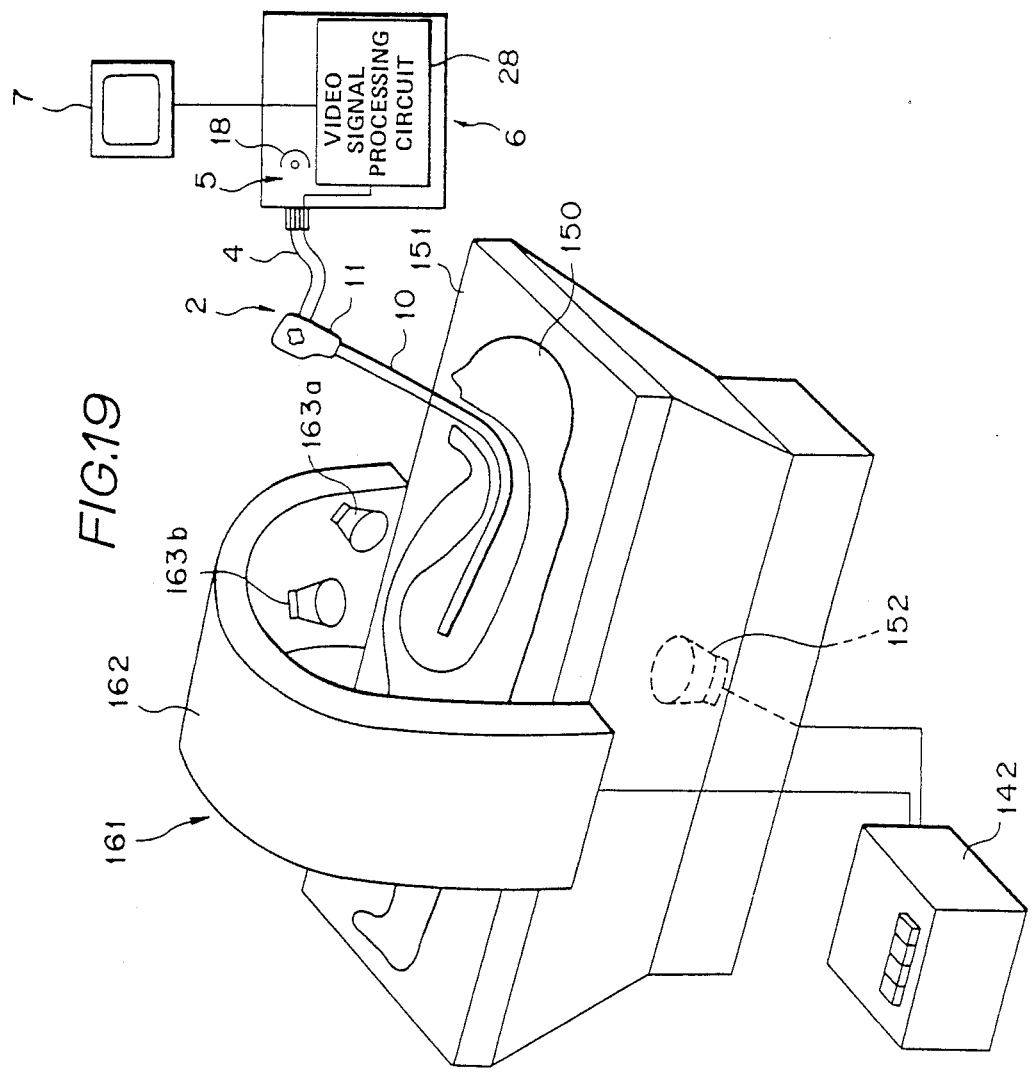
FIG. 19 is an illustration of the fifteenth embodiment of the endoscope apparatus of the present invention.

FIG. 19 shows a fifteenth embodiment of the present invention.

In this embodiment of the endoscope apparatus of the present invention, the external illuminating device 161 is provided with a control portion 142 and an arch-shaped main part 162 detachably secured to the bed 151 so as to bridge over the patient's body. A plurality of illuminating lamps 163a, 163b . . . are provided on the inner surface of the main part 162 at a suitable pitch in the circumferential direction so as to be directed towards the patient 150. Thus, the patient 150 is surrounded by these illuminating lamps 163a, 163b. These illuminating lamps 163a, 163b, are electrically connected to the control portion 142. In operation, as the control portion 142 is suitably operated, the states of the lamps 163a, 163b . . . and the quantities of light therefrom are controlled.

The bed 151 also is provided with an upwardly directed illuminating lamp 152 as is the case of the fourteenth embodiment.

The construction of the endoscope 2 and other devices for observing the body of the patient 150 from the interior of a body cavity is materially the same as that of the fourteenth embodiment.

In this embodiment, the main part 162 of the external illuminating device 161 has a substantially semi-circular form which bridges over the patient's body. The user, therefore, can illuminate the objective part from the most preferred angle, by turning one or more of the lamps 163a, 163b . . . , through the operation of the control portion 142. It is also possible to control the quantities of the lights from the independent lamps through the operation of the control portion 142.

Other aspects of operation and effect are materially the same as those of the fourteenth embodiment.

It is not essential that the lights emitted form the lamps 163a, 163b . . . on the main part 162 are visible rays. Rather, each lamp may emit at least one of visible, infrared and ultraviolet rays.

Furthermore, the solid-state image pickup device 15 provided on the end of the insert portion 10 maybe substituted by a suitable arrangement having a fiber scope with an ocular portion for observation through naked eyes or recording through a television camera or a still camera, and so forth, as in the cases of the fourth to sixth embodiments, or by a film provided in the probe portion of the insert portion as in the cases of the seventh and eighth embodiments.

FIGS. 20 to 23 illustrate a sixteenth embodiment of the present invention.

Figure 20:
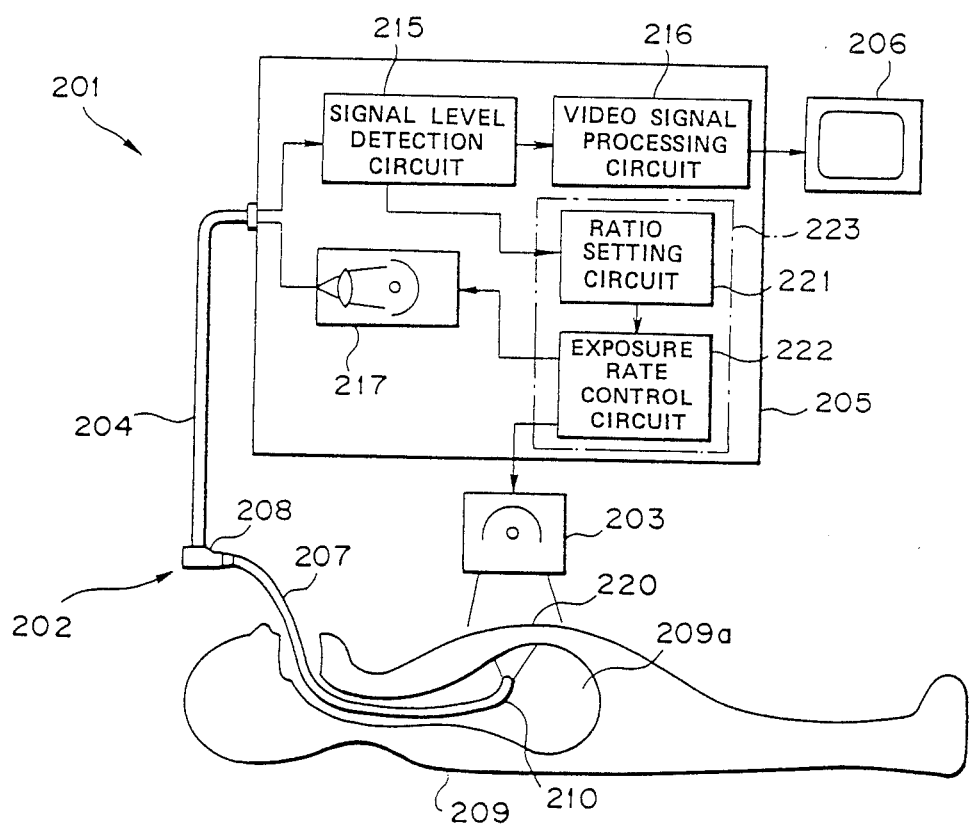
FIG. 20 is an illustration of a sixteenth embodiment of the endoscope apparatus of the present invention.

As will be seen from FIG. 20, the endoscope apparatus 201 of this embodiment has an electronic endoscope 202, an external illuminating light source 203 for applying illuminating light to the electronic endoscope 202 from the exterior of the human body, a control device 205 connected to the electronic endoscope 202 through a cable 204, and a monitor device 206 connected to the control device 205 and serving as a display means.

Figure 21:
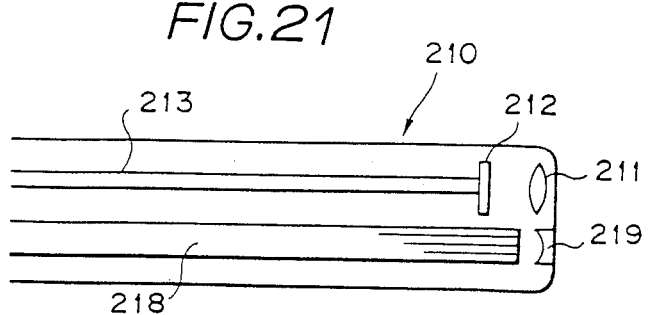
FIG. 21 is an illustration of a probe portion of an endoscope used in the sixteenth embodiment of the endoscope apparatus.

The electronic endoscope 202 has an elongated insert portion 207, and a large-diameter manipulating portion 208 on the rear end of the insert portion 207. The insert portion 207 may be flexible or rigid, and is adapted to be inserted into a body cavity 209a of a human body 209 through, for example, the mouth. The insert portion 207 has an end probe portion 210 which, as shown in FIG. 21, includes an image-forming optical system 211 having an objective lens and so forth, and an image pickup means which is in this embodiment a solid-state image pickup device 212 such as CCD disposed on the imaging position of the image-forming optical system 211. The output from the solid-state image pickup device 212 is input to a signal level detection circuit 215 in the control device 205 via a signal line 213 extended through the insert portion 207 and the cable 204. The output is then delivered to the video signal processing circuit 216 through the signal level detecting circuit 215. The video signal processing circuit conducts various signal processing operations such as wave shaping, γ correction, matrix processing and white balancing, whereby the signal is converted into, for example, a video signal of NTSC system, which is then input to the monitor device 206 so as to form a visible image on the monitor device 206 for observation.

The control device 205 is provided with a light source 217 for internal illumination, and the light from the light source 217 is condensed to impinge upon a light guide 218 which is composed of a flexible fiber bundle. The light guide 218 is extended through the cable 204 and the insert portion 207, so that the internal illuminating light coming into the light guide 218 is emitted from the emitting end of the light guide 218 in the probe portion 210 and is then applied to the object through the light-distributing lens 219. The internal illuminating light reflected by the object in the same angle as the angle of view is received by the solid-state image pickup device 212 through the image-forming optical system 211 so that the reflected light image formed by the light reflected from the object is observed.

The light source 217 for the internal illumination may be a xenon lamp, a halogen lamp, a strobe lamp or the like, and may emit one, two or all of rays of ultraviolet wavelength region, visible wavelength region and the infrared wavelength region. The types of rays emitted from the light source 217 is selected in accordance with the wavelength which is optimum for the observation of the object.

On the other hand, the light emitted from the light source 203 for external illumination impinges upon the surface 220 of the human body 209. The external illuminating light applied to the body surface 220 is transmitted through the organic tissue so as to reach the interior of the body cavity 209a, whereby the transmitted light image of the organic tissue, formed by the external illuminating light transmitted through the tissue, is picked up by the solid-state image pickup device 212.

As in the case of the light source 217 for the internal illumination, the light source 203 for the external illumination may be a xenon lamp, a halogen lamp, a strobe lamp or the like, and may emit one, two or all of rays of ultraviolet wavelength region, visible wavelength region and the infrared wavelength region. The types of rays emitted from the light source 217 is selected in accordance with the wavelength which is optimum for the observation of the object.

In the described embodiment, the output of the solid-state image pickup device 212 is delivered to the signal level detection circuit 215 which detects the levels of the signal representing the reflected light image formed by the internal illumination light and the transmitted light image formed by the external illumination light, as well as the ratio between these signal levels. The ratio of the signal levels provides the ratio of intensity between the reflected light image and the transmitted light image. The ratio of intensity between these two types of image detected by the signal level detecting circuit 215 is input to the control portion 223 which is composed of a ratio setting circuit 221 and an exposure rate control circuit 222. The control portion 223 compares a predetermined ratio set in the ratio setting circuit 221 with the ratio between the reflected light image and the transmitted light image as detected by the signal level detecting circuit 215. In accordance with the result of the comparison, the exposure rate control circuit 222 controls the levels of light emitted from the light source 203 for the external illumination and the light source 217 for the internal illumination, such that the difference between the set ratio and the detected ratio is nullified.

The ratio between the reflected light image and the transmitted light image is detected, for example, as follows. As shown in FIGS. 22A and 22B, the light source 203 for the external illumination and the light source 217 for the internal illumination light up alternately at a suitable timing. The signal from the solid-state image pickup device 212 is then divided in synchronism with the timing of lighting of these two light sources so that the level of the signal produced by the internal illumination light and the level of the signal produced by the external illumination signal are detected independently, whereby the ratio between the reflected light image formed by the internal illuminating light and the transmitted light image produced by the external illumination is detected.

The control portion 223 is capable of effecting various controls. For instance, the control section 223 can control the ratio between the rate of exposure by the internal illumination light and the rate of exposure by the external illumination light in a manner shown in FIG. 23, by suitably setting the ratio in the ratio setting circuit 221. The control portion 223 also can control the exposure rates such that a constant ratio is maintained between the rate of exposure by the internal illuminating light and the rate of exposure by the external illuminating light. It is also possible to conduct switch-over between the internal illuminating light and the external illuminating light as shown in FIGS. 22A and 22B.

The control portion 223 may be such one as being capable of varying the ratio between the rate of exposure by the internal illumination light and the rate of exposure by the external illumination light, in response to a manual operation or fully automatically.

In the embodiment having the described arrangement, the light emitted from the light source 217 for internal illumination is introduced into the body cavity 209a through the light guide 218, and is emitted from the emitting end of the light guide 218, so as to impinge upon the object in the body cavity 209a through the light-distributing lens 219. The internal illumination light reflected by the object is received by the solid-state image pickup device 212 through the image-forming optical system 211, so that the reflected light image of the object is detected, This reflected light image carry various kinds of information such as minute convexities and concavities on the object surface, delicate difference in color, and so forth.

On the other hand, the light emitted from the light source 203 for the external illumination is applied to the surface 220 of the body and reaches the interior of the body cavity 209a through the organic tissue. The transmitted light image of the organic tissue, formed by the externally applied light transmitted through the tissue, is therefore picked up by the solid-state image pickup device 212. The transmitted light image thus obtained carry various kinds of information such as state of running of blood vessels under a membrana, area or region of tumour or infiltration, and so forth. The observation will be facilitated when infrared rays are used as the external illumination light, because the infrared rays have large permeability to organic tissue.

As explained before, the signal level detecting circuit 215 detects the ratio between the reflected light image produced by the internal illumination light and the transmitted light image produced by the external illumination light transmitted through the organic tissue, upon receipt of the output signal from the solid-state image pickup device 212. Then, the control portion 223 operates to control the levels of lights from the light source 203 for the external illumination and the light source 217 for the internal illumination, such that the detected ratio between the reflected light image and the transmitted light image becomes equal to the ratio set in the ratio setting circuit 221.

In this embodiment, the ratio between the rate of exposure by the internal illumination light and the rate of exposure by the external illumination light is suitably controlled by the control portion 223 so that the observation of the reflected light image and the transmitted light image can be conducted with optimum ratio between the intensities of these two types of image, depending on the conditions such as the position of the object, purpose of the observation, and so forth. This advantageously provides information such as the state of the surface of an object together with the state of running of blood vessels under the membrana or other change in the internal condition of the same area of the object. By progressively changing the ratio between the rate of exposure by the internal illumination light and the rate of exposure by the external illumination light, it is possible to observe a given area on the object by way of a synthetic image synthesized from the reflected light image and the transmitted light image with the ratio between the intensities of these two types of images changing momentarily. For instance, referring to FIG. 23, the ratio between the exposure by the internal illumination light and the rate of exposure by the external illumination light is changed progressively and in a stepped manner at a period of one second, so that 30 (thirty) images of different values of the above-mentioned ratio are obtained on one frame.

The control performed by the control portion 223 may be such that a constant ratio optimum for the object position or the purpose of observation is maintained between the rate of exposure by the internal illumination light and the rate of exposure by the external illumination light. By observing different portions of an object with the constant ratio, it is possible to detect any difference in state between these portions of the object.

It is also possible to suitable change-over between the internal illumination light and the external illumination light, by the operation of the control portion 223. In such a case, the user can selectively use either one of the reflected light image and the transmitted light image. For instance, the observation is first conducted by means of the reflected light image so as to obtain information on the surface of the object, e.g., minute convexities and concavities on the surface and delicate difference in the color, and then the internal state of the object under the surface portion where any extraordinary state is found is examined by making use of the transmitted light image, thereby obtaining information such as the state of running of the blood vessels, area of tumor or infiltration, and so forth under the membrana.

Furthermore, the described embodiment contributes to a reduction in the size and weight of the control device 205, because the ratio between the reflected light image and the transmitted light image can be detected by a single signal level detecting circuit 215. The embodiment also enables the internal illuminating light and the external illuminating light to be controlled independently, thus assuring a high accuracy of detection.

Figure 24:
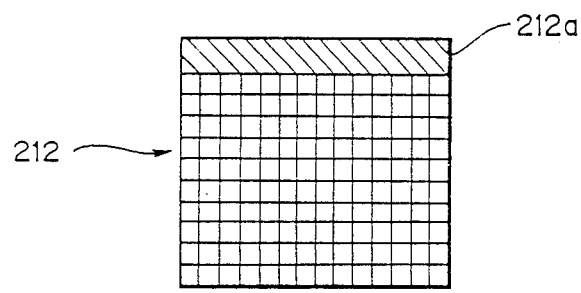
FIG. 24 is an illustration of a solid-state image pickup device used in a seventeenth embodiment of the present invention.

FIG. 24 shows a seventeenth embodiment of the present invention. In this embodiment, a portion of the light receiving surface of the solid-state image pickup device 212 constitutes a detector 212a which is capable of detecting the rate of exposure by the external illumination light or the rate of exposure by the internal illumination light. The external illumination light is, for example, sub-infrared rays which can easily permeate through the organic tissue, while visible rays or ultraviolet rays are used as the external illumination light. An infrared cut-off filter or a visible-rays cut-off filter is mounted to cover the detector 212a so that the detector 212a can detect only one of the external illumination light and the internal illumination light. The output from the detector 212a is delivered to the signal level detecting circuit 215 so that the level of the external illumination light or the level of the internal illumination light is detected by the signal level detecting circuit 215. On the other hand, the output from the light-receiving surface of the solid-state image pickup device 212 other than the detector 212a also is input to the signal level detecting circuit 215 so that the latter produces a signal representing the level of the total light received by the image pickup device 212, including both the reflected internal illumination light and transmitted external illumination light. Therefore, the ratio between the intensity of the transmitted external illumination light and the reflected internal illumination light can be determined from the ratio between the level of the transmitted external illumination light or the reflected internal illumination light and the level of the total light received. Other portions are materially the same as those of the sixteenth embodiment.

According to this embodiment, it is possible to control the ratio between the intensity of the reflected light image and the intensity of the transmitted light image while continuously lighting the light sources for the internal and external illuminations.

Figure 25:
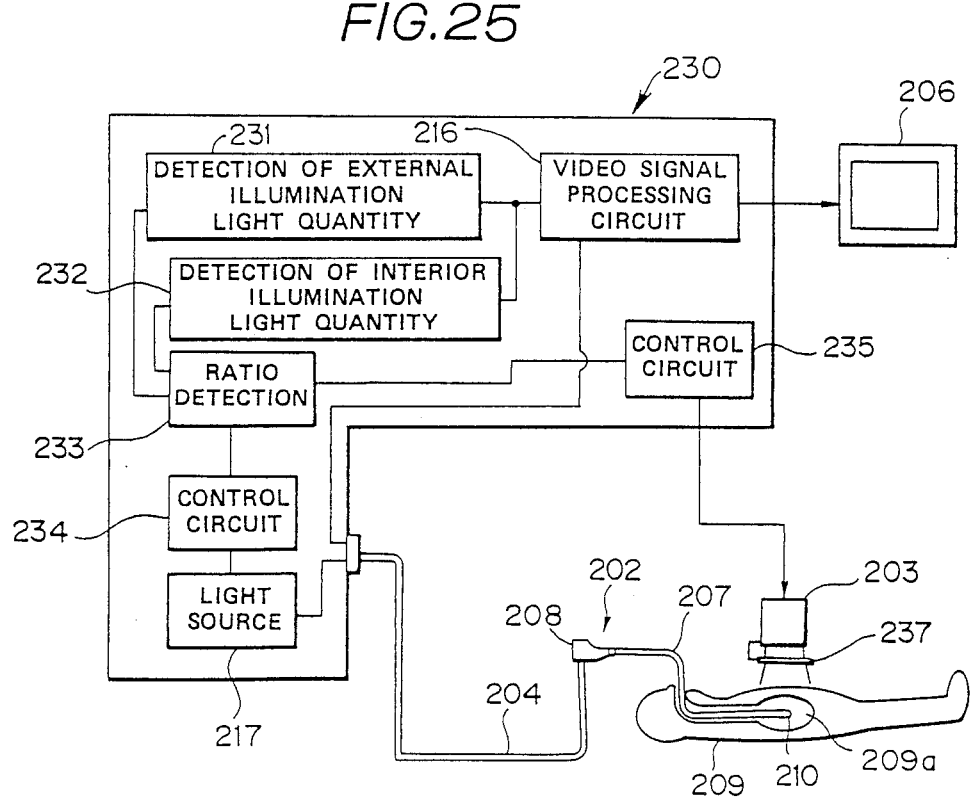
FIG. 25 is a block diagram of the endoscope apparatus of an eighteenth embodiment of the present invention.

FIG. 25 shows an eighteenth embodiment of the present invention. In this embodiment, the control device denoted by 230 has a light source 217 for internal illumination and a video signal processing circuit 216 which effects various processing operations such as wave shaping, correction and encoding to NTSC signal on the output signal from the endoscope 202 inserted into the body cavity. The control device 230 has the following circuits besides the light source 217 and the video signal processing circuit 216: an external illumination light quantity detecting circuit 231 capable of detecting the quantity of light transmitted from the exterior of the body by processing the output signal of the video signal processing circuit 216; an internal illumination light quantity detecting circuit 232 capable of detecting the quantity of the internal illumination light reflected by the object from the output signal of the video signal processing circuit 216; a ratio detecting circuit 233 for detecting the ratio between the quantity of the transmitted external illumination light and the quantity of the reflected internal illumination light from the outputs of the external illumination light quantity detecting circuit 231 and the internal illumination light quantity detecting circuit 232; a control circuit 234 for controlling the quantity of light emitted from the light source 217 for internal illumination in accordance with the ratio detected by the ratio detecting circuit 233; and a control circuit 235 for controlling the quantity of light emitted from the light source 203 for external illumination in accordance with the ratio detected by the ratio detecting circuit 233.

In this embodiment, a filter 237 capable of transmitting the light of the desired wavelength region, e.g., infrared rays, is disposed in front of the light source 203 for external illumination.

Other portions are materially the same as those of the sixteenth embodiment.

In operation, the insert portion 207 of the endoscope 202 is inserted into the body cavity 209a of a human body 209 and the interior of the body cavity 209a is illuminated by the internal illumination light source 217. At the same time, the external illumination light source 203 lights up to externally illuminate the human body so that the objective portion is illuminated by the light transmitted through the organic tissue. The image of the object, illuminated internally and externally by the respective light source 217 and 203 is picked up by the solid-state image pickup device 212 in the endoscope 202, and the output from the solid-state image pickup device 212 is sent to the video signal processing circuit so a to be converted into, for example, a video signal of NTSC system through video processing operations such as wave shaping, $\gamma$ correction, matrix processing and white balancing. This video signal is input to the monitor device 206 so that the observed image is displayed on the monitor device 206.

As explained before, the quantity of the transmitted external illumination light and the quantity of the reflected illumination light are detected from the output of the video signal processing circuit 216, by the external illumination light quantity detecting circuit 231 and the internal illumination light quantity detecting circuit 232, respectively. The outputs from these detecting circuits 231, 232 are input to the ratio detecting circuit 233 which detects the ratio between the levels of exposure by the two types of light. Then, the control circuits 234 and 235 respectively control the quantities of the lights from the internal illumination light source 217 and the external illumination light source 203, in accordance with the ratio which is output from the ratio detecting circuit 233.

Thus, the eighteenth embodiment enables the quantity of the light transmitted from the exterior to illuminate the object and the quantity of the internal illumination light illuminating the object to be controlled independently of each other. With this embodiment, therefore, it is possible to conduct both the observation through the transmitted light image which carries information concerning any disease or state of change deep in membrana tissue and the observation through the reflected light image which bears information such as change in color and slight convexity or concavity on the object surface, under the most appropriate exposure conditions in both modes, whereby the accuracies of observation and diagnosis can be improved remarkably.

Other effects and advantages are the same as those achievable by the sixteenth embodiment.

Figure 26:
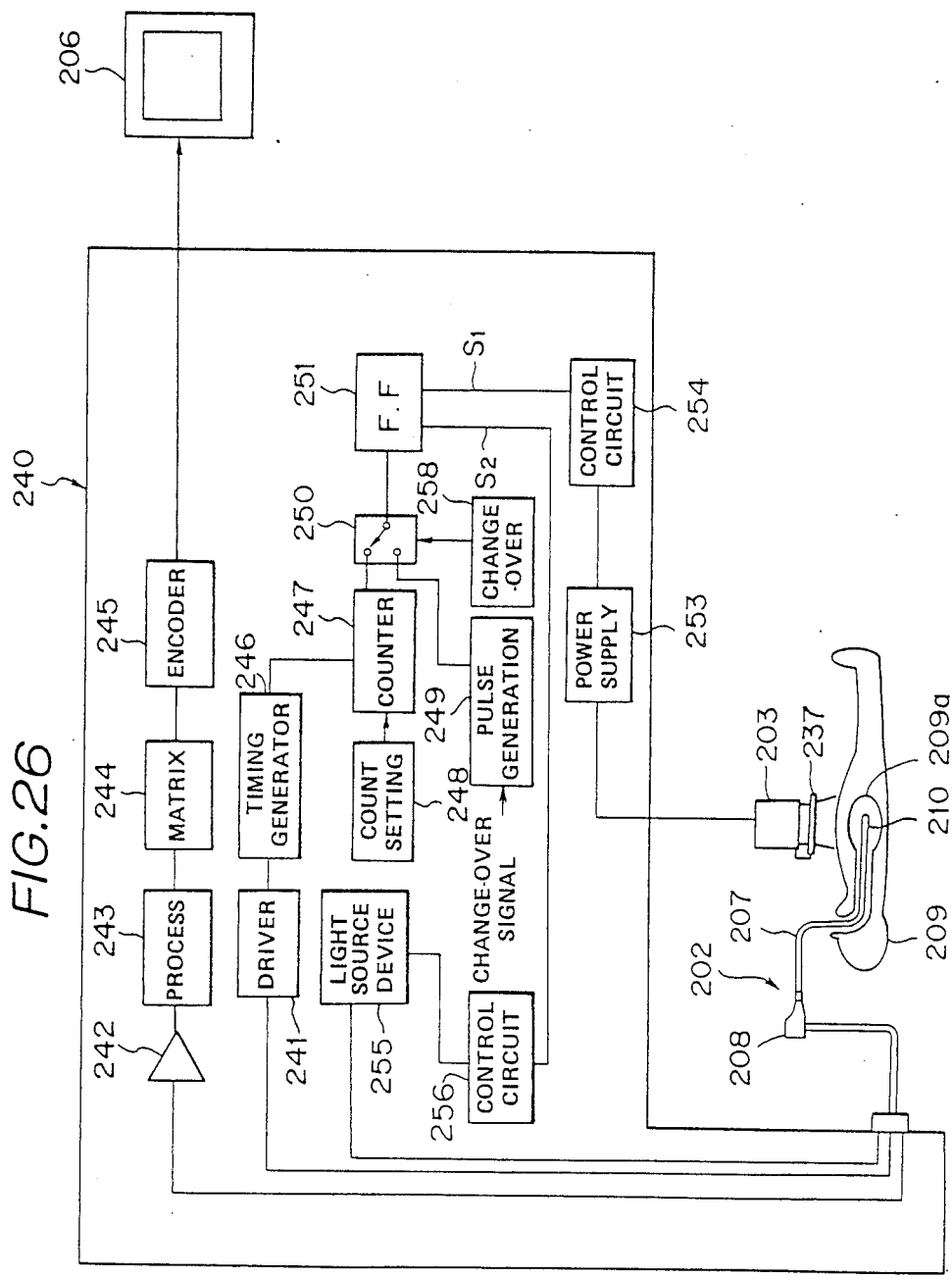
FIG. 26 is a block diagram of a nineteenth embodiment of the endoscope apparatus of the present invention.
Figure 27:
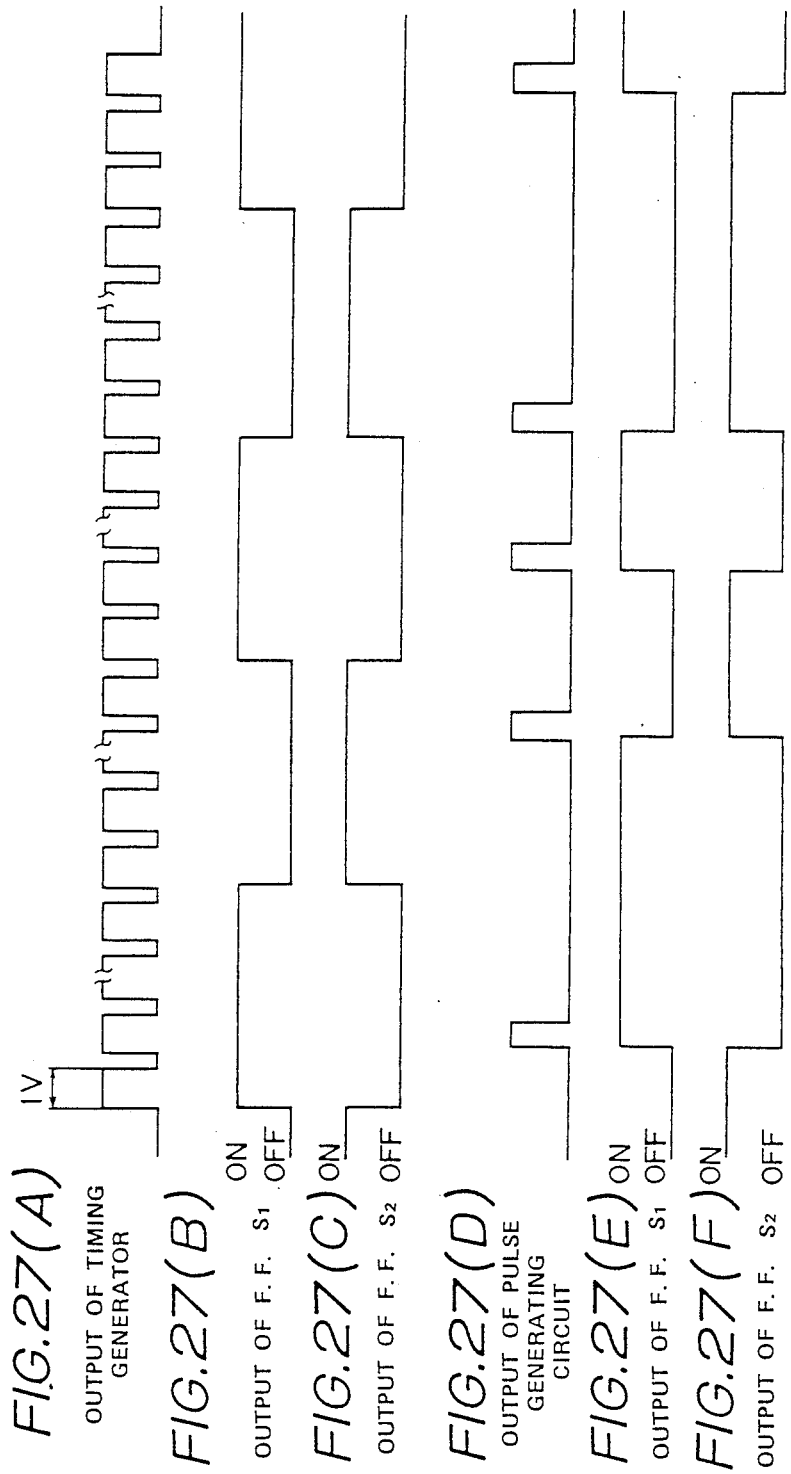
FIG. 27A is a timing chart illustrating the output of a timing generator used in the nineteenth embodiment.
FIG. 27B is a timing chart illustrating the output S1 of a flip-flop used in the nineteenth embodiment.
FIG. 27C is a timing chart illustrating the output S2 of a flip-flop used in the nineteenth embodiment.
FIG. 27D is a timing chart showing the output of a pulse generating circuit in the nineteenth embodiment of the present invention.
FIG. 27E is a timing chart showing the output S1 of a flip-flop used in the nineteenth embodiment.
FIG. 27F is a timing chart showing the output S2 of a flip-flop used in the nineteenth embodiment.

FIGS. 26 and 27 illustrate a seventeenth embodiment of the present invention.

In this embodiment, the control device 240 has the following parts: a driver 241 for driving the solid-state image pickup device 212 in the endoscope 202; a preamplifier 242 for amplifying the output signal from the solid-state image pickup device 212; a process circuit 243 for effecting on the amplified signal various processing operations such as wave shaping, $\gamma$ correction, white balancing and so forth; a matrix circuit 244 for generating a color difference signal from the output signal of the process circuit 243; and an encoder 245 for conversing the color difference signal into, for example, an NTSC video signal. The video signal output from the encoder 245 is delivered to the monitor device 206 so that the image is displayed on the monitor device 206.

This embodiment further has a timing generator 246 for generating timings of operation of various portions of the whole system, as well as synchronizing signals for synchronizing the operations of different circuits in the system, a counter 247 for counting the vertical synchronizing signal output from the timing generator 246, a counter setting circuit 248 capable of changing the count of the counter 247, and a pulse generating circuit 249 capable of generating pulses at the timing determined by a change-over signal which is input manually. A switch circuit 250 switchable by a change-over circuit 258 selects one from the pulse signal from the counter 247 and the signal from the pulse generating Circuit 249, and delivers the selected signal to a flip-flop 251 which is adapted to be inverted in response to each pulse input thereto.

The flip-flop 251 is capable of producing signals S1 and S2 of the opposite phases. The signal S1 is delivered to a control circuit 254 which controls a power supply 253 for supplying electric power to the external illumination light source 203, while the other signal S2 is adapted to be delivered to a control circuit 256 which controls the internal illumination light source device 255, whereby the external illumination light source 203 and the internal illumination light source device 255 are turned on and off, alternatingly.

Other portions are materially the same as those in the sixteenth embodiment.

The operation of this embodiment will be described hereinunder with specific reference to FIGS. 27A to 27F.

The insert portion 207 of the endoscope 202 is inserted into the body cavity 209a of the human body 209, and the interior of the body cavity 209a is illuminated by the light emitted from the internal illumination light source device 255. At the same time, the external illumination light source 203 illuminates the human body 209 externally so that the light is transmitted through the tissue to illuminate the object. The image of the object illuminated by the lights from both light sources 255 and 203 is picked up by the image pickup device 212 in the endoscope 202, and the thus picked up image is displayed on the monitor device 206.

The solid-state image pickup device 212 is driven by the driver 241 in synchronism with the signal from the timing generator 246. The timing generator 246 produces vertical synchronizing signals as shown in FIG. 27A, the number of which is counted by the counter 247. The rate of demultiplication effected by the counter 247 can freely be set by the counter setting circuit 248. For instance, since the vertical synchronizing signals are generated at a frequency of 60 Hz, one output signal is produced from the counter 247 per second, provided that 1/60 demultiplication is effected.

When a change-over signal is manually input, the pulse generating circuit 249 produces a pulse. The switch circuit 250 selects one from the output pulse from the counter 247 and the pulse form the pulse generating circuit 249, and delivers the selected pulse to the flip-flop 251. When the output pulse from the counter 247 has been selected by the switch circuit 250, the timing generator 246 delivers signals synchronous with the vertical blanking period as shown in FIG. 27A. Thee signals are counted by the counter circuit 247 the output of which is sent to the flip-flop 251 through the switch circuit 250. The flip-flop 251 outputs a couple of outputs S1 and S2 of inverse phases as shown in FIGS. 27B and 27C. One S1 of the output signals is delivered to the control circuit 254 for controlling the power supply 253 for the external illumination light source 203, while the other signal S2 is input to the control circuit 256 for controlling the internal illumination control device 255, whereby the external illumination light source 203 and the internal illumination light source device 255 are alternately turned on and off in accordance with the output from the counter 247.

Conversely, when the output of the pulse generating circuit 249 has been selected by the switch circuit 250, the pulse generating circuit 249 operates to produce pulses as shown in FIG. 27D. These pulses are input to the flip-flop 251 through the switch circuit 50. The flip-flop 251 then supplies the control circuits 254 and 256 with on-off signals S1, S2 of inverse phases, so that the internal illumination light source device 255 and the external illumination light source device 203 are alternately turned on and off at the timing coinciding with the period of the pulse output from the pulse generating circuit 249.

As has been described, according to this embodiment, it is possible to obtain, by causing the switch circuit 250 to select the counter 247, a first mode the transmitted light image formed by the external illumination light transmitted from the exterior and the reflected light image formed by the reflected internal illumination light are alternately switched automatically. When the switch circuit 250 selects the pulse generating circuit 249, a second mode is obtained in which the change-over between the transmitted light image and the reflected light image can be conducted at any desired timing.

Other portions are materially the same as those of the sixteenth embodiment.

Figure 28:
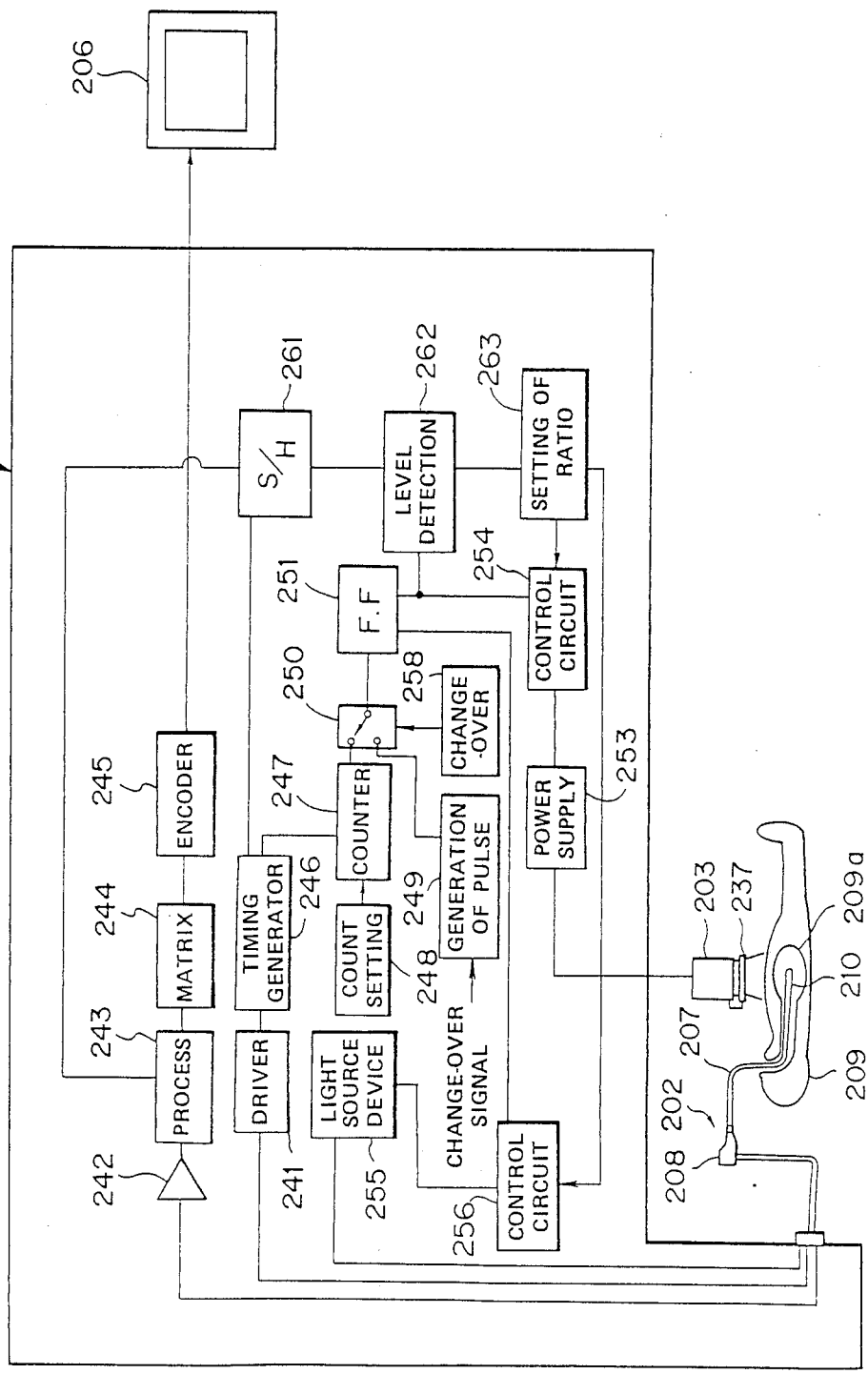
FIG. 28 is a block diagram of a twentieth embodiment of the endoscope apparatus of the present invention.

FIG. 28 shows a twentieth embodiment of the present invention. This embodiment has a control device 260 which includes, in addition to the constituents used in the control device 240 of the nineteenth embodiment, a sample hold circuit 261 which sample-holds the video signals from the process circuit 243 at a timing corresponding to each field, upon receipt of the vertical synchronizing signals output from the timing generator 246, a level detecting circuit 262 which detects the exposure level from the video signal held by the sample hold circuit 261, and a ratio setting circuit 263 which sets the ratio between the external illumination and the internal illumination so as to control the respective control circuits 254 and 256. The level detecting circuit 262 determines, upon receipt of the external illumination on-off signal from the flip-flop 251, whether the detected exposure level is of the external illumination light or of the internal illumination light.

In the described embodiment, the vertical synchronizing signals from the timing generator 246 are input to the sample hold circuit 261 which sample-holds the video signal from the process circuit 243 at a timing corresponding to each field. Then, the level detecting circuit 262 detects the level of exposure from the sample-held video signal in the sample-hold circuit 261.

Whether the detected exposure level is of the external illumination light or the internal illumination light is determined on the basis of the external illumination on-off signal output from the flip-flop 251. In accordance with the exposure level detected by the level detecting circuit 262, the ratio setting circuit 263 sets the ratio between the external illumination and the internal illumination, whereby the control circuits 254 and 256 are controlled in accordance with the thus set ratio, thereby controlling the respective illuminations.

Other portions of the operation and the advantages are materially the same as those of the nineteenth embodiment.

FIGS. 29 and 30 in combination show a twenty-first embodiment of the present invention.

In this embodiment, the probe portion 210 of an endoscope 270 has, as shown in FIG. 30, an image-forming lens which condenses the light from the object so as to form the image of the object, a prism 272 which splits the light condensed by the image-forming lens 272 into two parts, a solid-state image pickup device 273 disposed on the path of one of the two parts of the light split by the prism 272, and a light-receiving element 274 disposed on the path of the other of the two parts of the light split by the prism 272 and capable of sensing the lights of greater wavelengths such as infrared rays transmitted through the organic tissue. Other portions of the construction of the endoscope are materially the same as those of the sixteenth embodiment.

On the other hand, as shown in FIG. 29, the control device 280 of this embodiment has a level detection circuit 281 for detecting the level of exposure of the solid-state image pickup device 273 from the output of the process circuit 243, and a level detection circuit 282 which is capable of detecting, from the output signal of the light-receiving element 274, the exposure level of only the greater wavelength portion of the light received by the solid-state image pickup device 273. The outputs from both level detecting circuits 281 and 282 are input to a computing circuit 283 which computes the ratio of the quantity of the transmitted light to the total light quantity, from the exposure level of the solid-state image pickup device 273 and the exposure level of the light-receiving element 274. The output from the computing circuit 283 is input to the ratio setting circuit 284 which sets the ratio of the quantity of the transmitted light to the total light quantity and gives instructions to the control circuit 254 for the external illumination and the control circuit 256 for the internal illumination thereby setting the quantities of lights of the respective illuminations. In the described embodiments, the external illumination light has a wavelength region greater than that of the internal illumination light. For instance, when infrared rays are used for the external illumination, the internal illumination light may be visible rays or ultraviolet rays. As in the nineteenth embodiment, the control device 280 includes a pre-amplifier 242, a matrix generating circuit 244, an encoder 245, a driver 241 and a timing generator 246.

In this embodiment, the light from the object illuminated by the external illumination light source 203 and the internal illumination light source device 255 is focused by the image-forming lens 271 and is then split into two parts by the prism 272. One of the two parts of the light impinged upon the solid-state image pickup device 273 so as to be picked up by the latter, while the light-receiving element receives only the greater wavelength portion of the other part of the split light.

The image of the object such as a membrana formed by both the transmitted external illumination light and the reflected internal illumination light is picked up by the solid-state pickup device 273 the output of which is processed through the pre-amplifier 242, process circuit 243, matrix circuit 244 and the encoder 245. In consequence, the image formed by the transmitted light and the image formed by the reflected light are displayed on the monitor device at the set ratio. The level detecting circuit 281 detects, from the output signal of the process circuit 243, the level of the exposure of the solid-state image pickup device 273 by both illumination lights. Meanwhile, the other level detecting circuit 282 detects, from the photoelectrically converted output signal of the light receiving element 274, the level of the exposure of the solid-state image pickup device 273 only by the transmitted illumination light. The outputs of both level detecting circuits 281 and 282 are delivered to the computing circuit 283 which computes the ratio of the quantity of the transmitted light to the total light quantity. Then, the ratio setting circuit 284 operates to control the control circuits 254 and 256 for the external and internal illumination such that a preset ratio is attained between the external and the internal illumination light.

Thus, the embodiment under description can vary the ratio between the intensity of the transmitted light image and the reflected light image while the external and internal illuminating lights are continuously emitted.

In this embodiment, the light-receiving element 274 which has a function for merely detecting the light quantity may be substituted by an additional solid-state image pickup device which can pick up the image formed by light of the greater wavelength region. In such a case, as in the case of the solid-state image pickup device 273, the exposure level is detected by processing the output of this additional image pickup device through a pre-amplifier, a process circuit and a level detection circuit. The provision of this additional solid-state image pickup device which can pick up the image formed by light of the greater wavelength region enables two types of image to be obtained simultaneously.

It is also possible to provide a detector capable of detecting either one of the external illumination light and the internal illumination light on a portion of the image pickup surface of the solid-state image pickup device 273.

Figures 31, 32:
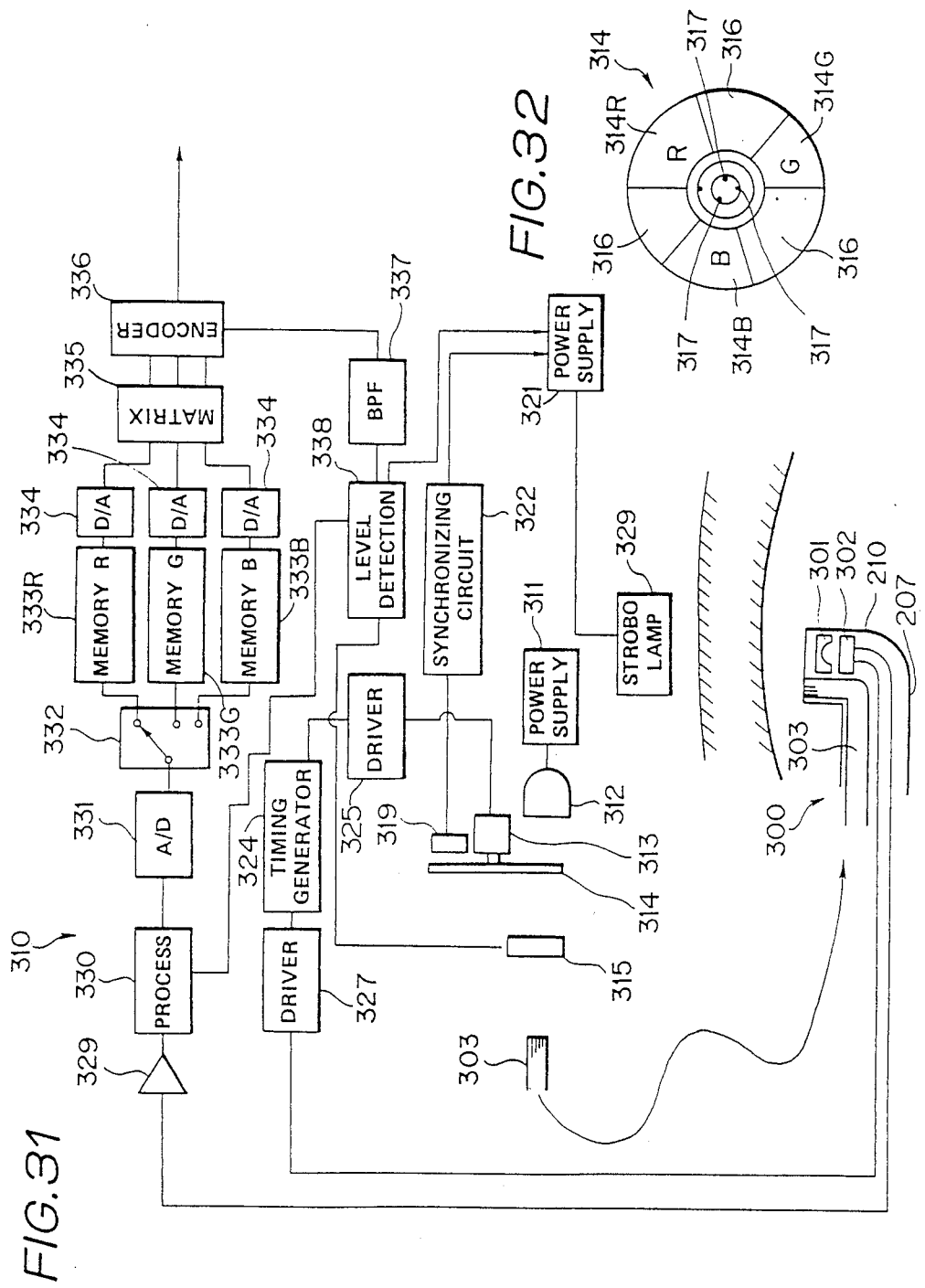
FIG. 31 is a block diagram of a twenty-second embodiment of the endoscope apparatus of the present invention.
FIG. 32 is an illustration of an illustration of a rotary filter used in the twenty-second embodiment.

FIGS. 31 and 32 show twenty-second embodiment of the present invention.

As will be seen from FIG. 31, the end probe portion 210 of the insert portion 207 of the electronic endoscope 300 used in this embodiment has an image-forming lens 301 provided in the end probe portion 210 of the insert portion 207 and a solid-state image pickup device 302 disposed at the imaging position of the image-forming lens 301. A light guide 303 is extended through the insert portion 207 so as to transmit the internal illumination light which is emitted from the probe portion 210 so as to illuminate the object.

The control device 310 of this embodiment has a lamp 312 as the light source for the internal illumination light. The lamp 312 is supplied with electric power from the power supply 311. A rotary filter 314 driven by a motor 313 and an aperture device 315 for controlling the quantity of light coming into the light guide 303 are disposed between the lamp 312 and the incident end of the light guide 303.

As will be seen from FIG. 32, the rotary filter 314 has three types of filters 314R, 314G and 314B which are arranged in the circumferential direction and capable of transmitting lights of the R, G and B wave length regions. Light-shielding portions 316 are provided between the filters 314R and 314G and between the filters 314G and 314B. A marking 317 of different reflectivities are provided for indicating the positions of the respective filters 314R, 314G and 314B. Thus, the positions of the filters 314R, 314G and 314B are detected by a rotary filter encoder 319 capable of sensing the marking 317. The light emitted from the aforementioned lamp 312 is divided into components of the R, G and B wavelength regions in a time-serial manner by the rotation of the rotary filter 314, and these components are time-serially input to the light guide 303, so as to illuminate the objective organic tissue from the interior of the body.

In this embodiment, a strobe lamp 320 powered by a power supply 321 is used as the light source for the external illumination. A synchronizing circuit 322 for generating the timing of lighting of the strobe lamp 320 is connected to the power supply 320. The output of the rotary filter encoder 319 is input to the synchronizing circuit 322 so that the latter produces timing signals for lighting the strobe lamp 320 in accordance with the positions of the filters 314R, 314G and 314B.

The embodiment further has a timing generator 324 which generates timings of the respective portions of the whole system and synchronizing signals for attaining synchronism of operation between different circuits of the system. The motor 313 is adapted to be controlled by a motor driver 325 in synchronization with a synchronizing signal generated by the timing generator 324.

The embodiment further has a driver 327 which drives the solid-state image pickup device 302 in synchronization with the synchronizing signal generated by the timing generator. The output signal read from the solid-state image pickup device 302 driven by the driver 327 is amplified by a pre-amplifier 329 and is input to a process circuit 330 so as to undergo necessary signal processing operations such as wave shaping and $\gamma$ correction. The output from the process circuit 330 is converted into a digital signal by an A/D converter 331 the output of which is delivered through a switch circuit 332 so as to be selectively stored in memories 333R, 333G and 333B which are adapted to store image formed by the R, G and B illuminating lights, respectively. The image signal components which are read from the solid-state image pickup device 302 in a time-series manner in the sequence of, for example, R, G and B are sorted by the switch circuit 332 so as to be forwarded to the respective memories 333R, 333G and 333B corresponding to the components R, G and B. The signal components read out of the memories 333R, 333G and 333B are respectively converted into analog video signals by a D/A converter 334 and are then input to a matrix circuit 335. The matrix circuit 335 is adapted to form color difference signals from the R, G and B video signals. The color difference signals are input to the encoder 336 which forms, for example, an NTSC video signal from these color difference signals. The video signal output from the encoder 336 is input to the monitor device 206 so as to be displayed on the latter.

The output from the encoder 336 is input to the bandpass filter 337 which enables only 3.58 MHz color component of the NTSC signal output from the encoder 336, thereby producing a chroma-signal. The image signal output from the process circuit 330 and the chroma-signal from the band-pass filter 337 are input to a level detecting circuit 338 which detects the level of the chroma signal. The level detecting circuit 338 is adapted for controlling the power supply 321 and the aperture device 315 in accordance with the level of the chroma-signal thereby controlling the quantity of the external illumination light and the quantity of the internal illumination light.

Figure 33:
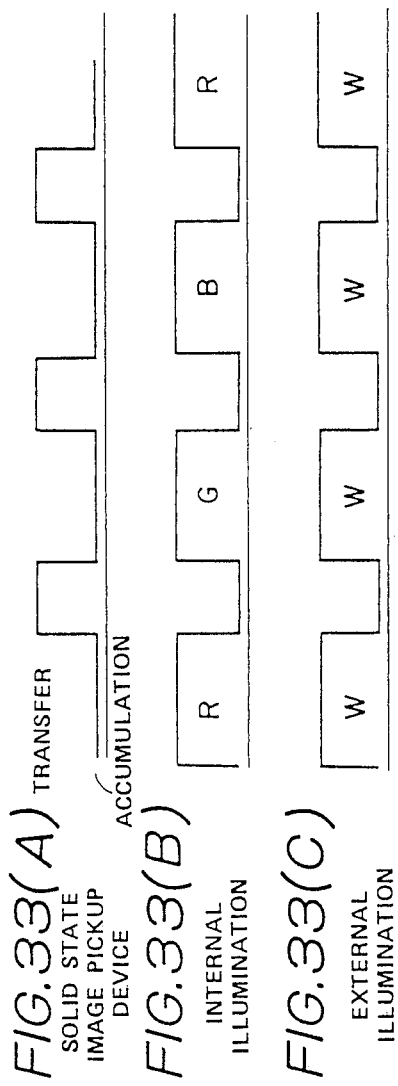
FIG. 33A is a timing chart illustrating the operation mode of the solid-state image pickup device in the twenty-second embodiment.
FIG. 33B is a timing chart illustrating the timing of emission of internal illuminating light in the twenty-second embodiment.
FIG. 33C is a timing chart illustrating the timing of emission of external illuminating light in the twenty-second embodiment.

In the illustrated embodiment, the internal illumination light emitted from the lamp 312 is divided in a time-series manner into R, G and B wave length components by the rotary filter 314, as shown in FIG. 33B, and these components are transmitted through the light guide 303 so as to be emitted from the end of the endoscope 300, thereby illuminating a tissue such as a membrana from the interior of the body. Meanwhile, the strobe lamp 320 operates at a timing generated by the synchronizing circuit 322 so as to produce a light of the same spectral characteristic, e.g., a white light W, at timings corresponding to R, G and B, as will be seen from FIG. 33C, thus producing the external illumination light.

The solid-state image pickup device 302 of the endoscope 300 receives, as shown in FIG. 33A, the light coming from the object, i.e., the portion of the external illumination light transmitted through the object and the portion of the internal light reflected by the object, and accumulates charges obtained by a photoelectric conversion of the received light signal. The solid-state image pickup device 302 then transfers the accumulated charges in synchronism with the switching of the internal illumination light to a vertical transfer path when inter-line transfer method is used and to an accumulating section when frame transfer method is used.

The output signal from the solid-state image pickup device 302 is amplified by the pre-amplifier 329 and is input to the process circuit 330 so as to be wave-shaped and $\gamma$ corrected. The output signal from the A/D converter 331 is then converted into a digital signal so as to be stored in the memories 333R, 333G and 333B. The contents of these memories 333R, 333G and 333B are read simultaneously and the respective read signals are converted by the D/A converter 334 into analog signals. These analog signals are delivered to the matrix circuit 335 which produces color difference signals. The color difference signals are converted into NTSC signal by an encoder 336. The NTSC signal is input to the monitor device 206 so that the observed image is displayed on the monitor device 206.

In the embodiment, the reflected light image formed by the internal illumination light reflected by the object is displayed as a color image, while the transmitted light image formed by the transmitted external illumination light is displayed as a monochromatic image. It is therefore possible to detect the ratio between the reflected light image and the transmitted light image by the chroma-level.

It is also to be understood that the band-pass filter 337 used in this embodiment allows only the chroma-signal component of 3.58 MHz from among the components of the NTSC signal output from the encoder 336. On the other hand, the process circuit 330 provides an output from which the total exposure level is detected and the chroma-level with respect to the total exposure amount is detected by the level detecting circuit 338. Then, the level detecting circuit 338 controls the power supply 321 and the aperture device 315 in accordance with the level of the chroma-signal, thereby controlling the quantities of the external and internal illumination lights.

It is possible to arrange such that the strobe lamp 320 for the external illumination lights up in synchronism with only one or two of the R, G and B colors of the internal illumination light, rather than all the R, G and B colors. With such an arrangement, it is possible to detect the ratio between the reflected light image and the transmitted light image, through detection of a change in hue.

For instance, when the external illumination lights up in synchronism with G or B component of the light, it is possible to cause a change in the color tone within the endoscopic image in which the R component has a large ratio. It is therefore possible to use the level detection circuit as a hue detecting circuit, so that the levels of the images formed by the external illumination light and the internal illumination light, as well as the ratio therebetween, can be detected not only from a change in the chroma-level but also from a change in the hue.

It is also to be understood that, by making reference to the chroma-level obtained when the external illumination is not used, it is possible to accurately detect the ratio between the level of the image produced in the external illumination light and the level of the image produced by the internal illumination light, even for a white blank portion such as esophagus which inherently provides a low chroma-level, though the illustration lacks any arrangement which would enable such a reference to be conducted.

Thus, the twenty-second embodiment makes it possible to detect the ratio between the reflected light image and the transmitted light image from the chroma-level or, as well as from a change in the hue. It is therefore possible to visually discriminate the reflected light image and the transmitted light image from each other.

Figures 34, 35:
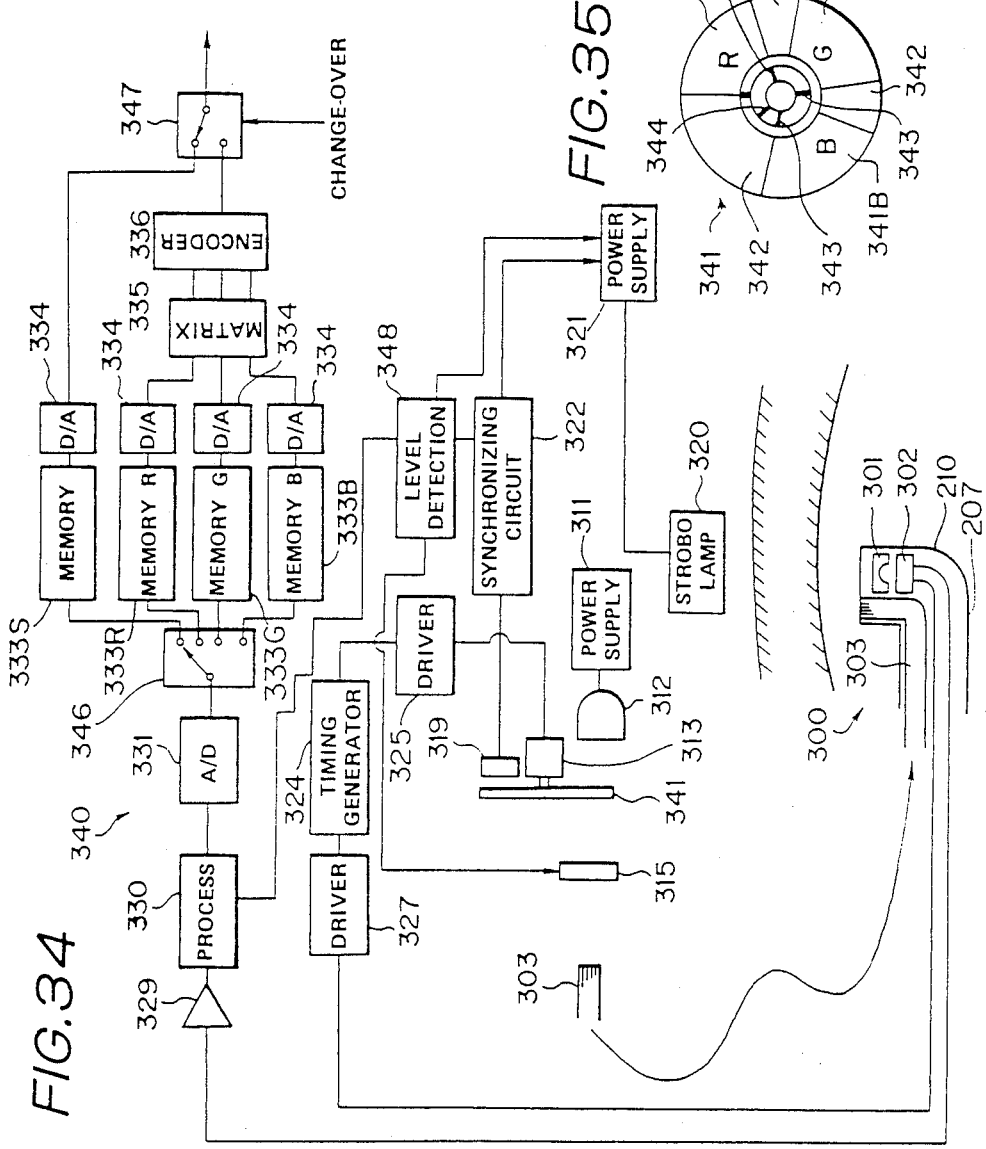
FIG. 34 is a block diagram of a twenty-third embodiment of the endoscope apparatus of the present invention.
FIG. 35 is an illustration of a rotary filter used in the twenty-third embodiment.

FIGS. 34 and 36 shows a twenty-third embodiment of the present invention.

This embodiment features a rotary filter 341 as shown in FIG. 35, in place of the rotary filter 314 of the twenty-second embodiment. The rotary filter 341 has three types of filters 341R, 341G and 341B which are capable of transmitting R, G and B wavelengths of the light. These filters 341R, 341G and 341B are arranged in the circumferential direction on the rotary filter 341, with light-shielding portions 342 interposed between the respective adjacent filters 341R, 341G and 341B. The light-shielding portions 342 between the filter 341B and the filter 341R has a length which is greater than those of other light-shielding portions. The rotary filter also is provided with markings in terms of differences in, for example, reflectivities which indicate the positions of the respective filters 341R, 341G and 341B. At the same time, a marking 344 which indicates the timing of lighting of the strobe lamp 320 is provided on the light-shielding portion 342 between the filter 341B and the filter 341R. These markings 343 and 344 are read by a rotary filter encoder 319. The rotary filter encoder 319 produces, through a synchronizing circuit 322, synchronizing signals which enable the level detecting circuit 328 to detect the levels of the R, G and B images formed by the internal illumination light and the level of the image produced by the external illumination light provided by the strobe lamp 320, while generating the lighting timing of the strobe lamp 320.

This embodiment further has, in addition to the memories 333R, 333G and 333B corresponding to the R, G and B colors used in the preceding embodiment, a memory 333S for storing the transmitted light image formed by the external illumination light provided by the strobe lamp 320. The signal from the A/D converter 331 is therefore sorted into R, G, B and S components which sent to the memories 333R, 333G, 333B and 333S, respectively.

The signal read from the memory 333S is converted by the D/A converter 334 into an analog signal, and this analog signal and the image signal output from the encoder 336 is input to the switch circuit 347 which selects one of the output of the encoder 247 and the output of the memory 333S in response to an external switching operation. The selected signal is sent to the monitor device 206 for the purpose of display.

In the embodiment, the level detection circuit 328 used in the twenty-second embodiment is substituted by a level detecting circuit 348 which operates in synchronism with the signals from the synchronizing circuit 322 indicative of the positions of the filters 341R, 341G and 341B, and the signal from the same indicative of the timing of lighting of the strobe lamp 320.

Other portions are materially the same as those of the twenty-second embodiment.

In the twenty-third embodiment under description, the light emitted form the lamp 312 for internal illumination is divided into R, G and B wavelength components in a time-series manner as shown in FIG. 36A by the operation of the rotary filter 341, and these components are applied to the object from the interior of the body.

On the other hand, the strobe lamp 320 flashes in accordance with the timing as shown in FIG. 36B output from the rotary filter encoder 319, so that the external illumination light is emitted from the strobe lamp 320 when the internal illumination light is interrupted between the B and R components of the internal illumination light, as shown in FIG. 36C.

Referring now to FIG. 36D, the solid-state image pickup device 302 picks up images corresponding to R, G, B and flash lights. The images corresponding to the R, G, B and flash lights read from the solid-state image pickup device 302 in a time serial manner are stored in the respective memories 333R, 333G, 333B and 333S as they are separated and directed by the switch circuit 346.

The signals rear out from the memories 333R, 333G and 333B are processed, as in the twenty-second embodiment, through the D/A converter 334, matrix circuit 335, and the encoder 336 so as to become an NTSC signal which is input to the switch circuit 347. On the other hand, the signal read from the memory 333S is changed into an analog monochromatic image signal through the D/A converter 334 and the thus obtained monochromatic image signal is input to the switch circuit 347. The switch circuit 347 operates in response to an external manual input so as to select one from the output of the encoder 247 and the signal from the memory 333S and delivers the selected signal to the monitor device 306. When the output of the encoder 247 is selected and delivered to the monitor device 206, an ordinary color image of the object formed by the internal illumination light is displayed on the monitor 306, whereas, when the output of the memory 333S is selected, the monitor device 206 displays a monochromatic image formed by the transmitted external illumination light produced by the strobe lamp 320.

In this embodiment, reflected light images of the R, G and B illumination light components and the transmitted light image produced by the light from the strobe lamp 320 are formed independently of each other in a single field or frame. Therefore, the level detecting circuit 348 can detect, in synchronization with the output signal from the synchronizing circuit 322, the signal level of the transmitted light image from the level of the output signal obtained from the solid-state image pickup device at the time of lighting of the strobe flash. On the other hand, the signal levels of the reflected light images of the respective colors are detected from the levels of the signals output from the solid-state image pickup device 302 in synchronization with the internal illumination by the R, G and Blight components.

FIGS. 37 to 41 show a twenty-fourth embodiment of the present invention.

As will be seen from FIG. 37, the end probe portion 210 of the endoscope 350 used in this embodiment has an image-forming lens 351 for condensing light from the object, a half mirror for splitting the light condensed by the image-forming lens into two parts which run in different directions, a solid-state image pickup device 353 provided on the path of one of these two parts of the light split by the half mirror 352, and a light-receiving element 354 provided on the path of the other part of the light and capable of detecting the quantity of light produced by the strobe lamp 320. Other portions of the endoscope 350 are the same as those in the sixteenth embodiment.

The control device 360 used in this embodiment is provided with a rotary filter 361 substantially the same as the rotary filter 314 used in the control device 310 of the twenty-second embodiment. As will be seen from FIG. 38, the rotary filter 361 has three types of filters 314R, 314G and 314B which are arranged in the circumferential direction and adapted to transmit the light components of R, G and B wavelengths, respectively. Light shielding portions 316 are provided between the respective adjacent filters 314R, 314G and 314G. Markings 362 in terms of, for example, differences in reflectivity are provided on the terminal end portions of the openings of the respective filters 314R, 314G and 314B, for producing lead pulses. Furthermore, a marking 363 for generating a start pulse is provided in the starting end of the opening of the filter 314R. These markings 362 and 363 are adapted to be detected by rotary filter encoders 319, so that a start pulse and lead pulses synchronous with the periods of exposure by R, G and B light components are input to the synchronizing circuit 365.

The level detecting circuit 338 receives the output from the light-receiving element 354 and the image signal from the process circuit 330. Upon receipt of these signals, the level detecting circuit 338 detects the levels of exposure by the respective illumination light components R, G and B, as well as the level of exposure by the flash light from the strobe lamp 320, in synchronization with the output pulse form the synchronizing circuit 365. The level detection circuit 338 controls the power supply 321 for the external illumination and the aperture device 315, thereby controlling both the external illumination light quantity and the internal illumination light quantity.

FIG. 39 shows the construction of the synchronizing circuit 365. Namely, the synchronizing circuit 365 has a counter 366 adapted to be reset by the start pulse from the rotary encoder 319 so as to count the lead pulses, a timer-1 367a which delays the lead pulse by $T\omega1$ when the number counted by the counter 366 is 1, a timer-2

367b which delays the lead pulse by $T\omega 2$ when the number counted by the counter 366 is 2 a timer-3 367c which delays the lead pulse by $T\omega 3$ when the number counted by the counter 366 is 3, and an OR gate 369 which receives the output pulses from the respective timers 367a, 367b and 367c through a switch 368.

The output of the OR gate 369 is input to the level detecting circuit 338.

In this embodiment, the light emitted from the lamp 312 for internal illumination is decomposed into light components of R, G and B wavelengths in a time-series manner by the rotary filter 361 as shown in FIG. 40A, and these light components are sequentially applied to the object from the interior of the body.

The rotary filter encoder 319 produces, as shown in FIGS. 40B and 40C, a start pulse and lead pulses in synchronization with the periods of exposure by the R, G and B light components are delivered to the synchronizing circuit 365, when the start pulse marking 363 and the lead pulse markings 362 on the rotary filter 361 are detected by the rotary filter encoder 319. The synchronizing circuit 365 then enables the counter 366 to count the lead pulses corresponding to R, G and B, and, as shown in FIG. 40D, delays the lead pulses corresponding to the R, G and B light components by $T\omega 1$, $T\omega 2$ and $T\omega 3$, when these pulses are read from the encoder 319 by the timers 367a, 367b and 367c. The thus delayed lead pulses are output to the level detection circuit 338 and the power supply 321. The power supply 321 operates in synchronization with the delayed lead pulses from the synchronizing circuit 365 so as to cause the strobe lamp 320 to flash. Meanwhile, the level detecting circuit 338 operates in synchronization with the delayed lead pulses from the synchronizing circuit 365 so as to detect the quantity of light received from the strobe lamp 320 from the output of the light-receiving element 354 of the endoscope 350. When the delayed lead pulse from the synchronizing circuit 365 is not received, the level detection circuit 338 detects the amounts of exposure by the R, G and B light components, from the video signal output from the process circuit 330.

Referring now to FIG. 40E, the strobe lamp 320 is allowed to flash in the period after the completion of the transfer of the charges in the solid-state image pickup device 353 in the endoscope 350 till each filter 314R, 314G and 314B starts to open. As will be seen from FIG. 40E, the solid-state image pickup device 353 conducts photoelectric conversion of the images produced by the internal illumination light components R, G and B and the image produced by the external illumination light from the strobe lamp 320, and accumulates the signal charge corresponding to these images. The monitor device 206 in this embodiment displays an image which is synthesized from the reflected light image and the transmitted light image.

As has been described, in the twenty-fourth embodiment, the external illumination is provided by a flash light and the levels of the reflected light image and the transmitted light image are detected through detection of the amount of exposure when the flash light is on.

Alternatively, the arrangement may be such that the strobe lamp 320 flashes while the respective internal illumination lights R, G and B are being applied, and the exposure level of the transmitted light image is detected by the level detection circuit 338 in synchronization with the flash of the strobe lamp 320. In this case, the quantity of light obtained from the internal illumination and the quantity of light obtained from the external illumination are not distinctively discrete from each other. However, the influence of the light from the internal illumination is almost negligible because the flash from the strobe lamp 320 provides an extremely large quantity of light in quite a short time as compared with each of the R, G and B internal illumination lights. Thus, the amount of exposure by the internal illumination light and the amount of exposure by the external illumination light can be detected by regarding the exposure amount measured under the flash as being the same as the amount of exposure by the external illumination light alone.

Figure 42:
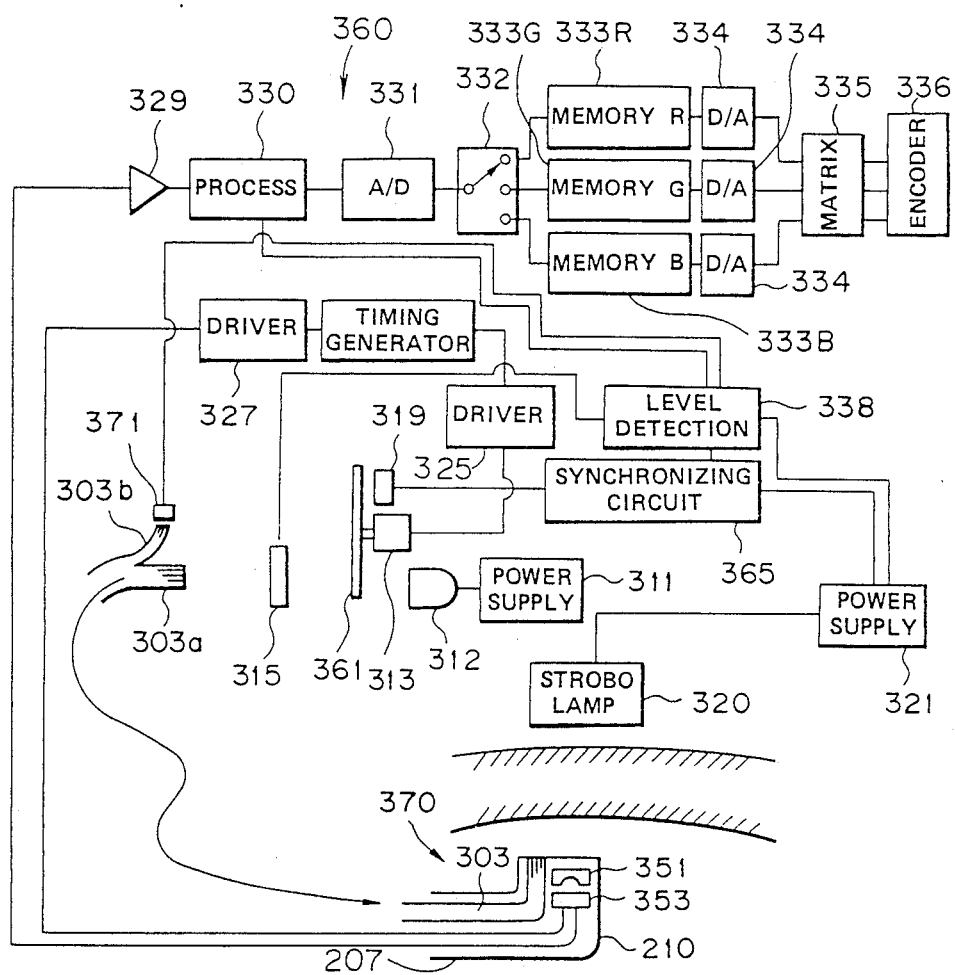
FIG. 42 is a block diagram of a twenty-fifth embodiment of the endoscope apparatus of the present invention.

FIG. 42 shows a twenty-fifth embodiment of the present invention.

In this embodiment, the end probe portion 210 of the endoscope 370 has a bifurcated light guide 303 having a pair of incident ends or branches, in place of the combination of the half-mirror prism 352 and the light-receiving element 354 in the preceding embodiment. One 303a of these two branches is disposed on the path of light from the lamp 312 to serve as a light guide, while the other branch is positioned to oppose the light-receiving element 371 in the controller 360 so as to serve as the means for detecting the light quantity on the object to be observed. The light emitted from the lamp 312 impinges upon the branch 303a of the light guide 303 and is transmitted through the latter so as to be emitted from the end probe portion 210 of the endoscope. A part of the light from the object, derived from the internal or external illumination light, impinges upon the light guide 303 and is emitted from the end of the other branch 303b so as to be received by the light-receiving element 371. The output from this light-receiving element 371 is input to a level detecting circuit 338, whereby the level of exposure by the external illumination light is detected. Other structural features, as well as operation and advantages, are the same as those of the twenty-fourth embodiment.

It is possible to insert an optical fiber for measuring the light quantity on the object by inserting a light-quantity measuring optical fiber into an instrument channel of the endoscope and measuring the quantity of light transmitted through this optical fiber by the light-receiving element 371.

Figure 43:
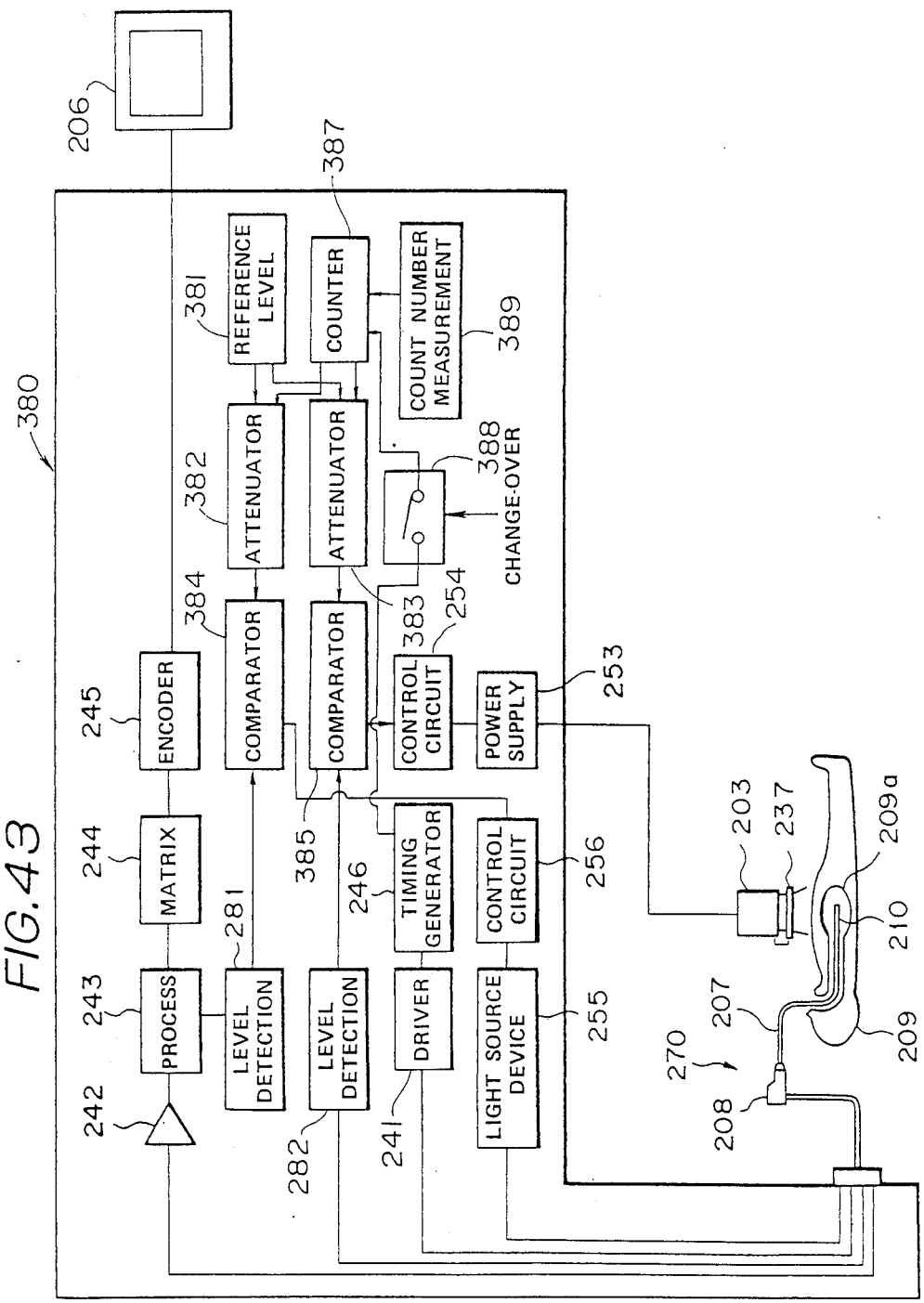
FIG. 43 is a block diagram of a twenty-sixth embodiment of the endoscope apparatus of the present invention.

FIG. 43 shows a twenty-sixth embodiment of the present invention which is similar to the twenty-first embodiment.

The control device 380 used in this embodiment has the following parts: a reference level setting circuit 381 for setting the reference level of exposure; a pair of attenuators 382, 383 for attenuating the reference level set by the reference level setting circuit 381; a comparator 384 for comparing the level of exposure by the internal light derived from the level detecting circuit 281 with a reference level output from the attenuator 382 and for delivering a control signal to the control circuit 256 of the light source device 255 for internal illumination; and a comparator 385 for comparing the level of exposure by the external light derived from the level detecting circuit 282 with a reference level output from the attenuator 383 and for delivering a control signal to the control circuit 254 for controlling the external illumination light.

The control device 380 also has a counter 387 which demultiplies and counts the vertical synchronizing signals generated by the timing generator 246 and increases or decreases the rates of attenuation caused by the attenuators 382 and 383. A switch 388 adapted to be turned on and off by an external operation is disposed between the counter 387 and the timing generator 246. A count number setting circuit 389 connected to the counter 387 is adapted to vary the value of demultiplication performed by the counter 387. The signal input from the counter 387 into the attenuator 382 and 383 are so determined that, while one serves to increase rate of attenuation performed by the attenuator to which it is input, the other serves to decrease the rate of attenuation performed by the attenuator to which it is input.

Other portions of the arrangement of this embodiment are materially the same as those of the twenty-first embodiment.

In operation of this embodiment, a reference value of the exposure level is set through the reference level setting circuit 381.

When the switch 388 is turned on by external operation, the vertical synchronizing signals from the timing generator 246 are received by the counter 387 which supplies the attenuators 382 and 383 with signals at a frequency corresponding to the rate of demultiplication set by the count number setting circuit 389, such that each attenuator receives one piece of signal in a period which is an integer multiple of the vertical synchronizing signals. The signals from the counter 387 tend to vary in the rates of attenuation in opposite directions, as explained before. Therefore, the rates of attenuation performed by the attenuators 382 and 383 are controlled such that the total light quantity received is constant while the ratio between the component derived from the external illumination light and the component derived from the internal illumination is changed. The signals set at the respective reference levels by the attenuators 382, 383 are compared by comparators 384, 385 with the level detection circuits 281, 282, and the control circuits 256 and 254 are controlled such that the signal levels detected by the respective level detecting circuits 281 and 282 become equal to the corresponding reference levels set by the attenuators 382, 383, whereby the quantities of the internal illumination light and the external illumination light are controlled at the reference levels. In consequence, the ratio between the amount of exposure by the internal illumination light and the amount of exposure by the external illumination light is changed as shown in FIG. 23.

It is possible to set the time or speed of the change in the above-mentioned ratio at any desired level, by changing the amount of demultiplication of the counter 387 by means of the count number setting circuit 389.

When the switch 388 is turned off by an external operation, the counter 387 does not receive the vertical synchronizing signals from the timing generator 246, so that the given ratio between the amount of exposure by the internal illumination light and the amount of exposure by the external illumination light is maintained.

Thus, the twenty-sixth embodiment of the invention makes it possible to automatically change the ratio between the amount of exposure by the internal illumination light and the amount of exposure by the external illumination light at any desired speed and also to hold the ratio at a constant level.

Other operational features and advantages are the same as those in the twenty-first embodiment.

Figure 44:
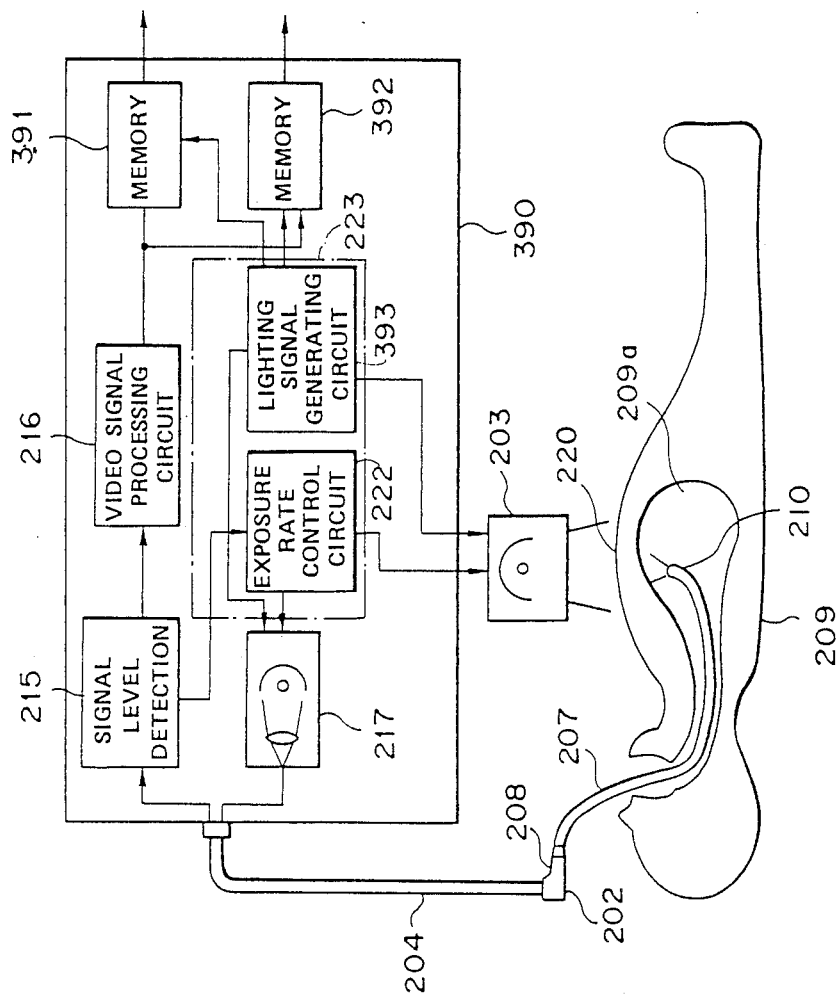
FIG. 44 is a block diagram of a twenty-seventh embodiment of the endoscope apparatus of the present invention.

FIG. 44 shows a twenty-seventh embodiment of the present invention which is similar in construction to the sixteenth embodiment.

In this embodiment, the output from the video signal processing circuit 216 is input to a reflected light image memory 391 and a transmitted light image memory 392. The control portion 223 is composed of an exposure amount control circuit 222 and a light-emission signal generating circuit 393. The light source 217 for the internal illumination and the light source 203 for the external illumination are operated alternately as shown in FIGS. 22A and 22B, in response to a light-emission signal generated by the light-emission signal generating circuit 393. In consequence, the solid-state image pickup device 212 alternately picks up the reflected light image and the transmitted light image. As in the case of the sixteenth embodiment, the signal level detecting circuit 215 detects the levels of signals corresponding to the reflected light image and the transmitted light image, from the output signal of the solid-state image pickup device 212. These signal levels are input to the exposure amount control circuit 222 which operates in response to these signals so as to control the levels of light emission from the light source 217 for the internal illumination and the light source 203 of the external illumination.

Meanwhile, the video signal processing circuit 216 alternately produces a video signal corresponding to the reflected light image and a video signal corresponding to the transmitted light image, in response to the switching between the internal illumination and the external illumination. The contents of the reflected light image memory 391 and the transmitted light image memory 392 are up-dated in accordance with the synchronizing signal generated by the light-emission signal generating circuit, so that the reflected light image memory 391 stores only the reflected light image, while the transmitted light image memory 392 stores only the transmitted light image.

In this embodiment, it is possible to manage the images in various manners by effecting change-over between the internal illumination and the external illumination in a short period, e.g., on the field basis or on the frame basis, as in the case of the sixteenth embodiment. For instance, it is possible to vary the ratio between the exposure amount by the internal illumination light and the exposure amount by the external illumination light, or alternatively, to maintain the ratio at the constant level, as well as to control the amounts of exposure by the respective lights independently.

In addition to these advantages, the twenty-seventh embodiment offers an advantage that it can record the reflected light image and the transmitted light image independently of each other. In the reproduction of the recorded images, a synthetic image can be formed by synthesizing both images with a variety of ratios between two images or maintaining a constant value of the ratio. It also becomes possible to switch-over the operation mode between the external illuminating mode and the internal illuminating mode, so as to enable the amounts of exposure to be controlled independently. Furthermore, the separate storage of the reflected light image and the transmitted light image enables various video processing operations which are conducted by making use of both types of image.

In order to make the reflected light image and the transmitted light image to be visually distinguishable from each other, the sixteenth to twenty-seventh embodiments may be provided with means for displaying the reflected light image as a color image while displaying the transmitted light image as a monochromatic image as in the twenty-second embodiment. It is also possible to display the reflected light image on one of R, G and B colors or one of complementary colors, or to display the reflected light image and the transmitted light image in different colors.

The information derived from the signal level detecting circuit 215 concerning the ratio between the reflected light image and the transmitted light image may be superposed on the signals of images to be displayed or recorded.

It is also to be understood that ultraviolet rays can be used as the internal or external illumination lights, although visible rays and infrared rays are specifically mentioned as the illumination lights in the foregoing description of embodiments. The combination of the rays to be used as the internal and external illumination lights may be selected as desired depending on conditions such as the position of observation, purpose of the observation and so forth.

In the sixteenth to twenty-seventh embodiments, the solid-state image pickup device may be of the type which sequentially changes the color of the illuminating light such as R, W (white), B and so forth in accordance with surface sequence method, or may be of a single plate type having a color filter provided on the front side of the solid-state image pickup device. In these embodiments, it is not essential that the image pickup device is of the solid-state type device. Thus, these embodiments may be modified such that the image is transmitted through an image guide for observation by naked eye or for recording by, for example a television camera sensitive to a desired wavelength region or a still camera which makes use of an ordinary film or an infrared film, as in the case of the fourth to sixth embodiments. It is also possible to modify these embodiments such that the image is recorded by an ordinary film or an infrared film provided in the end probe portion of the endoscope, as in the cases of the seventh and eighth embodiments. It is even possible to suitably combine two or more of these features.

Thus, the sixteenth to twenty-seventh embodiments of the present invention makes it possible to control the ratio between the transmitted light image formed by the light transmitted through an organic tissue and the reflected light image produced by the internal illumination light, thus enabling the user to obtain images which are optimum for the position of the object or the purpose of the observation, by virtue of the exposure control means which controls the amount of exposure by the light transmitted through the organic tissue from the exterior and the amount of exposure by the internal illumination light which is directly applied to the object from the inside of the body.

Figure 45:
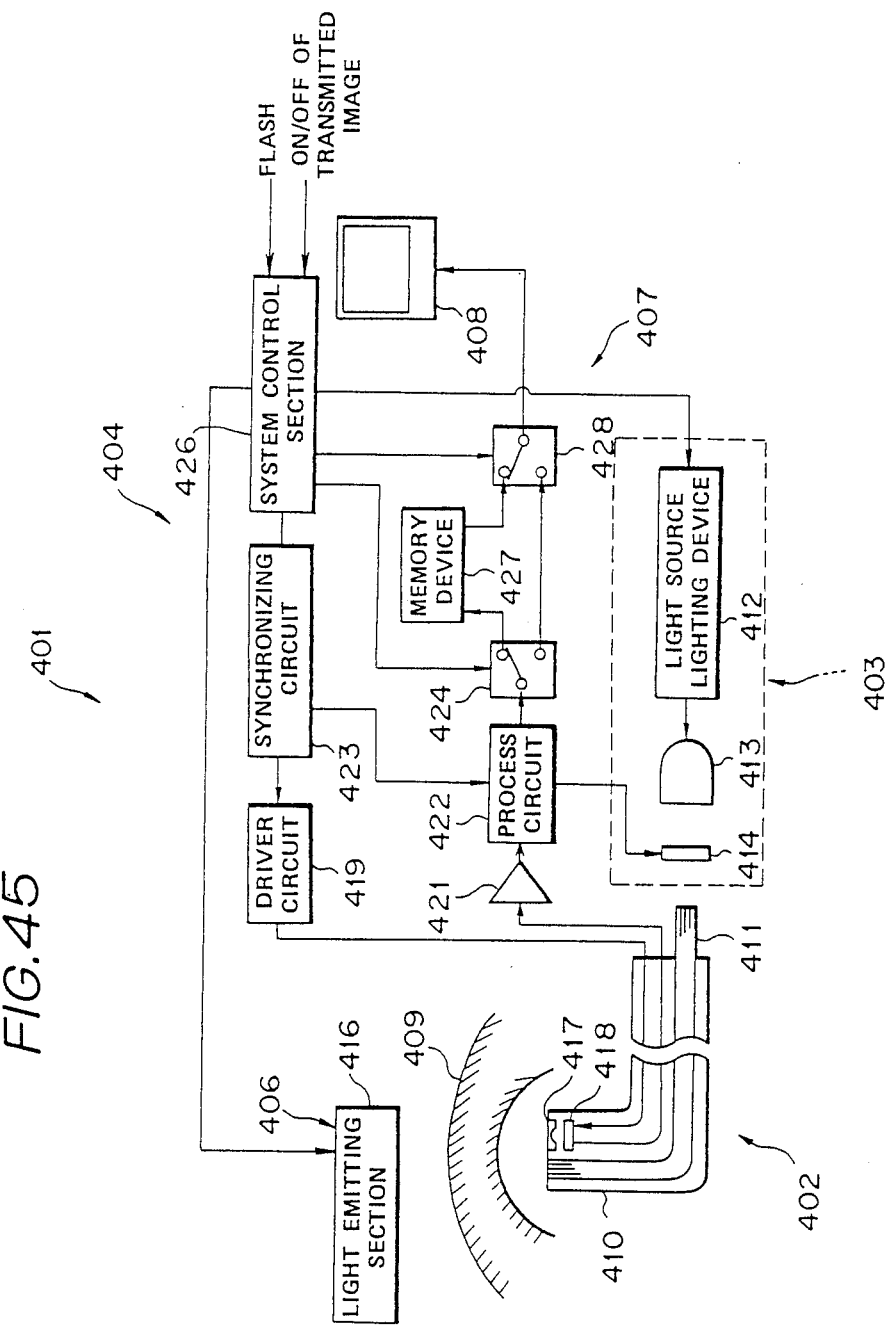
FIG. 45 is a block diagram of a twenty-eighth embodiment of the endoscope apparatus of the present invention.

FIGS. 45 and 46 show a twenty-eighth embodiment of the present invention.

Referring first to FIG. 45, the endoscope apparatus of this embodiment, generally denoted by 401, has an electronic endoscope 402, an endoscope control device 407 connected to the rear end of the electronic endoscope 402 and accommodating a light source 403 for internal illumination, a signal processing portion 404 and a light source 406 for external illumination, and a monitor device 408 which receives a video signal from the endoscope control device 407 and capable of displaying the endoscopic image.

The electronic endoscope 402 has an elongated insert portion 410 which can easily be inserted into a body 409 of, for example, a patient. A light guide 41 extending through the insert portion 410 is capable of transmitting the illumination light and emitting the same from the end thereof. The light source 403 for internal illumination has a lamp driving device 412 and a lamp 413 supplied with electric power from the driving device 412 so as to enable the lamp 413 to emit light of white color, and an aperture 414 through which the emitted white light is made to concentrate and impinge upon the incident end of the light guide 411.

The light source 406 for the external illumination has a power supply section (not shown) capable of supplying electric power necessary for flashing, and a light-emitting portion 416 having, for example, a strobe lamp capable of flashing upon receipt of power from the power supply portion. An image is formed on the image pickup surface of a solid-state image pickup device 418 such as a CCD constituting an image pickup means, by the light image from the body or organ 409 formed by the internal illumination light reflected by the organ 409 and the external illumination light transmitted through the organ, through the objective lens 417. The solid-state image pickup device 418 is capable of converting the optical image formed thereon into electric signals. Thus, the solid-state image pickup device 418 produces a video signal through photoelectric conversion, in response to a drive signal applied by the driver circuit 419. The video signal is amplified by a pre-amplifier 421 and is then input to a process circuit 422.

The driver circuit 419 is supplied with a control signal for determining the timing of generation of the driving signal for driving the solid-state image pickup device, from a synchronizing circuit 423 which generate timing signals for various part of the whole endoscope apparatus 401.

The process circuit 422 operates to process the video data from the pre-amplifier 421 in such a manner as to trim the color tone, effect $\gamma$ conversion, and conversion into video signal. The output from the process circuit 422 is delivered to a switch circuit 424 which serves as a selection means. The process circuit 422 also controls the aperture 414 so as to control the brightness in the body cavity by adjusting the level of intensity of the internal illumination light.

The switch circuit 424 operates in accordance with the control signal from the system control section 426 such as to deliver the video signal selectively either to a memory device 427 as a memory means constituted by frame memories or the like capable or recording the video signal or to another switch circuit 428 which also serves as a selection means. Thus, the video signal can be written in the memory device 427. The switch circuit 428 is capable of selecting one of two modes: namely a mode in which the video signal stored in the memory device 427 is read in accordance with the control signal from a system control portion 426 and a mode in which the video signal output from the process circuit 422 is directly input to the monitor device 408.

The system control section 426 is adapted to be supplied with a timing signal from the synchronizing circuit 423 and to control the electric power supplied to the lamp 413 from the lamp driving device 412 in accordance with externally given flash signal. The system control section 426 also allows the light-emitting portion 416 to intermittently light up after the switch circuit 424 has been operated to select the mode for writing data in the memory device 427, thereby allowing the memory device 427 to record the transmitted light image formed by the external illumination light transmitted through the organ. When an ON signal for the transmitted light image is given externally, the switch circuit 428 is switched to select the mode for reading the content of the memory device 427, so that the recorded transmitted light image can be output to the monitor device 408. When an OFF signal is given externally, the power supplied from the lamp driving device 412 is increased, and a switching in conducted between the switch circuits 424, 428 thereby enabling the reflected light image produced by the internal illumination light to be output to the monitor device 408.

The operation of this embodiment will be described hereinunder with specific reference to FIGS. 46A to 46H.

The light emitted from the lamp 413 of the light source 403 for internal illumination is applied to the incident end of the light guide 411 through the aperture 414 so as to illuminate the inner wall of the cavity in the body 409. The light is then reflected by the wall so as to form a reflected light image on the image pickup surface of the solid-state image pickup device 418. The thus formed image in the form of charges are accumulated and transferred in synchronization with the timing signal shown in FIG. 46A. The video signal representing the reflected light image is amplified by the pre-amplifier 421 and, after a color trimming and γ correction through the process circuit 422, converted into video signal which is delivered to the monitor device 408 through the switch circuits 424, 428 so as to be displayed on the monitor device 408.

Figure 46A:
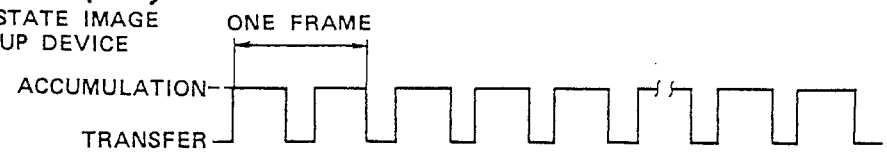
FIG. 46A is a timing chart illustrating the operation mode of a solid-state image pickup device in the twenty-eighth embodiment.
Figure 46B:
FIG. 46B is a timing chart illustrating the timing of a flash signal used in the twenty-eighth embodiment.
Figure 46C:
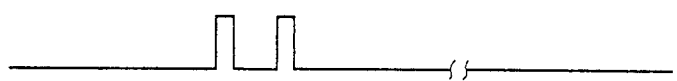
FIG. 46C is a timing chart illustrating the timing of emission of light from an external light source.
Figure 46D:
FIG. 46D is a timing chart illustrating a change in the light from an internal light source.
Figure 46E:
FIG. 46E is a timing chart illustrating the timing of switching operation of a switch circuit incorporated in the twenty-eight embodiment.

When an external flash signal is input to the system control portion 426 as shown in FIG. 46B, the internal illumination is put off or dimmed as shown in FIG. 46D, so that the switch circuit 424 operates in the next frame to make the memory device 427 ready for writing for a period corresponding to one frame, as shown in FIG. 46E. In this frame, the external illumination is turned on for each field as shown in FIG. 46C, whereby the transmitted image is written in the memory device 427. More specifically, the light-emitting portion 416 is made to flash twice, before and after a vertical blanking period in the period of one frame of the solid-state image pickup device 418 which is being driven in a field reading mode.

Figure 46F:
FIG. 46F is a timing chart illustrating the timing of another switching circuit incorporated in the twenty-eighth embodiment.

After the completion of the writing, the switch circuit 424 is changed-over as shown in FIG. 46E so that the memory device 427 becomes unable to write. At the same time, the switch circuit 428 is changed-over as shown in FIG. 46F so that the memory device 427 becomes ready for reading, so that the transmitted light image can be displayed on the monitor device 408. In addition, the internal illumination is turned on or intensified to illuminate the interior of the body 409.

After elapse of a predetermined time, the switch circuit 428 is changed-over by the OFF signal of the transmitted light image, so that the reflected light image formed by the reflected internal illumination light is displayed on the monitor device 408.

In this embodiment, the transmitted light image is recorded in the memory device 427 so that it can be displayed throughout a desired period on the monitor device 408. Therefore, no flickering of the image on the monitor 408 takes place even when the emission of light from the light-emitting portion 416 is ceased. At the same time, the total energy applied to the body 409 is minimized and the transmitted light image can be obtained from any desired depth in the body 409.

The period of display of the transmitted image can be set as desired or the display may be automatically changed into the mode for producing the reflected light image by the internal illumination. The switching to the mode for displaying the reflected light image may be conducted manually by the operator after a sufficient examination of the transmitted light image. It is also possible to arrange such that the flash of the external illumination is turned on only at the portion in question, after a careful check through observation by the internal illumination, so that the transmitted light image is obtained only from the portion which has been noted during the check by the internal illumination.

Figure 46G:
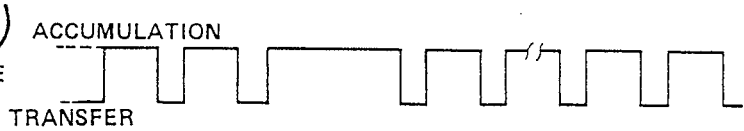
FIG. 46G is a timing chart illustrating the operation mode of a solid-state image pickup device in the twenty-eight embodiment.
Figure 46H:
FIG. 46H is a timing chart illustrating the timing of emission of light from an external light source in the twenty-eighth embodiment.

FIGS. 46G and 46H show an arrangement in which, while the solid-state image pickup device is being driven in the field reading mode, the solid-state image pickup device 418 is read over a number of frames corresponding to the flashes of the light-emitting portion 416, whereby one frame of transmitted light image is obtained per each flash of the light.

The memory device 427 may be constituted by a magnetic recording means.

Figure 47:
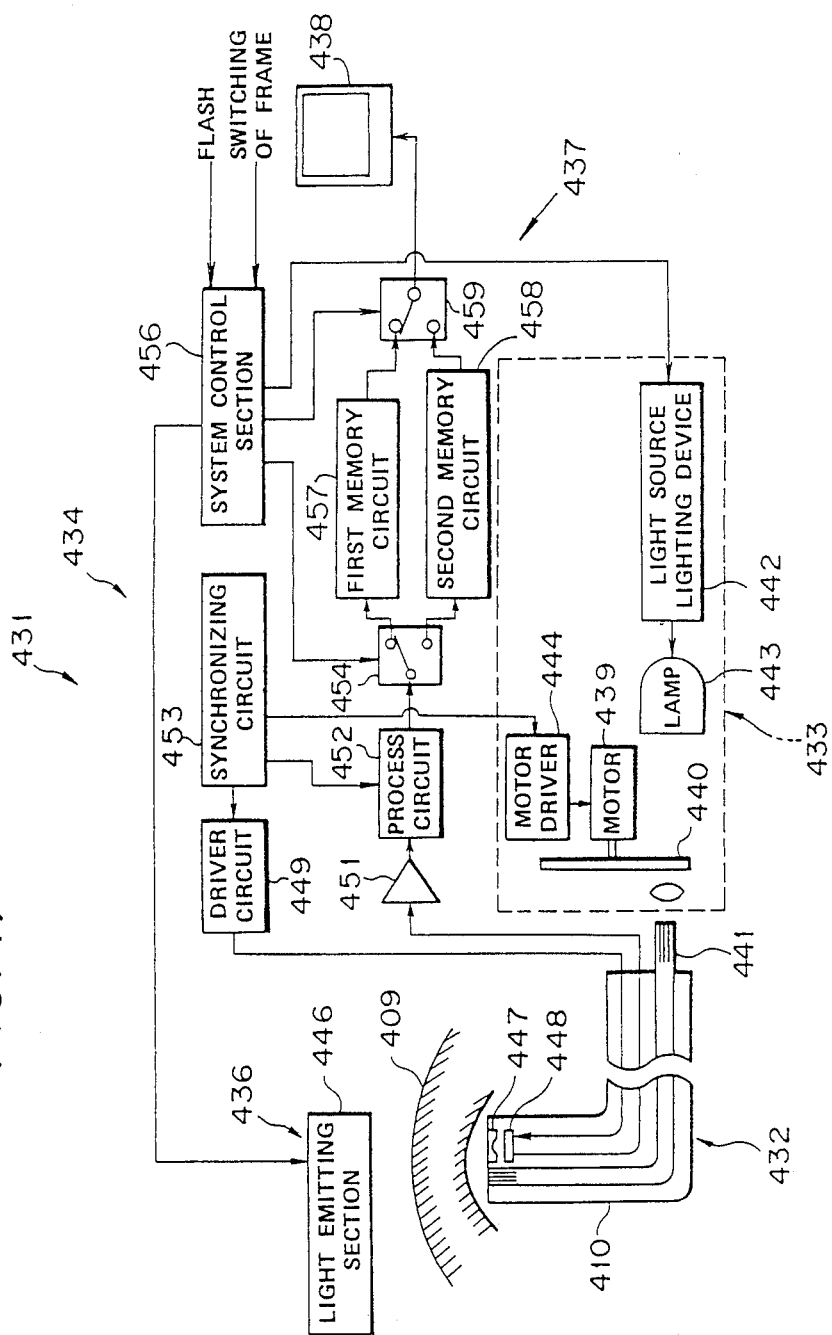
FIG. 47 is a block diagram of a twenty-ninth embodiment of the endoscope apparatus of the present invention.

FIGS. 47 and 48 show a twenty-ninth embodiment of the present invention.

As will be seen from FIG. 47, the endoscope apparatus 431 of the present invention has an electronic endoscope 432, an endoscope control device 437 connected to the rear end of the endoscope 432 and provided with a light source 433 for internal illumination, a signal processing portion 434 and a light source 436 for external illumination, and a monitor device 438 for displaying an image in accordance with a video signal received from the endoscope control device 437.

The electronic endoscope 432 has an elongated insert portion 410 which is easy to insert into the body cavity in a body 409. A light guide 441 extended through the insert portion 410 is adapted to transit illumination light and to emit the same from an end thereof.

The light source 433 for internal illumination has a light driving device 442 and a lamp 443 adapted to be supplied with electric power from the driving device 442. The white light emitted from the lamp 443 is transmitted through a rotary filter 440 which is driven by a motor 439 so that red, green and blue illuminating lights are generated in sequence. These lights are sequentially concentrates and impinges upon the incident end of the light guide 441.

The light source 436 for external illumination has a power supply portion capable of supplying electric power for producing light flash, and a light-emitting portion 446 having, for example, a strobe lamp adapted to flash by the power supplied from the power supply. The light image formed by the internal illuminating light and the external illuminating light transmitted through the body is focused by an objective lens 447 on the image pickup surface of a solid-state image pickup device 448 serving as image pickup means. The optical image formed on the image pickup surface undergoes photoelectric conversion performed by the solid-state image pickup device 448. The solid-state image pickup device 448 outputs a video signal formed by the photoelectric conversion, upon receipt of a image pickup device driving signal from a driver circuit 449. The video signal is amplified by the pre-amplifier 451 and is input to a process circuit 452. The driver circuit 449 is supplied with a control signal for determining the timing of output of the solid-state image pickup device driving signal, from a synchronizing circuit 453 which produces timing signals for various parts of the whole endoscope apparatus. The synchronizing circuit 453 also delivers a control signal for determining the timing of operation of the motor 439 to the motor driver 444 which applies a motor drive signal to the motor 439.

The process circuit 452 explained before conducts various processing operations such as white-balancing, γ correction and so forth on the video signal which is input thereto through the pre-amplifier 451, and converts the video signal into three primary-color signals R, G and B. These signals are delivered to a switch circuit 454 which serves as a selection means.

The switch circuit 454 operates in response to a control signal from the system control portion 456 in such a manner as to deliver the RGB signals selectively either to a first memory circuit 457 as a recording means composed of frame memories and so forth capable of recording one frame of video data, and a second memory circuit 458 of a similar construction. The RGB signals recorded in the first or the second memory circuits 457 and 458 are read out through a switch circuit 459 which can select either one of the first and the second memory circuits 457, 458 in accordance with a control signal given by the system control portion.

The system control portion 456 is adapted to operate, upon receipt of a timing signal from the synchronizing circuit 453, so as to restrict the electric power supplied from the lamp driving device 442 to the lamp 443 in response to an externally given flash signal. The system control portion 456 also operates to cause the light-emitting portion 446 to intermittently flash, after the switch circuit 454 is changed over to select the writing mode of the second memory circuit 458, thereby enabling the second memory circuit 458 to record the transmitted light image formed by the flash of the external illumination light. When an externally given change-over signal instructs to output the transmitted light image, the switch circuit 459 is changed-over to select the second memory circuit 458 thereby enabling the recorded transmitted light image to be output to the monitor 438. Conversely, when the change-over signal instructs to output the reflected light image, the electric power supplied to the lamp driving device 442 is increased to operate the switch circuits 454, 459 to select the first memory circuit 457, whereby the reflected light image formed by the internal illumination light reflected within the body 409 is displayed on the monitor 438.

The operation of this embodiment will be described hereinunder with reference to FIGS. 48A to 48G.

The light emitted from the lamp 443 provided in the light source for internal illumination is made to pass through the rotary filter 440 so that red, green and blue lights are successively applied to the incident end of the light guide 441 thereby to illuminate the inner surface of the wall of the body 409. The light reflected by the surface of the body wall is focused on the image pickup surface of the solid-state image pickup device 48 to form a reflected light image thereon, and the thus formed image in the form of charges is accumulated and transferred in synchronization with the timing signal as shown in FIG. 48A. The video signal representing the reflected light image is then amplified by the pre-amplifier 451 and undergoes processing operations such as white-balancing and γ correction conducted by the process circuit 452. The video signal is then converted into three primary-color signals RGB and is output to the switch circuit 454.

The system control portion 456 operates in response to the image switching signal so as to change-over the switch circuit 454 and the switch circuit 459 thereby to alternately effect writing and reading. Namely, when a reflected light image is being written in either one of the first memory circuit 457 and the second memory circuit 458, video signal corresponding to one frame of image is output from the other of the memory circuits so that the read reflected light image is displayed on the monitor device 438.

When an external flash signal is input to the system control portion 456 as shown in FIG. 48B, the internal illumination is turned off or dimmed as shown in FIG. 48E. Then, in the next frame, the switch circuit 454 is changed-over so that the second memory circuit 458 becomes ready for writing for a period corresponding to one frame, as shown in FIG. 48F. Then, the external illumination is turned on in this frame as shown in FIG. 48D so that the external illumination is made to flash in this frame, whereby the transmitted light image is written in the second memory circuit 458. More specifically, the light-emitting portion 446 is made to flash for three times, before and after the vertical blanking period within the period of one frame of the solid-state image pickup device 448 which is being driven in the field reading mode.

When the writing is over, the switch circuit 459 is changed-over in response to an externally given change-over switch which instructs to display the transmitted light image. In consequence, as shown in FIGS. 48F and 48G, the writing in the second memory circuit 458 is prohibited and reading therefrom is allowed, whereby the transmitted light image as a still image is displayed on the monitor 438 as shown in FIG. 48C. At the same time, the internal illumination is turned on or intensified to illuminate the interior of the body 409, as shown in FIG. 48E.

After elasp of a predetermined time, an externally given image change-over signal instructs to display the reflected light image. In consequence, the first switch circuit 459 is changed-over so that writing and reading to and from the first memory circuit 457 and the second memory circuit 458 are enabled to allow the reflected light image as a dynamic image to bed is played on the monitor 438.

In this embodiment, the total energy of illumination applied to the body 409 can be reduced because the light-emitting portion 446 for the external illumination only flashes, i.e., lights up only intermittently. In addition, both a still image formed by the transmitted external illumination light and ordinary observation through internal illumination are available, for consecutive switching therebetween. This considerably improves the diagnostic performance and facilitates the confirmation of location of the examined object, with the result that the manipulation of the apparatus is facilitated remarkably. Furthermore, any thermal damage which would be incurred on the body or organ is minimized to assure a high level of safety.

The timing of flashing of the light-emitting portion and the timing of switching between the transmitted light image and the reflected light image may be determined automatically in accordance with the count of the number of the frames or may be determined manually by the user depending in accordance with the conditions such as the type of object examined, purpose of the examination, and so forth.

It is also possible to provide an additional memory circuit so that the first memory circuit 457 and the second memory circuit 458 are used exclusively for the dynamic image formed by the reflected light, while the transmitted light image is recorded in the additional memory circuit. With such an arrangement, it is possible to make access to a previously obtained transmitted light image which has been recorded in advance of the presently observed reflected light image. This enables the user to refer to a preceding transmitted light image when the user finds it necessary to make such a reference during observation of the reflected light image.

It is also possible to arrange such that the light-emitting portion 446 flashes in synchronization with only one or two of the R, G and B color light signals, so that the internal illumination is used at a certain level of light intensity during flashing of the light-emitting portion 446. With such an arrangement, it is possible to display on the same frame an image synthesized from an ordinary color image produced by the internal illumination and a transmitted light image in one or two of the R, G and B colors or a complementary color.

Both the twenty-eighth and twenty-ninth embodiments may be arranged such that the still image and the dynamic images are displayed on the same monitor device or on the independent monitor devices.

According to the twenty-eighth and twenty-ninth embodiments described hereinbefore, the user can easily conduct a switching the operation between a mode in which the monitor device displays a reflected light image produced by the reflected internal illumination light and suitable for observation of abnormality such as small height difference or delicate change in the color tone on the surface of a membrana, and a mode in which monitor device displays a transmitted light image which enables the state of tissue under the membrana, e.g., state of running of blood vessels under the membrana and area of any disease or infiltration in the tissue under the membrana. The user therefore can continuously examine both types of image, whereby the accuracy of the diagnosis is improved. In addition, since the light-emitting portion light only intermittently, the total irradiating energy applied to the body is minimized to ensure a high level of safety. The intermittent lighting of the light source also facilitates the design of apparatus having a compact size.

Obviously, the described embodiments are only illustrative and various other forms of the invention can be obtained without departing from the spirit and scope of the present invention. FIGS. 49 to 53 show the thirtieth embodiment of the present invention. As shown in FIG. 49, an endoscope apparatus is formed of an endoscope 501 provided with a means of observing the inside of a living body 525 and a light source apparatus 530 feeding the endoscope 501 with the illuminating light reflectively illuminating the observed part from inside the body and an illuminating light transmissively illuminating the observed part from outside the body.

The above mentioned endoscope 501 is provided with an elongated and, for example, flexible insertable part 502 and a thick operating part 503 connected to the insertable part 502 at the rear end. A flexible universal cord 504 is extended sidewise and is provided at the tip with a connector 505 to be connected to the above mentioned light source apparatus 530.

Figure 50:
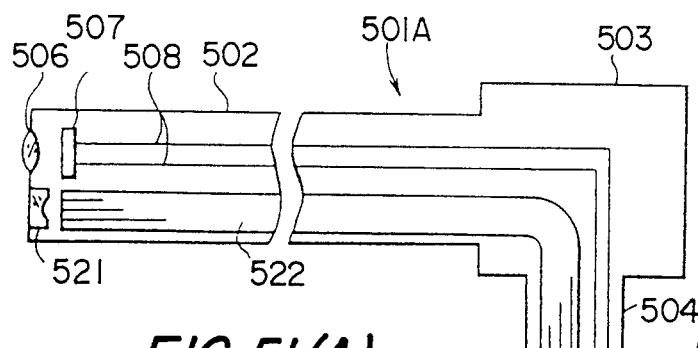
Figure 51A:
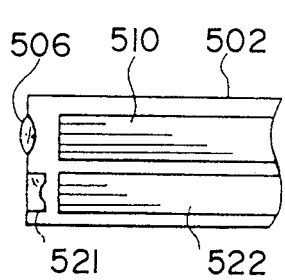
Figure 52:
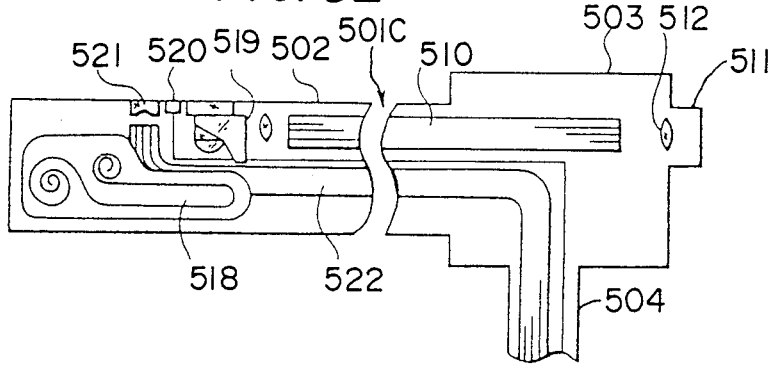

The above mentioned endoscope 501 may be an electronic scope 501A as shown in FIG. 50, a fiber scope 501B as shown in FIG. 51(A) or a tip camera fitted fiber scope 501C as shown in FIG. 52.

The above mentioned electronic scope 501A is provided in the tip part of the insertable part 502 with an objective lens system 506. A solid state imaging device 507 having a sensitivity to visible light and infrared light is arranged in the image forming position of the objective lens system. Signal lines are connected to the solid state imaging device 507, are inserted through the above mentioned insertable part 502 and universal cord 504, are connected to the above mentioned connector 505 and are connected to a video signal processing circuit not illustrate through the connector 505.

In the above mentioned fiber scope 501B, an image guide 510 made, for example, of a fiber bundle is arranged on the tip surface in the image forming position of the objective lens system 506. This image guide 510 is inserted through the insertable part 502 and is to transmit an object image to an eyepiece part 511 side connected to the operating part 503 at the rear end so that the object image transmitted by the above mentioned image guide 510 can be observed through an eyepiece lens 512 from the above mentioned eyepiece part.

Figure 51B:
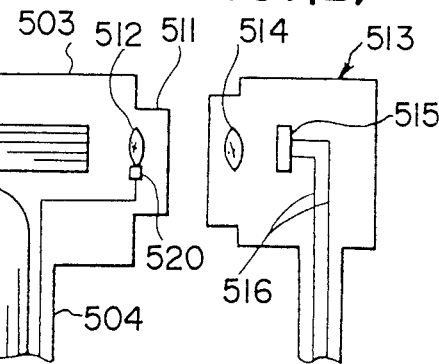

Also, an externally fitted television camera 513 as shown in FIG. 51(B) and a still camera not illustrated can be connected to the above mentioned eyepiece part 511. The above mentioned externally fitted television camera 513 is provided with an image forming lens 514 and a solid state imaging device 515 arranged in the image forming position of the image forming lens 514 so that the object image observed with the above mentioned fiber scope 501B can be images. The above mentioned solid state imaging device 515 is connected to a video signal processing circuit not illustrated through signal lines 516. A light receiving device 520 detecting a received light amount is arranged in the above mentioned fiber scope 501B, for example, in the eyepiece part 511.

In the above mentioned tip camera fitted fiber scope 501C a film 518 having a sensitivity to the visible light and infrared light is arranged within the tip part of the insertable part 502 and an image guide 510 is inserted through the insertable part. An image forming optical system 519 forming an object image, for example, in a sidewise visual field on the above mentioned film 518 and the tip surface of the above mentioned image guide 510 is provided within the tip part of the above mentioned insertable part 502.

In the tip camera fitted fiber scope 501C, the light receiving device 520 is arranged, for example, near the entrance surface of the above mentioned image forming optical system 519.

A light distributing lens 521 is provided in the tip part of each of the above mentioned respective scopes 501A, 501B and 501C and a light guide 522 consisting, for example, of a fiber bundle is provided on the rear end side of the light distributing lens 521. The light guide 522 is inserted through the above mentioned insertable part 502 and universal cord 504 and is connected to the above mentioned connector 505.

On the other hand, a light source apparatus 530 of this embodiment is provided with a reflective illumination lamp 531 arranged within a light source apparatus body 530a and a transmissive illumination lamp 532 arranged in the position opposed to the part observed with the above mentioned endoscope 501 through a living body 525 from outside the body to obtain a transmittal light picture image. The above mentioned reflected illumination lamp 531 emits a visible light or invisible light required to observe, for example, a living body inside. On the other hand, the above mentioned transmitted illumination lamp 532 emits mostly, for example, an infrared light. A common power source circuit 533 feeding an electric power to the above mentioned reflected illumination lamp 531 and transmitted illumination lamp 532 is provided and is connected to the above mentioned reflected illumination lamp 531 directly and to the above mentioned transmitted illumination lamp 532 through an exposure controlling circuit 534.

An infrared light cutting filter 535 which eliminate the wavelengths in the infrared light range from becoming unnecessary heat except for the visible light, an iris 536 which adjust the light amount of the above reflected illumination lamp 531 and a condenser lens 537 which condenses the light bundle adjusted in the light amounts by the above mentioned iris 536 and which inputs the light into the light guide 522 at the entrance end of the above mentioned endoscope 501, are arranged in turn forward of the above mentioned reflected illumination lamp 531.

On the other hand, a filter 538 which eliminates the wavelengths of light at which the transmitted degree through the living body 525 is so low as to generate heat and eliminate the wavelengths which are unnecessary for the observation.

The above mentioned light source apparatus 530 is provided with an exposure level detecting circuit 540 detecting the brightness of the part observed with the above mentioned endoscope 501. In the exposure level detecting circuit 540, the exposure levels will be detected from the outputs of the solid state imaging devices 507 and 515, for example, when the electronic scope 501A is used and when the externally fitted television camera 513 is used and from the output of the light receiving device 520 when the fiber scope 501B is used and when the tip camera fitted fiber scope 501C is used. The above mentioned iris 536 is controlled by a reflected illumination exposure controlling circuit 541 so that the level may be proper for the reflected illumination in response to the exposure level detected by the above mentioned exposure level detecting circuit 540. On the other hand, the electric power fed to the transmitted illumination lamp 532 from the power source circuit 533 is controlled by the transmitted illumination exposure controlling circuit 534 so that the level may be proper for the transmitted illumination in response to the exposure level detected by the above mentioned exposure level detecting circuit 540.

The operation of this embodiment by the above formation shall be explained in the following.

For the light of the wavelength required to observe the inside of the body cavity 526, light in a visible light or invisible light range will be emitted from the reflected illumination lamp 531, will have a light in an infrared light range which is unnecessary for the observation and which becomes heat removed by the infrared light cutting filter 535, will have the light amount passing through the light path adjusted by the iris 536, will be condensed by the condenser lens 537 and will enter the light guide 522 at the entrance end of the endoscope 501. The light will be led to the tip part of the insertable part 502 of the endoscope 501 by the above mentioned light guide 522, will be emitted from the exit end, will pass through the light distributing lens 521 and will be radiated to an observed part within the body cavity 526. The reflected light image of the observed part by the inside illuminating light will be observed by the observing means of the endoscope 501.

On the other hand, a light centered at an infrared light range will be emitted from the transmitted illumination lamp 532 arranged in the position opposed to the endoscope 501 through the living body 525 outside the body, will have the light of a low transmittivity wavelength through the living body 525 and which becomes heat and any unnecessary wavelength for observation removed, for example, light in the ultraviolet and visible short wavelength range which is low in transmittivity through the living body will be removed by the filter 538, and will be transmitted through the living body 525 and will reach the inside of the body cavity 526. Thus, a transmitted illuminating light will be observed by the observing means of the endoscope 501.

The exposure levels of the picture images obtained by the above mentioned reflected illuminating light and transmitted illuminating light will be detected by the exposure level detecting circuit 540. When the iris 536 controlled with the exposure controlling circuit 541 by the reflected illumination in response to the exposure level detected by the exposure level detecting circuit 540 and, on the other hand, when the electric power fed to the transmitted illumination lamp 532 from the power source circuit is controlled by the exposure controlling circuit 534, the exposure will be controlled so as to be at a proper level.

Thus, in this embodiment, the light source apparatus 530 can emit a reflected illuminating light and transmitted illuminating light. Therefore, when observing the living body 525 inside with the endoscope 501, there can be obtained a transmitted picture image whereby a disease can be detected and diagnosed by observing the variations of the concavo-convexes and tone of the mucous membrane surface with the same reflected illumination as in the past and the vein running below the mucous membrane and the penetrating range of a disease below the mucous membrane, which have not been detected with the conventional technique, can be detected. Thus, the disease diagnosing activity can be improved.

Further, since the reflected illumination lamp 531, transmitted illumination lamp 532, power source circuit 533 common to both lamps, and an exposure controlling means such as the exposure controlling circuits 534 and 541 are made integral, the entire light source apparatus will be made small and the operatability will be improved.

Also, in this embodiment, since the transmitted illumination exposure controlling circuit 534 and power source circuit 533 are contained in the light source apparatus body 530a and are separated from the transmitted illumination lamp 532, amount that the transmitted illumination lamp 532 is moved will be small and light weight, the operatability of the system of the light source apparatus 530 will be improved, the secondary circuit and patient circuit will be easily isolated from each other and safety will be improved.

Since the means of controlling the exposure to the reflected illuminating light and transmitted illuminating light are provided, a proper reflected picture image and transmitted picture image will be able to be observed and an image of an optimum ratio will be able to be obtained by variably controlling the ratio of the reflected picture image and transmitted picture image.

Figure 53:
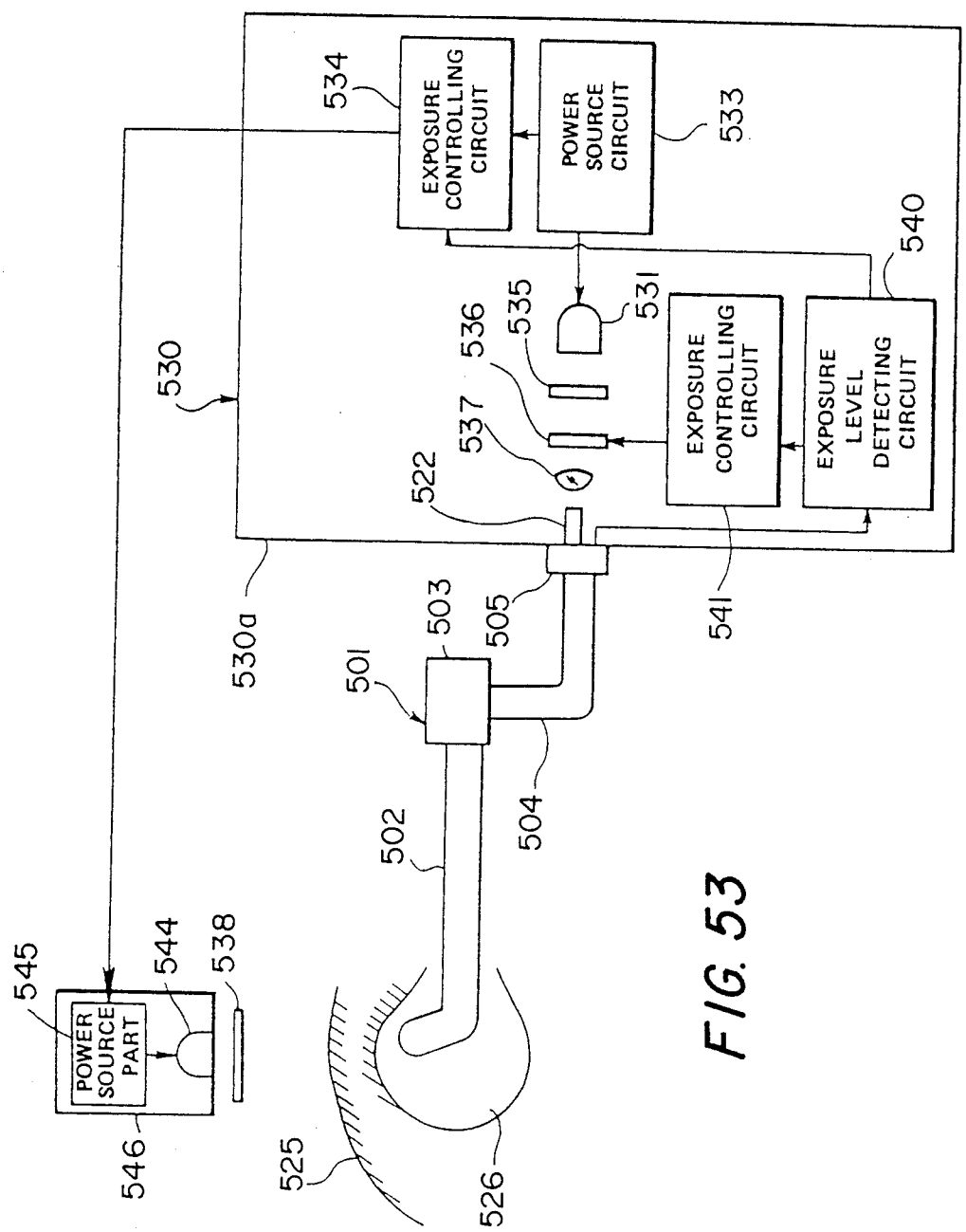

As shown in FIG. 53 when using a light source 544 such as a small stroboscope for the transmitted illumination, the exposure detecting level circuit 540 and exposure controlling circuit 534 are contained in the light source apparatus body 530 and the power source part 545 controlled by the exposure controlling circuit 534 to control the emitted light amount of the light source 544 is contained in the lamp house 546 so that the transmitted light illuminating light source may be controlled.

As a means of detecting the received light amount, the electronic scope 501A or externally fitted television camera 513 may be provided with a light receiving device in the tip part or a fiber scope 501B or the tip camera fitted fiber scope 501C may be provided with a light receiving device in the eyepiece part (FIGS. 50, 51A, 51B, 52).

Figure 54:
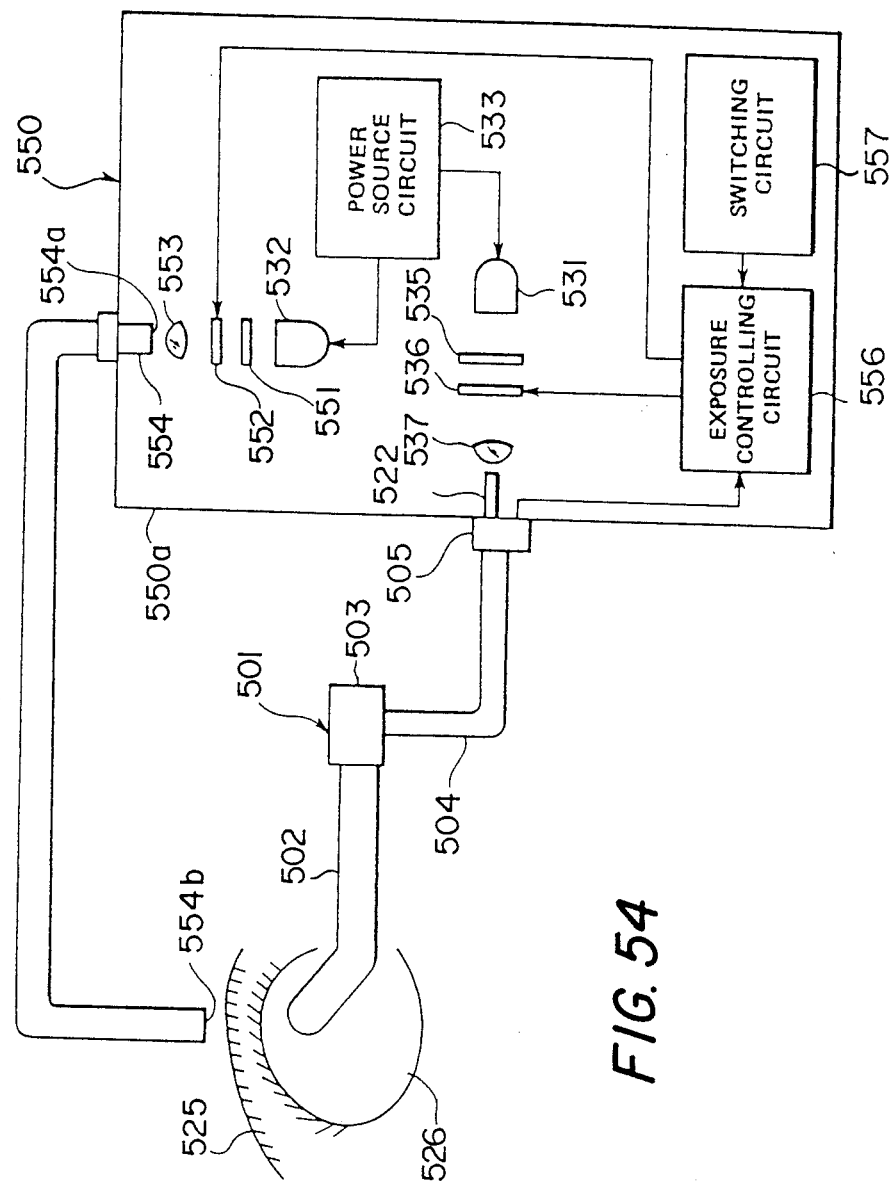
FIG. 54 is a block diagram showing the formation of a light source apparatus of the thirty-first embodiment of the present invention.

FIG. 54 shows the thirty-first embodiment of the present invention.

In a light source apparatus 550 of this embodiment, the reflected illumination lamp 53 and transmitted illumination lamp 532 are contained in a light source apparatus body 550a and are connected to the common power source circuit 533. The same as in the thirtieth embodiment, the infrared light cutting filter, iris 536 and condenser lens 537 are arranged in turn forward of the above mentioned reflected illumination lamp 531.

On the other hand, a filter 551 which transmits the light on the long wavelength side high in the transmittivity through a living body and cutting the light on the short wavelength side low in the transmittivity, an iris 552 which adjusts the light amount and a condenser lens 553 which condenses the light bundle adjusted by the above mentioned iris 552, are arranged in turn forward of the above mentioned transmitted illumination lamp 532. A light guide 554 is extended from the above mentioned light source apparatus body 550a so that the light condensed by the above mentioned condenser lens 553 may enter the light guide 554 at the entrance end 554a. The light guide 554 is arranged at the exit end in the position opposed to the part observed with the endoscope 501 through the living body 525.

Also, in this embodiment, there is provided an exposure controlling circuit 556 controlling the exposure to be of a proper value by detecting the exposures of both of the reflected picture image of the part observed with the reflected illuminating light transmitted through the light guide 522 provided within the above mentioned endoscope 501 and the transmitted picture image of the part observed with the transmitted illuminating light transmitted through the above mentioned light guides 554 and controlling the above mentioned irises 536 and 552.

Further, there is provided a switching circuit 557 which can be switched to only the reflected illumination, transmitted illumination or both simultaneous illuminations by controlling the above mentioned exposure controlling circuit 556.

The other formations are the same as in the thirtieth embodiment.

In this embodiment, the above mentioned transmitted illumination lamp 532 will emit a light centered in a near infrared wavelength range which has high transmittivity through the living body 525. The light will have the unnecessary short wavelength range absorbed or reflected by the filter 551, will have the light amount adjusted by the iris 552, then will be condensed by the condenser lens 553 and will enter the light guide 554 at the entrance end 554a. The light will be emitted from the above mentioned light guide 554 at the exit end 554b arranged in the position opposed to the part observed with the endoscope 501 through the living body 525 and a transmitted picture image of the observed part will be obtained by the transmitted illuminating light. The reflected illuminating light will be radiated to the observed part through the same source as in the thirtieth embodiment.

The exposure levels of the reflected picture image by the reflected illuminating light and the transmitted picture image by the transmitted illuminating light will be detected by the common exposure controlling circuit 556 which will control the respective exposures by controlling the reflected illumination iris 536 and transmitted illumination iris 552.

Only the reflected illumination, transmitted illumination or both simultaneous illuminations can be switched by the switching circuit 557.

According to this embodiment, as the reflected illumination and transmitted illumination power source circuit 533 and exposure controlling circuit 556 are made common, the light source apparatus 550 can be made small and simple.

Also, as the transmitted illumination lamp 532 is provided within the light source apparatus body 550a so as to transmit the transmitted illuminating light through the light guide 554, the transmitted illumination lamp 532 which contacts the living body 525 in the thirtieth embodiment will be electrically insulated by the above mentioned light guide 554 and safety will be high. Since there is no lamp house, the transmitted illuminating light exit part will be made small and will become easy to operate.

The other operations and effects are the same as in the thirtieth embodiment.

Figure 55:
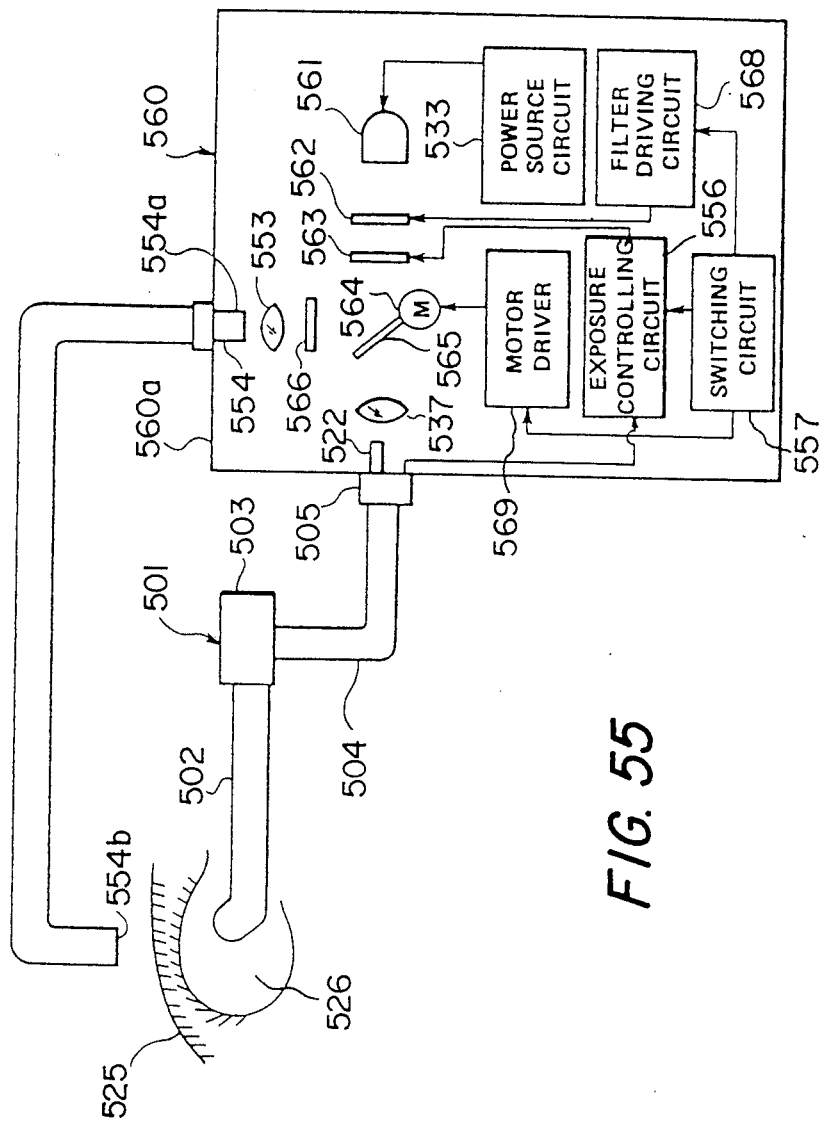
FIG. 55 is a block diagram showing the formation of a light source apparatus of the thirty-second embodiment of the present invention.

FIG. 55 shows the thirty-second embodiment of the present invention.

In a light source apparatus 560 of this embodiment, a lamp 561 common to the reflected illumination and transmitted illumination is provided within a light source apparatus body 560a. An infrared light cutting filter 562, an iris 563 adjusting the light amount and a mirror 565 rotated by a motor 564 and switched to be retreated from the light path of the light from the above mentioned lamp 561 and to be interposed in the light path to divide the light from the above mentioned lamp 561 into two directions are arranged in turn forward of this lamp 561. In the light path of the light from the lamp 561 when the above mentioned mirror 565 is retreated from the light path of the light from the lamp 561, there is arranged a condenser lens 537 condensing the light and entering it into the light guide 522 at the entrance end. On the other hand, when the above mentioned mirror 565 is interposed in the light path of the light from the lamp 561 as inclined, for example, by forty-five (45) degrees, the light from the above mentioned lamp 561 will be reflected in the vertical direction. A filter 566 transmitting the light on the long wavelength side which is high in transmittivity through the living body 525 but cutting the light on the short wavelength side which is low in transmittivity through the living body 525 and a condenser lens 553 condensing the light and entering it into the light guide 554 at the entrance end 554a, are arranged in turn in the light path of the light reflected by the mirror 565.

The above mentioned infrared light cutting filter 562 will be driven by a filter driving circuit 568 to be inserted into and removed from the light path of the light emitted from the above mentioned lamp 561. Also, there is provided an exposure controlling circuit 556 controlling the exposure to be of a proper value by detecting the exposures of both of the reflected picture image of the part observed with the reflected illuminating light transmitted through the light guide 522 provided within the above mentioned endoscope 501 and the transmitted picture image of the part observed with the transmitted illuminating light transmitted through the above mentioned light guide 554 and controlling the above mentioned iris 563.

In this embodiment, the reflected illumination or transmitted illumination will be switched on by controlling the above mentioned filter driving circuit 568 motor driver 569 and exposure controlling circuit 556 with the switching circuit 557.

That is to say, at the time of the reflected illumination, the infrared light cutting filter 565 will be interposed in the light path and the mirror 565 will be retreated from the light path. Therefore, the light emitted from the lamp 561 will have the wavelengths in the infrared light range unnecessary for the reflected illumination cut by the infrared light cutting filter 562, will be adjusted to be of a proper light amount by the iris 563, then will be condensed by the condenser lens 537 and will enter the light guide 522 of the endoscope 501.

On the other hand, at the time of the transmitted illumination, the infrared light cutting filter 562 will be retreated from the light path and the mirror 565 will be interposed in the light path. Therefore, the light emitted from the lamp 506a and including the infrared light will be adjusted to be of a proper light amount by the iris 563 and will be reflected in the vertical direction by the mirror 565. This light will have the light on the long wavelength side which is high in transmittivity through the living body 525 transmitted by the filter 566, will have the light on the short wavelength side which is low in transmittivity through the living body 525 cut, will be condensed by the condenser lens 553 and will enter the light guide 554.

The picture image by the reflected illumination or transmitted illumination will be exposed by controlling the iris 564 with the exposure controlling circuit.

According to this embodiment, the same as in the thirty-first embodiment, the transmitted illumination lamp 532 will be electrically insulated, safety will be improved, the transmitted illuminating light emitting part will be made small and operation will be easy. Since the lamp 561 and power source circuit 533 are made common, the light source apparatus 560 will be made small and light weight.

The other formations, operations and effects are the same as in the thirtieth embodiment.

In the present invention, when a solid state imaging device is used for the observing means, the picture image may be either monochromatic or colored. For a colored picture image, the color imaging system may be of either a frame sequential type in which the illuminating light is switched to red (R), green (G) and blue (B), etc. or a simultaneous type in which a color filter array made by arranging in the form a mosaic color filters transmitting respectively the respective colors such as R, G and B is provided on the front surface of a solid state imaging device.

Figure 56:
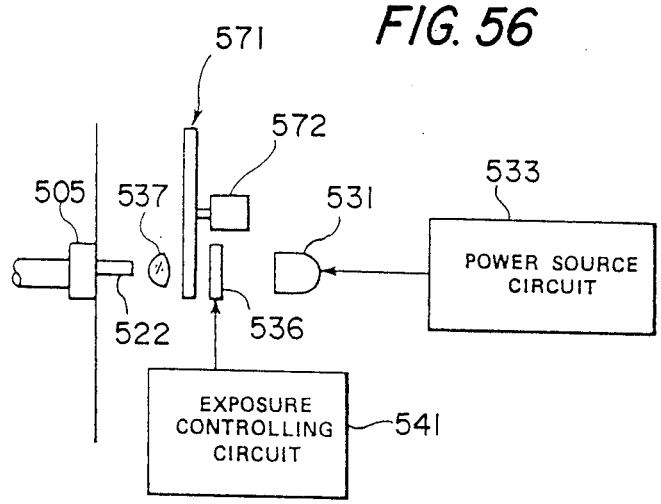
FIGS. 56 and 57 relate to the thirty-third embodiment of the present invention.
Figure 57:
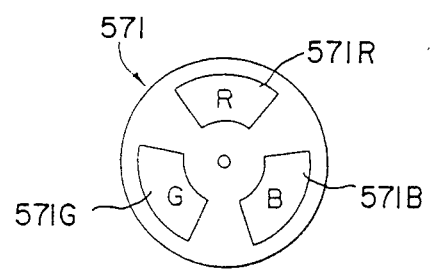

FIGS. 56 and 57 show the thirty-third embodiment of the present invention.

This embodiment is an example of a light source apparatus which can output an illuminating light corresponding to the frame sequential type to illuminate the body inside.

As shown in FIG. 56, a rotary filter 571 rotated and driven by a motor 572 is arranged in the light path between the reflected illumination lamp 531 and the entrance end of the light guide 522 in the thirtieth embodiment, for example, between the iris 536 and condenser lens 537. In the rotary filter 571, as shown in FIG. 57, filters 571R, 571G and 571B transmitting the light in the respective wavelength ranges of R, G and B are arranged in the peripheral direction.

In this embodiment, the light emitted from the lamp 531 will be converted to light in the respective wavelength ranges of R, G and B by passing in turn through the respective filters 571R, 571G and 571B of the above mentioned rotary filter 571. The respective light of R, G and B will enter the light guide 522 in time series. The object to be observed will be reflectively illuminated by the frame sequential light of R, G and B.

In this embodiment, as the infrared rays are cut by the above mentioned rotary filter 571, the infrared light cutting filter 535 is not provided.

The other formations, operations and effects are the same as in the thirtieth embodiment.

In this embodiment, only the reflected illuminating light from inside the body is made a frame sequential light but, for example, in the thirty-first embodiment, rotary filters may be provided respectively in the light paths of the lamps 531 and 532 and both of the reflected illuminating light from inside the body and the transmitted illuminating light from outside the body may be made frame sequential light or only the transmitted illuminating light may be made a frame sequential light. For example, when an infrared light is used for the transmitted illuminating light, three filters transmitting three different wavelength ranges in the infrared light range may be provided for these transmitted illumination rotary filters. Thereby, the transmitted light image of the observed part of the infrared light range can be displayed in quasi colors.

It is apparent that, in this invention, working modes different in a wide range can be formed on the basis of this invention without departing from the spirit and scope of the invention. This invention is not restricted by its specific working modes except being limited by the appended claims.

What is claimed is:

1. An endoscope apparatus comprising:
    external illuminating means for illuminating an interior of an organic body across an organic tissue of said body with an illumination light including at least infrared rays;
    an elongated insert portion to be inserted into said body; and
    image pickup means, having a light-receiving portion provided on said insert portion and being sensitive at least to infrared rays, said image pickup means for picking up an image of an object in or on said body formed by the illumination light emitted from said external illuminating means and transmitted through said organic tissue of said body.

2. An endoscope apparatus according to claim 1, further comprising another illuminating means for applying illumination light to the interior of said body from an inside of said body.

3. An endoscope apparatus according to claim 2, wherein said image pickup means being a solid-state image pickup device provided on an end of said insert portion.

4. An endoscope according to claim 3, further comprising detecting means for detecting a quantity of infrared rays so as to detect a position of said external illuminating means.

5. An endoscope apparatus according to claim 2, further comprising an ocular portion provided on a rear end of said insert portion, an image-forming optical system provided on an inner end of said insert portion, and an image transmitting system through which an object image formed by said image-forming optical system is transmitted to said ocular portion.

6. An endoscope apparatus according to claim 5, wherein said image pickup means includes a television camera connected to said ocular portion.

7. An endoscope apparatus according to claim 5, wherein said image pickup means includes a still camera attached to said ocular portion.

8. An endoscope apparatus according to claims 2 or 5, wherein said image pickup means includes a photographing device provided on the inner end of said insert portion.

9. An endoscope apparatus according to claim 1, wherein said first illuminating means includes light guide means for introducing the illuminating light to a position which is inside said body and which opposes said light-receiving portion of said image pickup means across said organic tissue.

10. An endoscope apparatus according to claim 9, wherein said light guide means includes a light guide of an endoscope which is inserted into said body through a pierced hole formed a wall of said body.

11. An endoscope apparatus according to claim 1, further comprising means for removing heat-generating rays from the external illuminating light emitted from said external illuminating means.

12. An endoscope apparatus comprising:
external illuminating means for illuminating an interior of an organic body across an organic tissue of said body with an illumination light of a wavelength region greater than a red wavelength region;
an elongated insert portion to be inserted into said body; and
image pickup means, having a light-receiving portion provided on said insert portion and a solid-state image pickup device, said image pickup means for picking up an image of an object in or on said body formed by the illumination light emitted from said external illuminating means and transmitted through said organic tissue of said body.

13. An endoscope apparatus according to claim 12, further comprising another illuminating means for applying illumination light to an interior of said body from an inside of said body.

14. An endoscope apparatus comprising:
external illuminating means for illuminating an interior of an organic body across an organic tissue of said body with an illumination light including at least infrared rays;
an elongated insert portion to be inserted into said body; and
image pickup means, having a light-receiving portion provided on said insert portion and being sensitive at least to infrared rays, said image pickup means for picking up an image of an object in or on said body formed by the illumination light emitted from said external illuminating means and transmitted through said organic tissue of said body; and
an illuminating light quantity control means for controlling a quantity of the illuminating light emitted from said external illuminating means.

15. An endoscope apparatus according to claim 14, further comprising another illuminating means for applying illumination light to an interior of said body from an inside of said body.

16. An endoscope apparatus according to claim 15, wherein said illuminating light quantity control means is provided in a vicinity of a manipulating portion which is connected to an outer end of said insert portion.

17. An endoscope apparatus according to claim 15, wherein said image pickup means includes a solid-state image pickup device provided on an inner end of said insert portion.

18. An endoscope apparatus according to claim 15, further comprising detecting means for detecting a quantity of the infrared rays received by said image pickup means, and comparing means for comparing the quantity detected by said detecting means with a predetermined value, said control means for controlling the quantity of light emitted from external illuminating means in accordance with the output from said comparing means so as to maintain the quantity of light impinging upon said image pickup means substantially constant.

19. An endoscope apparatus according to claim 14, wherein said illuminating light quantity control means causing said illuminating means to flash.

20. An endoscope apparatus comprising:
external illuminating means for illuminating an interior of an organic body across an organic tissue of said body with an illumination light including at least infrared rays;
an elongated insert portion to be inserted into said body; and
image pickup means, having a light-receiving portion provided on an insert portion and being sensitive at least to infrared rays, said image pickup means for picking up an image of an object in or on said body formed by the illumination light emitted from said external illuminating means and transmitted through said organic tissue of said body;
detecting means for detecting a quantity of light impinging upon said image pickup means; and
illuminating light control means for controlling a quantity of light emitted from said external illuminating means such that the quantity of light impinging upon said image-pickup means is maintained substantially constant.

21. An endoscope apparatus according to claim 20, further comprising signal processing means for video-processing an output signal of said image pickup means, detecting means for detecting the quantity of light received by said image pickup means from an output of said signal processing means, and comparing means for comparing the light quantity detected by said detecting means with a predetermined value, said control means for controlling the quantity of light emitted from said external illuminating means in accordance with an output from said comparing means so as to maintain the quantity of light impinging upon said image pickup means substantially constant.

22. An endoscope apparatus comprising:
first illuminating means for externally illuminating an interior of an organic body across organic tissue of said body with illuminating light including at least infrared rays;

second illuminating means for applying illuminating light to the interior of said body from an inside of said body;

an elongated insert portion to be inserted into said body;

image pickup means having a light-receiving portion provided on an inner end of said insert portion, said image pickup means for picking up an image of an object on or in said body illuminated by said first and second illuminating means; and illuminating light quantity control means for controlling at least one of the quantities of light emitted from said first and second illuminating means.

23. An endoscope apparatus comprising:

first illuminating means for externally illuminating an interior of an organic body with an illuminating light across organic tissues of said body;

an elongated insert portion to be inserted into said body;

second illuminating means having a light-emitting portion provided on said insert portion so as to be able to apply illuminating light to the interior of said organic body;

image pickup means having a light-receiving portion provided on said insert portion; and exposure amount control means for controlling at least one of an amount of exposure of said image pickup means by the illuminating light from said first illuminating means and an amount of exposure of said image pickup means by the illuminating light from said second illuminating means.

24. An endoscope apparatus according to claim 23, wherein said image pickup means includes a solid-state image pickup device provided on an inner end of said insert portion.

25. An endoscope apparatus according to claim 24, further comprising detecting means for detecting, from an output signal of said image pickup means, levels of signals representing a transmitted light image produced by the illuminating light from said first illuminating means and a reflecting light image produced by the illuminating light from said second illuminating means, as well as for detecting a ratio between levels of said signals, said exposure amount control means for controlling quantities of light emitted from said first and second illuminating means in accordance with output signals from said detecting means.

26. An endoscope apparatus according to claim 25, wherein said first illuminating means emits illuminating light including at least infrared rays, while said second illuminating means emits light which does not include infrared rays.

27. An endoscope apparatus according to claim 26, wherein said second illuminating means emits visible rays.

28. An endoscope apparatus according to claim 26, wherein said second illuminating means emits ultraviolet rays.

29. An endoscope apparatus according to claim 26, wherein said image pickup means is provided on a portion of a light-receiving surface thereof with a detecting portion detecting only one of the illuminating light from said first illuminating means and the illuminating light from the second illuminating means, said detecting means including means for detecting light quantity of one of said first and second illuminating means in accordance with an output from said detecting portion, means for computing a sum of the light quantities of said first and second light illuminating means from an output surface of said light-receiving surface other than said detecting portion, and means for computing levels of signals corresponding to said transmitted light image and said reflected light image, as well as the ratio between the levels of said signals, from the light quantity of one of said illuminating means and said sum of said light quantities.

30. An endoscope apparatus according to claim 26, further comprising a light-receiving element receiving only one of the illuminating lights from said first and second illuminating means, said detecting means including means for detecting the light quantity of one of said first and second illuminating means in accordance with an output from said light-receiving element, means for computing a sum of the light quantities of said first and second light illuminating means from an output surface of said light-receiving surface other than said detecting portion, and means for computing levels of signals corresponding to said transmitted light image and said reflected light image, as well as a ratio between the levels of said signals, from the light quantity of one of said illuminating means and said sum of said light quantities.

31. An endoscope apparatus according to claim 25, wherein said second illuminating means includes means for emitting lights of different colors in a time-serial manner, said first illuminating means includes means for emitting light in synchronization with emission of at least one of said lights of different colors, said image pickup Means including signal processing means for conducting video-processing of output signals of said solid-state image pickup device obtained for respective colors by allocating said output signals, to different colors, as color signals, whereby levels of the signals corresponding to said transmitted light image and said reflected light image, as well as a ratio between the levels of said signals, from a chroma-level or a hue of the video signal produced by said video signal processing means.

32. An endoscope according to claim 25, wherein said second illuminating means includes means for emitting lights of different colors in a time-serial manner, while said first illuminating means includes means for emitting flash light, said image pickup means including signal processing means for conducting video-processing of output signals of said solid-state image pickup device obtained for respective colors by allocating output signals, to different colors, as color signals, said detecting means to detect a signal level of said transmitted light image from a level of an output of said image pickup means obtained when said first illuminating means flashes, whereby the level of the signal corresponding to said reflected light image is detected from the level of the output signal of said image pickup means as obtained when said first illuminating means is not flashing.

33. An endoscope apparatus according to claim 32, wherein said first illuminating means flashes in a period between successive emissions of lights of different colors.

34. An endoscope apparatus according to claim 32, wherein said first illuminating means is for flashing in a period after completion of transfer of signal charges in said image pickup means and before said second illuminating means starts to emit lights of different colors.

35. An endoscope apparatus according to claim 25, wherein said exposure amount controlling means includes a ratio setting means for setting a ratio between signal levels of said transmitted light image and said reflected light image, and control means for conducting a control such as to make the detected ratio between the signal levels of said transmitted light image and said reflected light image equal to a level set by said ratio setting means.

36. An endoscope apparatus according to claim 35 wherein said ratio setting means includes means for varying said ratio in relation to time.

37. An endoscope apparatus according to claim 35, wherein said ratio setting means includes means for holding the ratio at a predetermined value.

38. An endoscope apparatus according to claim 35, further comprising means for selectively causing one of said first and second illuminating means to operate in a switchable manner, and said exposure amount control means includes means for controlling light quantities from both illuminating means such that amounts of exposure by both illuminating means satisfy the ratio set by said ratio setting means.

39. An endoscope apparatus according to claim 25, further comprising signal processing means for video-processing an output of said image pickup means, a pair of memory means for storing video signals from said signal processing means, and control means for causing said first and second illuminating means to operate alternatingly and for controlling said pair of memory means in synchronization with switching between both said illuminating means.

40. An endoscope apparatus according to claim 23, further comprising an ocular portion provided on therearound of said insert portion, an image-forming optical system provided on an inner end of said insert portion, and an image transmission system for transmitting an object image formed by said image-forming optical system to said ocular portion.

41. An endoscope apparatus according to claim 40, wherein said image pickup means includes a television camera connected to said ocular portion.

42. An endoscope apparatus according to claim 40, wherein said image pickup means includes a still camera attached to said ocular portion.

43. An endoscope apparatus according to any one of claims 23 or 40, wherein said image pickup means includes a photographing device provided on the inner end of said insert portion.

44. An endoscope apparatus comprising:
first illuminating means, which can flash intermittently or which can increase a quantity of light emitted therefrom, said first illuminating means for applying externally illuminating light to an interior of an organic body across organic tissue of said body;
an elongated portion to be inserted into said body;
second illuminating means having a light emitting portion provided on said insert portion, said second illuminating means for applying an illuminating light to the interior of said body from an inside of said body;
image pickup means having a light-receiving portion provided on said insert portion for picking up illuminating light from said first and second illuminating means;
signal processing means for conducting a video-processing on an output of said image pickup means so as to form a visible image of said object;
memory means for storing an image formed by said illuminating light from said first illuminating means; and
display means for displaying the image formed by said illuminating light of said first illuminating means and stored in said memory means, and an image formed by said illuminating light of said second illuminating means.

45. An endoscope apparatus according to claim 44, further comprising selecting means for selecting one of said images formed by the illuminating light of said first illuminating means and stored in said memory means and said image formed by the illuminating light of said second illuminating means, and for enabling said display means to display the image selected by said selection means.

46. An endoscope apparatus according to claim 45, further comprising control means which causes said selection means to select the image stored in said memory means for a predetermined time, after said first illuminating has flashed or increased a quantity of light therefrom and after the image formed by the illuminating light of said first illuminating means is stored in said memory means.

47. An endoscope apparatus according to claim 44, further comprising light quantity control means for reducing the light quantity of said second illuminating means when said first illuminating means flashes or when the light quantity of said first illuminating means is increased.

48. An endoscope apparatus according to claim 25 further comprising a controlling means for making said first illuminating means and second illuminating means alternately emit light.

49. An endoscope apparatus according to claim 48 further comprising a separating means for separating the output signal of said image pickup means into a component by the illuminating light of said first illuminating means and a component by said second illuminating means as synchronized with light emitting timings of said first and second illuminating means, and said detecting means detecting the levels of the signals of an object illuminated by the illuminating lights of the respective illuminating means separated by said separating means, and said detecting means detecting the signals of said transmitted light image and reflected light image and the ratio of the levels.

50. An endoscope light source apparatus comprising:
a body inside illuminating light source feeding an illuminating light for reflectively illuminating from inside the body the part observed with the endoscope;
a body outside illuminating means transmittively illuminating from outside the body the part observed with the endoscope; and
said body inside illuminating light source and at least a part of said body outside illuminating means are made as one unit.

51. An endoscope light source apparatus according to claim 50 further comprising an exposure controlling means controlling at least one of the exposure to the body inside illuminating light emitted from said body inside illuminating light source and the exposure to the body outside illuminating light of said body outside illuminating means.

52. An endoscope light source apparatus according to claim 51 wherein said body outside illuminating means has a body outside illuminating light source made common with said body inside illuminating light source and a light transmitting means transmitting the light emitted from said outside illuminating light source to a predetermined position outside the body and emitting it.

53. An endoscope light source apparatus according to claim 50 further comprising a switching means feeding the light emitted from the light source made by making said body inside illuminating light source and body outside illuminating light source common selectively to one of the endoscope and said light transmitting means.

54. An endoscope light source apparatus according to claim 50 wherein said body outside illuminating means has a body outside illuminating light source arranged in the position opposed to the part observed with the endoscope through the living body from outside the body.

55. An endoscope light source apparatus according to claim 54 wherein a power source feeding an electric power to said body inside illuminating light source and a power source feeding an electric power to said body outside illuminating light source are common.

56. An endoscope light source apparatus according to claim 54 further comprising an exposure controlling means controlling the exposure to a body inside illuminating light emitted from said body inside illuminating light source and the exposure to a body outside illuminating light of said body outside illuminating means and a power source feeding an electric power to said body inside illuminating light source and body outside illuminating light source, said exposure controlling means and power source being made integral.

57. An endoscope light source apparatus according to claim 54 wherein the power source feeding an electric power to said body outside illuminating light source is made integral with said body outside illuminating light source.

58. An endoscope light source apparatus according to claim 50 wherein said body outside illuminating means has a body outside illuminating light source made integral with said body inside illuminating light source and a light transmitting means transmitting the light emitted from said body outside illuminating light source to a predetermined position outside the body and emitting it.

59. An endoscope light source apparatus according to claim 58 wherein the power source feeding an electric power to said body inside illuminating light source and the power source feeding an electric power to said body outside illuminating light source are common.

60. An endoscope light source apparatus according to claim 59 further comprising an exposure controlling means controlling the exposure to the body inside illuminating light emitted from said body inside illuminating light source and the exposure to the body outside illuminating light of said body outside illuminating means and a power source feeding an electric power to said body inside illuminating light source and body outside illuminating light source, said exposure controlling means and power source being made integral.

61. An endoscope light source apparatus according to claim 59 wherein the circuit for controlling the exposure to the body inside illuminating light emitted from said body inside illuminating light source and the circuit for controlling the exposure to the body outside illuminating light of said body outside illuminating means are common.

62. An endoscope light source apparatus according to claim 50 wherein the illuminating light by said body outside illuminating means is an infrared light.

63. An endoscope light source apparatus according to claim 50 wherein at least one of the body inside illumination and body outside illumination is of a frame sequential light.

64. An endoscope system comprising:
a light source apparatus having a body inside illuminating light source feeding an illuminating light for reflectively illuminating from inside the body the part observed with the endoscope and a body outside illuminating means transmittively illuminating from outside the body the part observed with the endoscope, said body inside illuminating light source and at least a part of said body outside illuminating means are made as one unit; and
an endoscope having an elongated insertable part having an observing window and illuminating window in the tip part, an observing means for observing the observed part by receiving the light from the observed part entering through said observing window and a light transmitting means transmitting to said illuminating window the light emitted from said body inside illuminating light source to observe the part illuminated by the body inside illuminating light and body outside illuminating light fed by said light source apparatus.

65. An endoscope system according to claim 64 wherein said observing means has an image forming optical system forming an object image by receiving the light entering through said observing window and a solid state imaging device imaging the object image formed by said image forming optical system.

66. An endoscope system according to claim 65 wherein the body inside illuminating light is a visible light, the body outside illuminating light is an infrared light and said solid state imaging device has a sensitivity to the visible light and infrared light.

67. An endoscope system according to claim 64 wherein said observing means has an image forming optical system forming an object image by receiving the light entering through said observing window, an eyepiece part provided on the rear end side of said insertable part and an image transmitting means transmitting the object image formed by said image forming optical system to said eyepiece part.

68. An endoscope system according to claim 67 wherein said observing means further has a television camera removably fitted to said eyepiece part and imaging the object image.

69. An endoscope system according to claim 68 wherein the body inside illuminating light is a visible light, the body outside illuminating light is an infrared light and said television camera has a sensitivity to the visible light and infrared light.

70. An endoscope system according to claim 67 wherein said observing means further has a means of photographing the object image formed by said image forming optical system.

71. An endoscope system according to claim 70 wherein the body inside illuminating light is a visible light, the body outside illuminating light is an infrared light and said photographing means has a sensitivity to the visible light and infrared light.

* * * * *